United States Patent
Shelach

(10) Patent No.: US 10,927,112 B2
(45) Date of Patent: Feb. 23, 2021

(54) BRAF INHIBITORS AND USE THEREOF FOR TREATMENT OF CUTANEOUS REACTIONS

(71) Applicant: LUTRIS PHARMA LTD., Tel Aviv (IL)

(72) Inventor: Noa Shelach, Tel Aviv (IL)

(73) Assignee: Lutris Pharma Ltd., Tel Aviv (IL)

(*) Notice: Subject to any disclaimer, the term of this patent is extended or adjusted under 35 U.S.C. 154(b) by 0 days.

(21) Appl. No.: 16/440,601

(22) Filed: Jun. 13, 2019

(65) Prior Publication Data

US 2019/0389862 A1     Dec. 26, 2019

Related U.S. Application Data

(63) Continuation of application No. PCT/IL2018/050836, filed on Jul. 26, 2018.

(60) Provisional application No. 62/538,675, filed on Jul. 29, 2017.

(51) Int. Cl.
| | |
|---|---|
| *C07D 473/00* | (2006.01) |
| *A61P 17/10* | (2006.01) |
| *A61K 9/00* | (2006.01) |
| *C07D 401/10* | (2006.01) |
| *C07D 401/14* | (2006.01) |

(52) U.S. Cl.
CPC .......... *C07D 473/00* (2013.01); *A61K 9/0014* (2013.01); *A61P 17/10* (2018.01); *C07D 401/10* (2013.01); *C07D 401/14* (2013.01)

(58) Field of Classification Search
CPC .............................. C07D 473/00; A61K 31/52
See application file for complete search history.

(56) References Cited

U.S. PATENT DOCUMENTS

| | | | |
|---|---|---|---|
| 5,753,612 A | 5/1998 | Mitrani | |
| 7,989,461 B2 | 8/2011 | De Morin et al. | |
| 8,440,674 B2 | 5/2013 | De Morin et al. | |
| 8,557,830 B2 | 10/2013 | Smith et al. | |
| 9,388,165 B2 | 7/2016 | Bae et al. | |
| 2013/0226549 A1 | 8/2013 | Tseng et al. | |
| 2014/0005198 A1 | 1/2014 | Smith et al. | |
| 2017/0100345 A1 | 4/2017 | Ribas et al. | |
| 2018/0369247 A1 | 12/2018 | Shelach | |

FOREIGN PATENT DOCUMENTS

WO     2015/171833 A1     11/2015

OTHER PUBLICATIONS

Gencler et al., "Cutaneous Side Effects of BRAF Inhibitors in Advanced Melanoma: Review of the Literature", Dermatology Research and Practice, 2016.

Manousaridis et al., "Cutaneous side effects of inhibitors of the RAS/RAF/MEK/ERK signalling pathway and their management", Journal of the European Academy of Dermatology and Venereology, 27(1), pp. 11-18, 2013.

Ocvirk et al., "A review of the treatment options for skin rash induced by EGFR-targeted therapies: evidence from randomized clinical trials and a metaanalysis"; Radiology and Oncology, 47(2), pp. 166-175, 2013.

(Continued)

*Primary Examiner* — Susanna Moore
(74) *Attorney, Agent, or Firm* — Greenberg Traurig, LLP

(57) ABSTRACT

The present invention discloses novel BRaf inhibitors of formula (I), (II) or (III), wherein R is defined as set forth in the specification, compositions comprising these BRaf inhibitors and uses thereof for the treatment, amelioration and/or prevention of cutaneous reactions.

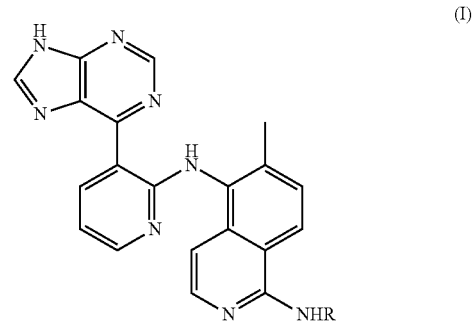

(I)

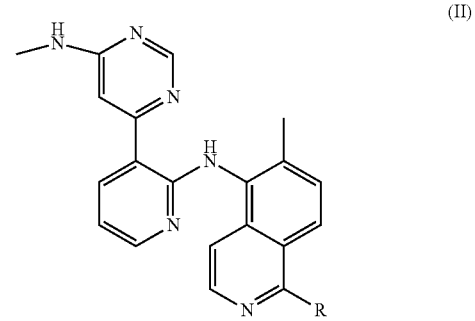

(II)

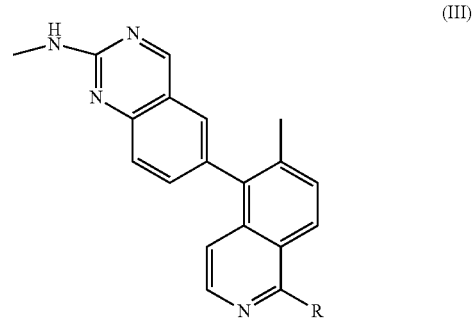

(III)

24 Claims, 8 Drawing Sheets

(56) References Cited

OTHER PUBLICATIONS

Carnahan et al., "Selective and potent Raf inhibitors paradoxically stimulate normal cell proliferation and tumor growth," Mol Cancer Ther. Aug. 2010;9(8):2399-410.
Gibney et al., "Paradoxical oncogenesis and the long-term consequences of BRAF inhibition in melanoma," Nat Rev Clin Oncol. Jul. 2013;10(7):390-9.
Hatzivassiliou et al., "RAF inhibitors prime wild-type RAF to activate the MAPK pathway and enhance growth," Nature 2010, vol. 464, pp. 431-436.
Holcmann et al., "Mechanisms underlying skin disorders induced by EGFR inhibitors," Mol Cell Oncol. Jun. 1, 2015;2(4).
International Search Report and Written Opinion issued in International Application No. PCT/IL2018/050836, dated Jun. 6, 2019, 9 pages.
Smith et al., "Selective Inhibitors of the Mutant B-Raf Pathway: Discovery of a Potent and Orally Bioavailable Aminoisoquinoline," J. Med. Chem. 2009, 52, 6189-6192.

FIG. 2A
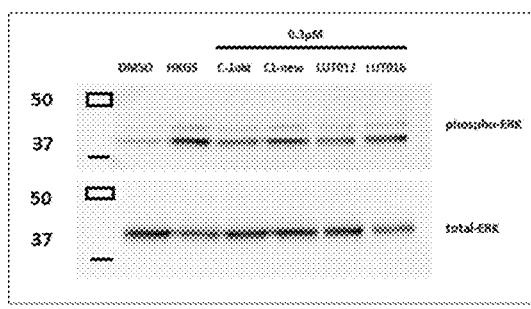
FIG. 2C
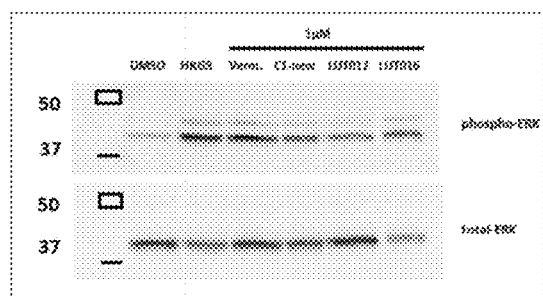
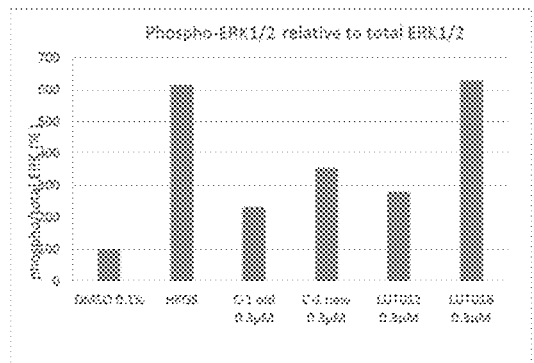
FIG. 2B
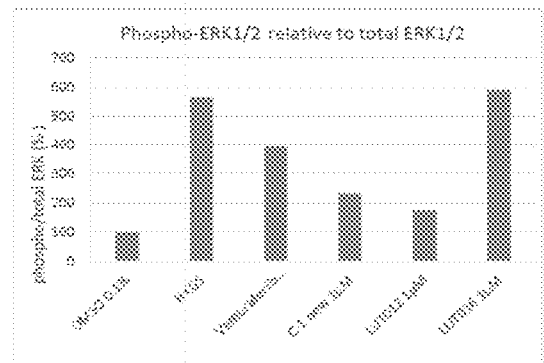
FIG. 2D

Continued

BRAF INHIBITORS AND USE THEREOF FOR TREATMENT OF CUTANEOUS REACTIONS

CROSS REFERENCE TO RELATED APPLICATIONS

This application is a continuation of PCT Application No. PCT/IL2018/050836, filed Jul. 26, 2018, which claims the benefit of priority to U.S. Provisional Patent Application Ser. No. 62/538,675, filed on Jul. 29, 2017, the entire contents of each of which are hereby incorporated by reference in their entirety.

FIELD OF THE INVENTION

The present invention relates to inhibitors of serine/threonine-protein kinase B-Raf (hereinafter "B-Raf" or "BRaf") and compositions and uses thereof.

BACKGROUND

Abnormal activation of Epidermal Growth Factor Receptor (EGFR) is involved in various diseases, in particular, in several types of cancers such as lung cancer, colorectal cancer, head and neck cancer and pancreatic cancer. EGFR antagonists such as monoclonal antibodies (e.g., cetuximab, panitumumab) and small molecule tyrosine kinase inhibitors (e.g. gefitinib, erlotinib, lapatinib) are used for treating many EGFR-mediated cancers. While these EGFR antagonists are useful for treating cancer, they are also associated with severe side effects. One such adverse effect of EGFR antagonists is cutaneous reactions. Cutaneous adverse reactions to EGFR inhibitors include acneiform (papulopustular) rash, abnormal scalp, facial hair and/or eyelash growth, paronychia with or without pyogenic granulomas and telangiectasia.

Various kinases such as phosphatidylinositol-3-kinases (PI 3-kinases), mitogen-activated protein kinases (MAPK), and kinases upstream of MAPK such as MEK and MKK, act as downstream effectors of EGFR and many other receptor tyrosine kinases and are involved in cellular functions such as cell growth, proliferation, differentiation, motility, survival, and intracellular trafficking. Therapeutic agents that target these pathways are also used in the treatment of a number of proliferative diseases, such as melanoma, lung cancer, colorectal cancer, brain cancer, multiple myeloma, pancreatic cancer and neurofibromatosis. Exemplary therapeutic agents that target these pathways include kinase inhibitors such as Trametinib and Cobimetinib. However, inhibitors of these kinases are also associated with adverse side effects. For example, cutaneous adverse events caused by MEK inhibitors have been reported, and include acneiform (papulopustular) rash, abnormal scalp, facial hair and/or eyelash growth, paronychia with or without pyogenic granulomas and telangiectasia.

BRaf is a protein kinase involved in the regulation of the mitogen activated protein kinase (MAPK) signaling pathway. Mutations in BRaf can induce constitutive signaling through the MAPK pathway which may result in uncontrolled cell proliferation. Use of BRaf inhibitors has been demonstrated to be associated with inhibition of MAPK signaling, as can be determined by reduction in levels of phosphorylated ERK, which is the downstream effector of BRaf. Yet, it has been observed that BRaf inhibitors can paradoxically induce an opposite effect of activating MAPK signaling in BRaf wild-type cells (as determined by increased levels of phosphorylated ERK). The underlying mechanisms of paradoxical MAPK activation have been attributed to dimerization of wild-type BRaf and c-Raf and transactivation of the non-inhibited Raf protein leading to subsequent MAPK pathway activation.

Notwithstanding the underlying mechanism(s) causing the cutaneous adverse reactions, these adverse reactions are a serious drawback of the treatment with EGFR, PI3K and/or MEK inhibitors, and may lead to treatment discontinuation and/or poor patient compliance.

Carnahan J. et al. (Mol. Cancer Ther. 9(8) August 2010) found that selective and potent Raf inhibitors can paradoxically stimulate normal cell proliferation. A series of orally bioavailable kinase inhibitors disclosed by Smith A. L. et al., J. Med. Chem. 2009, 52, 6189-6192 showed potent biochemical activity. For example, Compound 1 of the series (C-1) showed significant potency ($^{WT}$B-Raf Ki=1 nmol/L, V600EB-Raf Ki=1 nmol/L, and C-Raf Ki=0.3 nmol/L).

Carnahan et el. found that in cells with wild-type B-Raf and mutated K-ras, exposure to Raf inhibitors resulted in a dose-dependent and sustained paradoxical activation of mitogen-activated protein kinase (MAPK) signaling. Raf inhibition led to entry into the cell cycle and enhanced proliferation.

N. Shelach showed in a co-pending patent application PCT/IL2017/050301 titled "Use of BRaf Inhibitors for Treating Cutaneous Reactions" that this paradoxical activation of MAPK can be used for treating cutaneous adverse reactions induced by treatment with EGFR or PI3K inhibitors.

There is still a need in the art for the development of novel therapeutic compounds, compositions, and methods of treatment, to help alleviate the aforementioned cutaneous adverse reactions associated with administration of EGFR inhibitors, PI3K inhibitors, MEK inhibitors or combinations thereof.

SUMMARY OF THE INVENTION

The present disclosure provides BRaf inhibitors of formula (I), (II), and (III) as defined herein. The present disclosure also provides compositions comprising the compounds of formula (I), (II), and (III) and methods of treating dermatological adverse reactions induced by chemotherapy agents such as EGFR inhibitors, PI3K inhibitors, MEK inhibitors or combinations thereof using the compounds and compositions of the present disclosure.

BRIEF DESCRIPTION OF THE DRAWINGS

FIG. 1A shows Phospho-ERK (upper panel) and total ERK (lower panel) upon treatment with 0.3 µM of the test compounds. FIG. 1B shows the densitometric analysis of blots in FIG. 1A based on the calculation of Phospho-ERK/total ERK ratio. FIG. 1C shows Phospho-ERK (upper panel) and total ERK (lower panel) upon treatment with 1 µM of the test compounds. FIG. 1D shows the densitometric analysis of blots in FIG. 1C based on the calculation of Phospho-ERK/total ERK ratio.

FIGS. 2A-2D depict ERK Phosphorylation induced in HEKa by the compounds—LUT012, LUT016, and C-1. FIG. 2A shows Phospho-ERK (upper panel) and total ERK (lower panel) upon treatment with 0.3 µM of the test compounds. FIG. 2B shows the densitometric analysis of blots in FIG. 2A based on the calculation of Phospho-ERK/ total ERK ratio. FIG. 2C shows Phospho-ERK (upper panel) and total ERK (lower panel) upon treatment with 1 μM of the test compounds. FIG. 2D shows the densitometric analysis of blots in FIG. 2C based on the calculation of Phospho-ERK/total ERK ratio.

FIG. 3A shows Phospho-ERK (upper panel) and total ERK (lower panel) upon treatment with 0.3 μM of the test compounds. FIG. 3B shows Phospho-ERK (upper panel) and total ERK (lower panel) upon treatment with 1 μM of the test compounds. FIG. 3C shows the densitometric analysis of the blot in FIG. 3A based on the calculation of Phospho-ERK/total ERK ratio. FIG. 3D shows the densitometric analysis of the blot in FIG. 3B based on the calculation of Phospho-ERK/total ERK ratio.

FIG. 4A shows Phospho-ERK (upper panel) and total ERK (lower panel) upon treatment with 0.00304, 0.03 μM, and 0.3 μM of the test compounds. FIG. 4B shows the densitometric analysis of blots in FIG. 4A based on the calculation of Phospho-ERK/total ERK ratio.

FIG. 7A shows Phospho-ERK and FIG. 7B shows total ERK upon treatment with the test compounds. FIG. 7C shows the densitometric analysis of blots in FIGS. 7A and 7B based on the calculation of Phospho-ERK/total ERK ratio.

DETAILED DESCRIPTION OF THE INVENTION

Figure 1A:
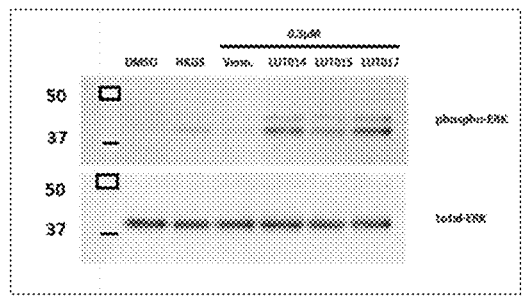
FIGS. 1A-1D depict ERK Phosphorylation induced in HEKa cells by the compounds—LUT014, LUT015, and LUT017.

Provided herein are the compounds of formula (I), (II), and (III) and compositions comprising them. Also provided are methods of treating cutaneous adverse reactions using the compounds and compositions of the present disclosure.

Compounds

In one embodiment, provided herein is a compound of formula (I):

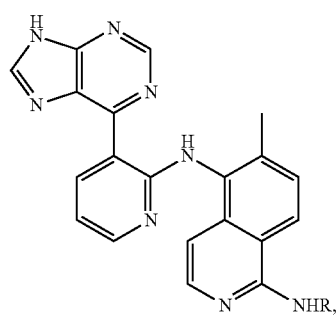

(I)

wherein R is selected from the group consisting of 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl or phenyl-3-sulfonamide, or a pharmaceutically acceptable salt or a solvate thereof.

In another embodiment, provided herein is a compound of formula (II):

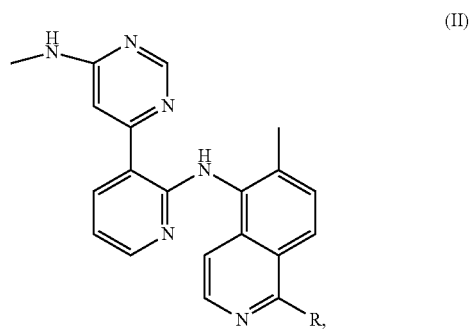

(II)

wherein R is NHR$^1$, wherein R$^1$ is 2-fluoro-4-iodophenyl, or a pharmaceutically acceptable salt or a solvate thereof.

In another embodiment, provided herein is a compound of formula (III):

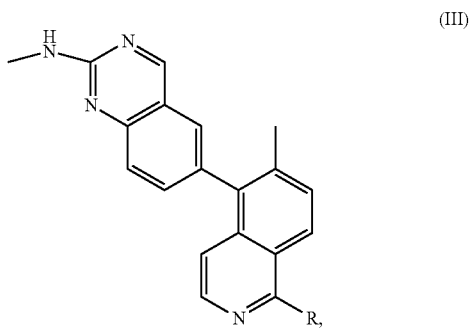

(III)

wherein R is NHR$^1$, wherein R$^1$ is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof.

In one embodiment, the compounds of present disclosure inhibit the activity of BRaf. In one embodiment, the compounds of present disclosure may have an IC50 towards BRaf of about $0.5 \times 10^{-8}$M to about $5 \times 10^{-8}$M, about $1 \times 10^{-8}$M to about $5 \times 10^{-8}$M, about $1 \times 10^{-8}$M to about $3.5 \times 10^{-8}$M, or about $1 \times 10^{-8}$M to about $3 \times 10^{-8}$M.

In one embodiment, the compounds of present disclosure increase the activity of Mitogen-Activated Protein Kinases (MAPK).

In one embodiment, the compounds of present disclosure increase the activity of MAPK and simultaneously inhibit the activity of BRaf.

In one embodiment, the activity of MAPK is determined by measuring the phosphorylation of Extracellular Signal-Regulated Kinase (ERK) and calculating a ratio of phospho-ERK to total ERK.

In one embodiment, the compounds of the present disclosure increase the ratio of phospho-ERK to total ERK by at least about 1.025 fold, 1.05 fold, 1.10-fold, 1.15-fold, 1.20-fold, 1.25-fold, 1.30 fold, 1.35-fold, 1.40-fold, 1.45-fold, 1.5-fold, 1.6-fold, 1.7-fold, 1.8-fold, 2-fold, 2.25-fold, 2.5-fold, 2.75-fold, 3-fold, 3.25-fold, 3.5-fold, 3.75-fold, 4-fold, 4.25-fold, 4.5-fold, 4.75-fold, 5-fold, 5.25-fold, 5.50-fold, 5.75-fold, 6-fold, 6.25-fold, 6.50-fold, 6.75-fold, 7-fold, 7.25-fold, 7.5-fold, 8-fold, 8.5-fold, 9-fold, 9.5-fold, 10-fold, 15-fold, 20-fold, 25-fold, 30-fold, 40-fold, 50-fold, 75-fold, 100-fold, 150-fold, or by about 200-fold, including values and ranges therebetween, compared to untreated or control-treated cells.

In one embodiment, the compounds of the present disclosure increase the ratio of phospho-ERK to total ERK by about 1.5-fold to about 50-fold, about 1.5-fold to about 25-fold, 1.5-fold to about 20-fold, about 1.5-fold to about 15-fold, about 2.5-fold to about 15-fold, about 2.5-fold to about 10-fold, about 3-fold to about 20-fold, about 3-fold to about 15-fold, about 4-fold to about 20-fold, about 4-fold to about 15-fold, about 4-fold to about 10-fold, about 5-fold to about 20-fold, about 5-fold to about 15-fold, including values and ranges therebetween, compared to untreated or control-treated cells.

In one embodiment, the compounds of the present disclosure increase the level of phospho-ERK relative to total ERK by at least about 2.5%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 225%, 250%, 275%, 300%, 325%, 350%, 375% 400%, 425%, 450%, 475%, 500%, 550%, 600%, 650%, 700%, 750%, 800%, 850%, 900%, 950%, 1000%, 1100%, 1200%, 1300%, 1400%, 1500%, 1600%, 1700%, 1800%, 1900%, 2000%, 2250%, 2500%, 2750%, 3000%, 3250%, 3500%, 4000%, 4500%, 4750%, 5000%, 5500%, 6,000%, 6500%, 7,000%, 7500%, 8,000%, 9,000%, or 10,000%, including values and ranges therebetween, compared to untreated or control-treated cells.

In one embodiment, the compounds of present disclosure show no phototoxicity or reduced phototoxicity. The level of phototoxicity can be determined by measuring a Photo-Irritation Factor (PIF) or a Mean Photo Effect (MPE).

In one embodiment, a PIF can be calculated using the following formula: PIF=IC50(−Irr)/IC50(+Irr), where PIF>5 indicates phototoxicity; 2<PIF<5 indicates probable phototoxicity; PIF<2 indicates no phototoxicity. In one embodiment, the compounds of present disclosure have a PIF of less than 5. In another embodiment, the compounds of present disclosure have a PIF of less than 2.

In one embodiment, the MPE can be calculated by comparing the complete concentration-response curves. MPE is a weighted average of the difference in response of equivalent doses normalized by the shift in IC50. MPE>0.15 indicates phototoxicity; 0.1<MPE<0.15 indicates probable phototoxicity; MPE<0.1 indicates no phototoxicity. In one embodiment, the compounds of present disclosure have a MPE of less than 0.15. In another embodiment, the compounds of present disclosure have a MPE of less than 0.1.

Compositions

In one embodiment, provided herein are pharmaceutical compositions comprising a compound of Formula (I):

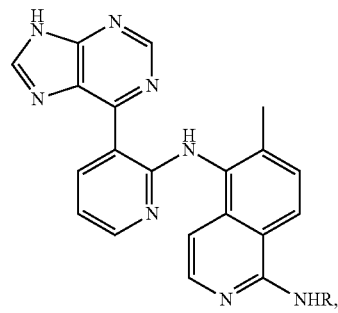

wherein R is selected from the group consisting of p-chlorophenyl, 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof, or a combination thereof; and a pharmaceutically acceptable carrier or excipient.

In one embodiment, provided herein are pharmaceutical compositions comprising a compound of Formula (II) or (III) or a pharmaceutically acceptable salt or a solvate thereof, and a pharmaceutically acceptable carrier or excipient.

In another embodiment, provided herein are pharmaceutical compositions comprising a compound of Formula (I), (II) or (III) or a pharmaceutically acceptable salt or a solvate thereof, or a combination thereof, and a pharmaceutically acceptable carrier or excipient.

In one embodiment, a pharmaceutical composition may comprise about 1% w/w to about 5% w/w of a compound of Formula (I), (II) or (III) or a pharmaceutically acceptable salt or a solvate thereof, or a combination thereof, based on the total weight of the composition. For example, the pharmaceutical composition may comprise about 1%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% w/w, including values and ranges therebetween, of any of the compounds disclosed herein. In some embodiments, the pharmaceutical composition may comprise about 1% to about 3%, about 1% to about 4%, about 1.5% to about 5%, about 1.5% to about 4.5%, about 1.5% to about 3.5%, about 1.5% to about 3%, about 2% to about 5%, about 2% to about 4.5%, about 2% to about 4%, about 2.5% to about 5%, about 2.5% to about 4.5%, about 2.5% to about 4%, about 3% to about 5%, about 3.5% to about 5% w/w, including values and ranges therebetween, of any of the compounds disclosed herein.

In one embodiment, a pharmaceutical composition may comprise about 5% w/w to about 10% w/w of a compound of Formula (I), (II) or (III) or a pharmaceutically acceptable salt or a solvate thereof, or a combination thereof, based on the total weight of the composition. For example, the pharmaceutical composition may comprise about 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 7.1%, 7.2%, 7.3%, 7.4%, 7.5%, 7.6%, 7.7%, 7.8%, 7.9%, 8%, 8.1%, 8.2%, 8.3%, 8.4%, 8.5%, 8.6%, 8.7%, 8.8%, 8.9%, 9%, 9.1%, 9.2%, 9.3%, 9.4%, 9.5%, 9.6%, 9.7%, 9.8%, 9.9%, or 10% w/w, including values and ranges therebetween, of any of the compounds disclosed herein. In some embodiments, the pharmaceutical composition may comprise about 5% to about 9%, about 5% to about 8.5%, about 5% to about 8%, about 5% to about 7.5%, about 5% to about 7%, about 6% to about 10%, about 6% to about 9%, about 6% to about 8.5%, about 6% to about 8%, about 7% to about 10%, about 7% to about 9.5%, about 7% to about 8.5%, about 7.5% to about 10%, about 8% to about 10% w/w, including values and ranges therebetween, of any of the compounds disclosed herein.

In some other embodiments, the pharmaceutical composition may comprise about 1% to about 10%, about 1% to about 8%, about 1% to about 7%, about 2% to about 8%, about 2% to about 7%, about 2% to about 6%, about 2.5% to about 7.5%, about 2.5% to about 5.5%, about 3% to about 8%, about 3% to about 7%, about 4% to about 8%, about 4% to about 7%, about 4.5% to about 7.5%, about 4.5% to about 7%, or about 4.5% to about 6.5% w/w, including values and ranges therebetween, of any of the compounds disclosed herein.

In one embodiment, the pharmaceutical composition comprising any one of the compounds disclosed herein is formulated for systemic administration. Systemic administration can be via enteral or parenteral route of administration. In one embodiment, systemic administration is oral administration, and the pharmaceutical composition is formulated for oral administration (oral pharmaceutical composition).

In one embodiment, provided herein is an oral pharmaceutical composition comprising a compound of Formula (I), (II) or (III) or a pharmaceutically acceptable salt or a solvate thereof, or a combination thereof, and a pharmaceutically acceptable carrier or excipient. Oral pharmaceutical compositions of the present disclosure can be in the form of a solid dosage form or a liquid dosage form and may comprise any of the disclosed compound(s) in any of the amounts described herein.

In one embodiment, the pharmaceutical composition comprising any one of the compounds disclosed herein is formulated for topical administration. Topical administration comprises local application of the composition to the skin, nails, eyes, eyelashes, eyelids, and/or hair of the subject.

In one embodiment, provided herein is a topical pharmaceutical composition comprising a compound of Formula (I), (II) or (III) or a pharmaceutically acceptable salt or a solvate thereof, or a combination thereof, and a pharmaceutically acceptable carrier or excipient. Compositions for topical administration (topical compositions) can be in the form of a gel, a hydrogel, an ointment, a cream, a foam, a spray, a lotion, a liquid, or a dermal patch and may comprise any of the disclosed compound(s) in any of the amounts described herein.

In one embodiment, an oral or a topical pharmaceutical composition comprises a compound of formula:

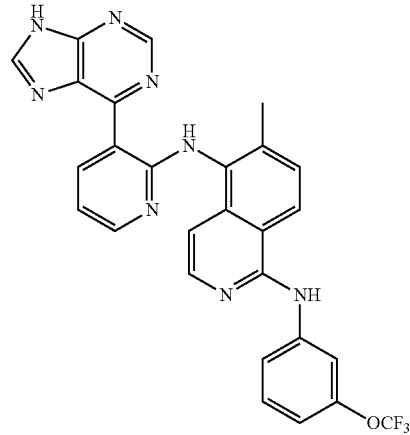

LUT014 in any of the amounts disclosed herein and a pharmaceutically acceptable carrier or excipient.

In one embodiment, provided herein is a topical pharmaceutical composition comprising LUT014 in any of the w/w % amounts disclosed herein and a pharmaceutically acceptable carrier or excipient. The topical composition comprising LUT014 may be formulated in a dosage form selected from ointment, cream, gel, hydrogel, foam, spray, lotion, liquid and dermal patch.

In one embodiment, provided herein is an oral pharmaceutical composition comprising LUT014 in any of the w/w % amounts disclosed herein and a pharmaceutically acceptable carrier or excipient. The oral pharmaceutical composition comprising LUT014 can be in the form of a solid dosage form or a liquid dosage form.

Solid dosage forms for oral administration include capsules, tablets, powders, and granules. In such solid dosage forms, the active compound is admixed with at least one inert excipient (or carrier) such as sodium citrate or dicalcium phosphate or (a) fillers or extenders, for example, starches, lactose, sucrose, mannitol, and silicic acid; (b) binders, for example, carboxymethylcellulose, alginates, gelatin, polyvinylpyrrolidone, sucrose, and acacia; (c) humectants, for example, glycerol; (d) disintegrating agents, for example, agar-agar, calcium carbonate, potato or tapioca starch, alginic acid, certain complex silicates, and sodium carbonate; (a) solution retarders, for example, paraffin; (f) absorption accelerators, for example, quaternary ammonium compounds; (g) wetting agents, for example, cetyl alcohol and glycerol monostearate; (h) adsorbents, for example, kaolin and bentonite; and (i) lubricants, for example, talc, calcium stearate, magnesium stearate, solid polyethylene glycols, sodium lauryl sulfate, or mixtures thereof. In the case of capsules, and tablets, the dosage forms may also comprise buffering agents.

An exemplary capsule dosage form may comprise soft or hard-filled gelatin capsules comprising one or more compounds of the present disclosure and excipients such as lactose or milk sugar, high molecular weight polyethylene glycols, and the like.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the liquid dosage forms can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

An exemplary liquid dosage form for oral administration may comprise a syrup comprising one or more compounds of the present disclosure and excipients like glycerol, propylene glycol and sucrose.

Topical compositions useful in the present disclosure may be formulated as a solution. Such compositions may comprise an emollient preferably containing from about 1% to about 50% of an emollient(s). As used herein, the term "emollient" refers to materials used for the prevention or relief of dryness, as well as for the protection of the skin. A number of suitable emollients are known and may be used in the present disclosure. For example, Sagarin, Cosmetics, Science and Technology, 2nd Edition, Vol. 1, pp. 32-43 (1972) and the International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "ICI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72-73 (1972) and the ICI Handbook pp. 1693-1697.

The topical compositions useful in the present disclosure may be formulated as emulsions. If the carrier for a topical composition is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, in McCutcheon's Detergents and Emulsifiers, North American Edition, pp. 317-324 (1986), and the ICI Handbook, pp. 1673-1686.

Lotions and creams can be formulated as emulsions. Such lotions may comprise from 0.5% to about 5% of an emulsifier(s). Creams may comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

The topical compositions of this disclosure can also be formulated as a gel (e.g., an aqueous, alcohol, alcohol/water, or oil gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils include, but are not limited to, hydrogenated butylene/ethylene/styrene copolymer and hydrogenated ethylene/propylene/styrene copolymer. Gel compositions may comprise between about 0.1% and 5%, by weight, of such gelling agents.

In addition to the above carriers and excipients, other emollients and surface active agents can be incorporated into the topical compositions, including glycerol trioleate, acetylated sucrose distearate, sorbitan trioleate, polyoxyethylene (1) monostearate, glycerol monooleate, sucrose distearate, polyethylene glycol (50) monostearate, octylphenoxypoly (ethyleneoxy) ethanol, decaglycerin penta-isostearate, sorbitan sesquioleate, hydroxylated lanolin, lanolin, triglyceryl diisostearate, polyoxyethylene (2) oleyl ether, calcium stearoyl-2-lactylate, methyl glucoside sesquistearate, sorbitan monopalmitate, methoxy polyethylene glycol-22/dodecyl glycol copolymer (Elfacos E200), polyethylene glycol-45/dodecyl glycol copolymer (Elfacos ST9), polyethylene glycol 400 distearate, and lanolin derived sterol extracts, glycol stearate and glycerol stearate; alcohols, such as cetyl alcohol and lanolin alcohol; myristates, such as isopropyl myristate; cetyl palmitate; cholesterol; stearic acid; propylene glycol; glycerin, sorbitol and the like.

Methods

Provided herein are methods of treating, preventing, and/or ameliorating dermatological conditions.

In one embodiment, the dermatological condition is a dermatological or cutaneous adverse reactions induced by chemotherapy agents such as EGFR inhibitors, PI3K inhibitors, MEK inhibitors or combinations thereof.

In one embodiment, provided herein is a method for treating, ameliorating, and/or preventing a cutaneous adverse reaction of EGFR inhibitors, PI3K inhibitors, MEK inhibitors or combinations thereof in a subject in need thereof, comprising administering a therapeutically effective amount of a composition comprising a compound of formula (I)

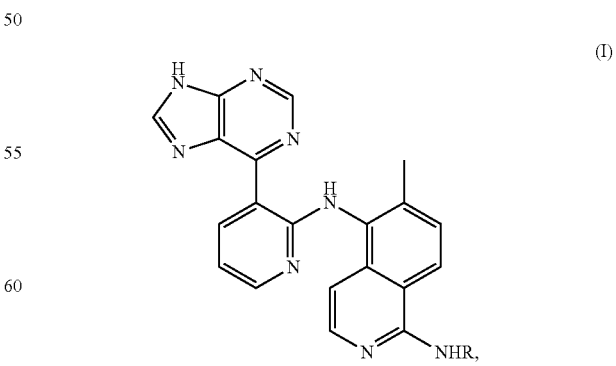

wherein R is selected from the group consisting of p-chlorophenyl, 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof;

a compound of formula (II):

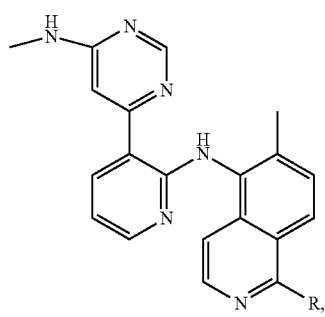

(II)

wherein R is NHR$^1$, wherein R$^1$ is 2-fluoro-4-iodophenyl, or a pharmaceutically acceptable salt or a solvate thereof;

a compound of formula (III):

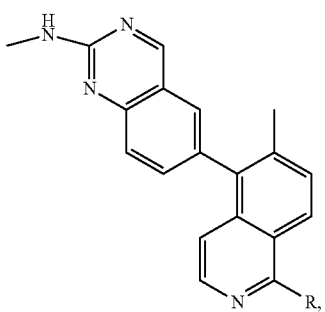

(III)

wherein R is NHR$^1$, wherein R$^1$ is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof;

or a combination thereof; and a pharmaceutically acceptable carrier or excipient.

In one embodiment, methods for treating, ameliorating, and/or preventing a cutaneous adverse reaction of EGFR inhibitors, PI3K inhibitors, MEK inhibitors or combinations thereof in a subject in need thereof comprise administering a therapeutically effective amount of a composition comprising a compound of formula (I), wherein R is selected from the group consisting of p-chlorophenyl, 3-ethynylphenyl, 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, 3,5-dihydroxyphenyl, phenyl-3-sulfonamide or 3-(trifluoromethyl)phenyl, or a pharmaceutically acceptable salt or a solvate thereof, or a combination thereof; and a pharmaceutically acceptable carrier or excipient.

In one embodiment, methods for treating, ameliorating, and/or preventing a cutaneous adverse reaction of EGFR inhibitors, PI3K inhibitors, MEK inhibitors or combinations thereof in a subject in need thereof comprise administering a therapeutically effective amount of a composition comprising a compound of formula (II), wherein R is NHR$^1$, wherein R$^1$ is 2-fluoro-4-iodophenyl, or a pharmaceutically acceptable salt or a solvate thereof; and a pharmaceutically acceptable carrier or excipient.

In one embodiment, methods for treating, ameliorating, and/or preventing a cutaneous adverse reaction of EGFR inhibitors, PI3K inhibitors, MEK inhibitors or combinations thereof in a subject in need thereof comprise administering a therapeutically effective amount of a composition comprising a compound of formula (III), wherein R is NHR$^1$, wherein R$^1$ is 3-ethynylphenyl, 3-chloro-4-fluorophenyl, 2-fluoro-4-iodophenyl, or 4-chloro-3-(trifluoromethyl) phenyl, or a pharmaceutically acceptable salt or a solvate thereof, or a combination thereof; and a pharmaceutically acceptable carrier or excipient.

In one embodiment, methods for treating, ameliorating, and/or preventing a cutaneous adverse reaction of EGFR inhibitors, PI3K inhibitors, MEK inhibitors or combinations thereof in a subject in need thereof comprise administering a therapeutically effective amount of a composition comprising a combination of any of the compounds disclosed herein and a pharmaceutically acceptable carrier or excipient.

In one embodiment, methods for treating, ameliorating, and/or preventing a cutaneous adverse reaction of EGFR inhibitors, PI3K inhibitors, MEK inhibitors or combinations thereof in a subject in need thereof comprise administering a therapeutically effective amount of a composition comprising a compound of formula

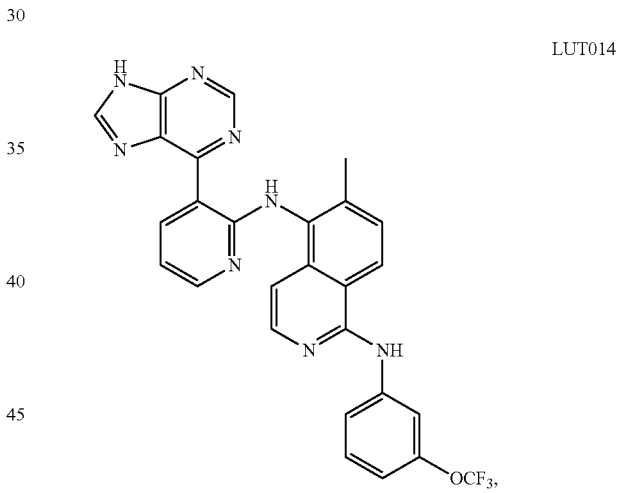

LUT014 in any of the w/w % amounts disclosed herein and a pharmaceutically acceptable carrier or excipient.

Dermatological or cutaneous adverse reactions induced by chemotherapy agents such as EGFR inhibitors, PI3K inhibitors, MEK inhibitors or combinations thereof include acneiform rash, papulopustular rash, abnormal scalp hair growth, abnormal facial hair growth, abnormal hair growth, abnormal eyelash growth, xerosis, pruritus, paronychia with or without pyogenic granulomas and telangiectasia. The methods described herein treat, ameliorate, and/or prevent one or more of these adverse reactions.

In one embodiment, a cutaneous adverse reaction of EGFR inhibitors, PI3K inhibitors, MEK inhibitors or combinations thereof that is treated, ameliorated, and/or prevented by the compounds/compositions of the present disclosure is acneiform rash.

In one embodiment, the subject is a mammal such as a human, dog, and/or cat.

In one embodiment, the subject is receiving an EGFR inhibitor, PI3K inhibitor, MEK inhibitor or a combination thereof at the time of administering the compounds/compositions of the present disclosure. In another embodiment, the compounds/compositions of the present disclosure are administered to the subject prior to or after administration of an EGFR inhibitor, PI3K inhibitor, MEK inhibitor or a combination thereof.

In some embodiments, methods disclosed herein comprise systemic or topical administration of a therapeutically effective amount of the compounds/compositions of the present disclosure.

Methods comprising topical administration comprise local administration or application of any of the compositions disclosed herein to the skin, nails, eyes, eyelashes, eyelids, and/or hair of the subject. In some embodiments, topical administration comprises topically administering a composition formulated in a dosage form selected from a gel, a hydrogel, an ointment, a cream, a spray, a dermal patch, a foam, a lotion and a liquid.

Systemic administration comprises enteral administration or parenteral administration. In some embodiments of the methods disclosed herein, the systemic administration comprises oral administration. In some embodiments of the methods disclosed herein, oral administration comprises administration of an oral dosage form selected from tablet, capsule, liquid, suspension and powder.

In one embodiment, methods disclosed herein comprise systemically or topically administering about 0.1 mg/day to about 1 mg/day of one or more compounds of the present disclosure. In some embodiments, methods disclosed herein comprise systemically or topically administering about 0.1 mg/day, about 0.2 mg/day, about 0.3 mg/day, about 0.4 mg/day, about 0.5 mg/day, about 0.6 mg/day, about 0.7 mg/day, about 0.8 mg/day, about 0.9 mg/day, or about 1 mg/day, including values and ranges therebetween, of one or more compounds of the present disclosure. In some embodiments, methods disclosed herein comprise systemically or topically administering about 0.1 mg/day to about 0.5 mg/day, about 0.2 mg/day to about 0.8 mg/day, about 0.2 mg/day to about 0.5 mg/day, or about 0.5 mg/day to about 1 mg/day, including values and ranges therebetween, of one or more compounds of the present disclosure.

In one embodiment, methods disclosed herein comprise systemically or topically administering about 1 mg/day to about 5 mg/day of one or more compounds of the present disclosure. In some embodiments, methods disclosed herein comprise systemically or topically administering about 1 mg/day, 1.5 mg/day, 2 mg/day, 2.5 mg/day, 3 mg/day, 3.5 mg/day, 4 mg/day, 4.5 mg/day, or 5 mg/day, including values and ranges therebetween, of one or more compounds of the present disclosure.

In one embodiment, methods disclosed herein comprise systemically or topically administering about 5 mg/day to about 10 mg/day of one or more compounds of the present disclosure. In some embodiments, methods disclosed herein comprise systemically or topically administering about 5 mg/day, about 5.5 mg/day, about 6 mg/day, about 6.5 mg/day, about 7 mg/day, about 7.5 mg/day, about 8 mg/day, about 8.5 mg/day, about 9 mg/day, about 9.5 mg/day, or about 10 mg/day, including values and ranges therebetween, of one or more compounds of the present disclosure.

In some embodiments, methods disclosed herein comprise systemically or topically administering about 1 mg/day to about 10 mg/day, about 1 mg/day to about 8 mg/day, about 2 mg/day to about 8 mg/day, about 2.5 mg/day to about 7.5 mg/day, about 3 mg/day to about 8 mg/day, about 3 mg/day to about 6 mg/day, or about 4 mg/day to about 8 mg/day, including values and ranges therebetween, of one or more compounds of the present disclosure.

In one embodiment, the amount of the compound administered depends on the nature of the compound, the mode of administration, and/or the severity of the cutaneous reaction. The therapeutically effective amount that need to be administered to a patient can be determined by dose-ranging clinical studies known in the art.

In some embodiments of the methods disclosed herein, an EGFR inhibitor is selected from Iressa® (gefitinib), Tarceva® (erlotinib), Tykerb® (lapatinib), Erbitux® (cetuximab), Vectibix® (panitumumab), Caprelsa® (vandetanib), Portrazza® (necitumumab), Tagrisso® (osimertinib) and combinations thereof.

In some embodiments of the methods disclosed herein, a PI3K inhibitor is selected from GDC-0980 (Apitolisib), GDC-0941 (Pictilisib), BAY 80-6946 (Copanlisib), BKM120 (Buparlisib), NVP-BEZ235 (Dactolisib), IPI 145 (Duvelisib), Idelalisib (GS-1101 or CAL-101), wortmannin, LY294002 and combinations thereof.

In some embodiments of the methods disclosed herein, a MEK inhibitor is selected from Trametinib (GSK1120212), Cobimetinib (XL518), Binimetinib (MEK162), Selumetinib, PD-325901, CI-1040, PD035901, UO126, TAK-733, and combinations thereof.

In one embodiment, the methods disclosed herein reduce the severity of the cutaneous adverse reactions.

The most commonly used system to grade the severity of cutaneous adverse reactions is National Cancer Institute's Common Terminology Criteria for Adverse Events (CTCAE) version 4.0, which recognizes 4 grades shown in Table 1 below.

TABLE 1

NCI-CTCAE version 4.0 grading scale of skin and subcutaneous tissue disorders

| | |
|---|---|
| Grade 1 | Papules and/or pustules covering <10% of the BSA associated or not associated with symptoms of pruritus or tenderness |
| Grade 2 | Papules and/or pustules covering 10-30% of the BSA associated or not associated with symptoms of pruritus or tenderness; psychosocial impact; limiting instrumental ADL |
| Grade 3 | Papules and/or pustules covering >30% of the BSA associated or not associated with pruritus or tenderness; limiting self-care ADL, associated with local superinfection (oral antibiotics indicated) |
| Grade 4 | Covering any percentage of the BSA associated or not with pruritus or tenderness; associated with severe superinfection (intravenous antibiotics indicated); life-threatening consequences |

BSA = Body surface area;
ADL = activity of daily living

In one embodiment, the methods disclosed herein reduce the severity of the cutaneous adverse reactions from grade 4 to grade 3, 2, 1, or 0, as defined by National Cancer Institute Common Terminology Criteria for Adverse Events (NCI-CTCAE) version 4.0.

In one embodiment, the methods disclosed herein reduce the severity of the cutaneous adverse reactions from grade 3 to grade 2, 1, or 0, as defined by NCI-CTCAE version 4.0.

In one embodiment, the methods disclosed herein reduce the severity of the cutaneous adverse reactions from grade 2 to grade 1 or 0, as defined by NCI-CTCAE version 4.0.

In one embodiment, the methods disclosed herein reduce the severity of the cutaneous adverse reactions from grade 1 to grade 0, as defined by NCI-CTCAE version 4.0.

In one embodiment, the methods disclosed herein prevent, partially or completely, the development of cutaneous adverse reactions.

In one embodiment, the methods disclosed herein prevent, partially or completely, the development of grade 4, grade 3, grade 2, or grade 1 of the cutaneous adverse reactions, as defined by NCI-CTCAE version 4.0.

In one embodiment, the methods disclosed herein prevent the escalation of the cutaneous adverse reaction. For example, in one embodiment, the methods disclosed herein prevent the escalation of the cutaneous adverse reaction from grade 0 to grade 1, 2, 3, or 4, as defined by NCI-CTCAE version 4.0. In another embodiment, the methods disclosed herein prevent the escalation of the cutaneous adverse reaction from grade 1 to grade 2, 3, or 4, as defined by NCI-CTCAE version 4.0. In another embodiment, the methods disclosed herein prevent the escalation of the cutaneous adverse reaction from grade 2 to grade 3 or 4, as defined by NCI-CTCAE version 4.0. In another embodiment, the methods disclosed herein prevent the escalation of the cutaneous adverse reaction from grade 3 to grade 4, as defined by NCI-CTCAE version 4.0.

Another system that may be used to grade the severity of cutaneous adverse reactions is Lacouture grading scale shown in Table 2 below.

TABLE 2

| Adverse Event | Grade 1 | | Grade 2 | | Grade 3 | | Grade 4 |
|---|---|---|---|---|---|---|---|
| Papulopustular eruption Grading individually for face, scalp, chest or back) | 1A Papules or pustules <5 OR 1 area of erythema or edema <1 cm in size | 1B Papules or pustules <5; OR 1 area of erythema or edema <1 cm in size AND pain or pruritus | 2A Papules or pustules 6-20; OR 2-5 areas of erythema or edema <1 cm in size | 2B Papules or pustules 6-20; OR 2-5 areas of erythema or edema <1 cm in size AND pain, pruritus, or effect on emotions or functioning | 3A Papules or pustules >20; OR more than 5 areas of erythema or edema <1 cm in size | 3B Papules or pustules >20; OR more than 5 areas of erythema or edema <1 cm in size AND pain, pruritus, or effect on emotions or functioning | |
| Nail changes-Nail Plate | Onycholysis or ridging without pain | | Onycholysis with mild/moderate pain; any nail plate lesion interfering with instrumental ADL | | Nail plate changes interfering with self-care ADL | | |
| Nail changes-Nail fold | Disruption or absence of cuticle; OR erythema | | Erythematous/tender/painful; OR pyogenic granuloma; OR crusted lesions OR any fold lesion interfering on instrumental ADL | | Periungual abscess: OR fold changes interfering with self-care ADL | | |
| Nail changes-Digit tip | Xerosis AND/OR erythema without pain | | Xerosis AND/OR erythema with mild/moderate pain or stinging; OR fingertip fissures; OR any digit tip lesion interfering with instrumental ADL | | Digit tip lesions interfering with self-care ADL | | |
| Erythema | Painless erythema, blanching; erythema covering <10% BSA | | Painful erythema, blanching; erythema covering 10-30% BSA | | Painful erythema, nonblanching; erythema covering >30% BSA | | |
| Pruritus | Mild OR localized, intermittent, not requiring therapy. | | 2A Moderate localized OR widespread intermittent AND Requiring intervention | 2B Moderate localized OR widespread constant AND Requiring intervention | Severe, widespread constant AND interfering with sleep | | |
| Xerosis | Scaling/flaking covering <10% BSA NO erythema/pruritus/effect on emotions or functioning | | 2A Scaling/flaking covering 10-30% BSA + pruritus OR effect on emotions/ functioning | 2B Scaling/flaking + pruritus covering 10-30% BSA AND effect on emotions/ functioning + erythema | 3A Scaling/flaking covering >30% BSA AND pruritus AND erythema AND effect on emotions/ functioning AND fissuring/ cracking + fissuring/ cracking | 3B Scaling/flaking covering >30% BSA AND pruritus AND erythema AND effect on emotions/ functioning AND fissuring/ cracking + signs of super infection | |
| Hair changes; Scalp hair loss or alopecia | Terminal hair loss <50% of normal for that individual that may or may not be noticeable to others but is associated with increased shedding and overall feeling of less volume. May require different hair style to cover but does not require hairpiece to camouflage | | 2A: Hair loss associated with marked increase in shedding and 50%-74% loss compared to normal for that individual. Hair loss is apparent to others, may be difficult to | 2B: Marked loss of at least 75% hair compared to normal for that individual with inability to camouflage except with a full wig OR new cicatricial hair loss documented | | | |

TABLE 2-continued

| Adverse Event | Grade 1 | | Grade 2 | | Grade 3 | | Grade 4 |
|---|---|---|---|---|---|---|---|
| | | | camouflage with change in hair style and may require hairpiece. | by biopsy that covers at least 5% scalp surface area. May impact on functioning in social, personal or professional situations. | | | |
| Hair Changes: disruption of normal hair growth(specify): Facial hair (diffuse, not just in male beard/mustache areas) Eyelashes Eyebrows Body Hair Beard and moustache hair | Some distortion of hair growth but does not cause symptoms or require intervention, | | 2A: Distortion of hair growth in many hairs in a given area that cause discomfort or symptoms that may require individual hairs to be removed. | 2B: Distortion of hair growth of most hairs in a given area with symptoms or resultant problems requiring removal of multiple hairs. | | | |
| Hair Changes: increased hair changes (specify): Facial hair (diffuse, not just in male beard/mustache areas) Eyelashes Eyebrows Body Hair Beard and moustache hair (hirsutism) | Increase in length, thickness and/or density of hair that the patient is able to camouflage by periodic shaving, bleaching or removal of individual hairs. | | 2A: Increase in length, thickness and/or density of hairs that is very noticeable and requires regular shaving or removal of hairs in order to camouflage. May cause mild symptoms related to hair overgrowth, | 2B: Marked increase in hair density, thickness and/or length of hair that requires either frequent shaving or destruction of the hair to camouflage. May cause symptoms related to hair overgrowth. Without hair removal, inability to function normally in social, personal or professional situations. | | | |
| Flushing | 1A. Face OR chest, asymptomatic, transient | 1B. Any location, asymptomatic, permanent | 2A. Symptomatic on face, or chest, transient | 2B. Symptomatic on face, or chest, permanent | 3A. Face and chest, transient, symptomatic | 2B. Face and chest, permanent, symptomatic | |
| Telangiectasia | One area (<1 cm diameter) NOT affecting emotions or functioning | | 2A 2-5 (<1 cm diameter) areas NOT affecting emotions or functioning | 2B 2-5 (<1 cm diameter) areas affecting emotions or functioning | More than 6 (<1 cm diameter) OR confluent areas affecting emotions or functioning | | |
| Hyper-pigmentation | One area (<1 cm diameter) NOT affecting emotions or functioning | | 2A 2-5 (<1 cm diameter) areas NOT affecting emotions or functioning | 2B 2-5 (<1 cm diameter) areas affecting emotions or functioning | More than 6 (<1 cm diameter) OR confluent areas affecting emotions or functioning | | |
| Mucositis Oral Anal | Mild erythema or edema, and asymptomatic | | Symptomatic (mild pain, opioid not required); erythema or limited ulceration, can eat solid foods and take oral medication (Oral mucositis only) | | Pain requiring opioid analgesic; erythema and ulceration, cannot eat solids, can swallow liquids (Oral mucositis only) | | erythema and ulceration, cannot tolerate PO intake; require tube feeding or hospitalization (Oral mucositis only) |

TABLE 2-continued

| Adverse Event | Grade 1 | Grade 2 | Grade 3 | Grade 4 |
|---|---|---|---|---|
| Radiation dermatitis | Faint erythema or dry desquamation | Moderate to brisk erythema; patchy moist desquamation, mostly confined to skin folds and creases; moderate edema | Moist desquamation other than skin folds and creases; bleeding induced by minor trauma or abrasion | Skin necrosis or ulceration of full thickness dermis; spontaneous bleeding from involved site |
| Hyposalivation | Can eat but requires liquids, no effect on speech | Moderate/thickened saliva: cannot eat dry foods, mild speech impairment (sticky tongue, lips, affecting speech) | No saliva, unable to speak without water, no oral intake without water | |
| Taste | Altered or reduced taste; no impact on oral intake | Altered or reduced taste affecting interest and ability to eat no intervention required | Taste abnormalities, requires intervention | |

In one embodiment, the methods disclosed herein reduce the severity of the cutaneous adverse reactions from grade 4 to grade 3B, 3A, 2B, 2A, 1B, or 1A, as defined by Lacouture grading scale.

In one embodiment, the methods disclosed herein reduce the severity of the cutaneous adverse reactions from grade 3B to grade 3A, 2B, 2A, 1B, or 1A, as defined by Lacouture grading scale.

In one embodiment, the methods disclosed herein reduce the severity of the cutaneous adverse reactions from grade 3A to grade 2B, 2A, 1B, or 1A, as defined by Lacouture grading scale.

In one embodiment, the methods disclosed herein reduce the severity of the cutaneous adverse reactions from grade 2B to grade 2A, 1B, or 1A, as defined by Lacouture grading scale.

In one embodiment, the methods disclosed herein reduce the severity of the cutaneous adverse reactions from grade 2A to grade 1B or 1A, as defined by Lacouture grading scale.

In one embodiment, the methods disclosed herein reduce the severity of the cutaneous adverse reactions from grade 1B to grade 1A, as defined by Lacouture grading scale.

In one embodiment, the methods disclosed herein prevent, partially or completely, the development of grade 4, grade 3B, grade 3A, grade 2B, grade 2A, grade 1B, or grade 1A of the cutaneous adverse reactions, as defined by Lacouture grading scale.

In one embodiment, the methods disclosed herein prevent the escalation of the cutaneous adverse reaction from grade 1A to grade 1B, 2A, 2B, 3A, 3B or 4, as defined by Lacouture grading scale. In another embodiment, the methods disclosed herein prevent the escalation of the cutaneous adverse reaction from grade 1B to grade 2A, 2B, 3A, 3B or 4, as defined by Lacouture grading scale. In one embodiment, the methods disclosed herein prevent the escalation of the cutaneous adverse reaction from grade 2A to grade 2B, 3A, 3B or 4, as defined by Lacouture grading scale. In one embodiment, the methods disclosed herein prevent the escalation of the cutaneous adverse reaction from grade 2B to grade 3A, 3B or 4, as defined by Lacouture grading scale. In one embodiment, the methods disclosed herein prevent the escalation of the cutaneous adverse reaction from grade 3A to grade 3B or 4, as defined by Lacouture grading scale. In one embodiment, the methods disclosed herein prevent the escalation of the cutaneous adverse reaction from grade 3B to grade 4, as defined by Lacouture grading scale.

EXAMPLES

The following examples illustrate certain embodiments of the invention but are not meant to limit the scope of the claims in any way. The following examples are put forth so as to provide those of ordinary skill in the art with a complete disclosure and description of how to make and use the described invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Exemplary methods for synthesizing the compounds of formula I (LUT012-LUT017 and LUT019-LUT020) are disclosed in Examples 1-9.

The known compound C-1 was prepared according to the synthetic procedure detailed in Smith A. L. et al., J. Med. Chem. 2009, 52, 6189-6192.

Example 1

Synthesis of Compound of Formula I, R=3-ethynylphenyl (Compound LUT012)

Preparation of Intermediate 3B-2

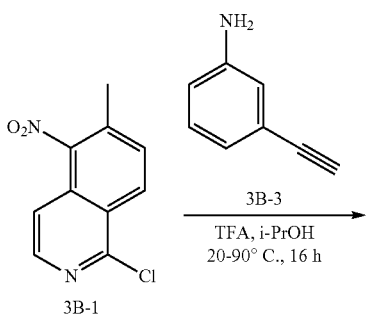

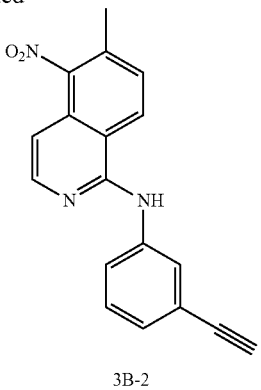

3B-2

To a mixture of compound 3B-1 (2.00 g, 8.98 mmol, 1.0 eq) in isopropanol (20 mL) was added compound 3B-3 (1.26 g, 10.8 mmol, 1.2 eq) and trifluoroacetic acid (1.02 g, 8.98 mmol, 665 uL, 1.0 eq) at 20° C. under nitrogen. The resulting mixture was heated to 90° C. and stirred at 90° C. for 16 h. TLC (petroleum ether:ethyl acetate=3:1, $R_{f-SM}$=0.43, $R_{f-DP}$=0.24) showed the reaction was completed. The reaction mixture was filtered and filter cake was washed with dichloromethane (10 mL), the filter cake was collected and dried in vacuum to give compound 3B-2 (2.60 g, 8.57 mmol, 95.4% yield) as a yellow solid, which was used for next step without further purification.

$^1$H NMR: ET15201-1-P1A 400 MHz MeOD δ 8.74 (d, J=8.8 Hz, 1H), 7.93 (d, J=8.8 Hz, 1H), 7.71 (s, 1H), 7.60-7.71 (m, 4H), 7.10 (d, J=7.2 Hz, 1H), 3.73 (s, 1H), 2.61 (s, 3H).

Preparation of Intermediate 3B

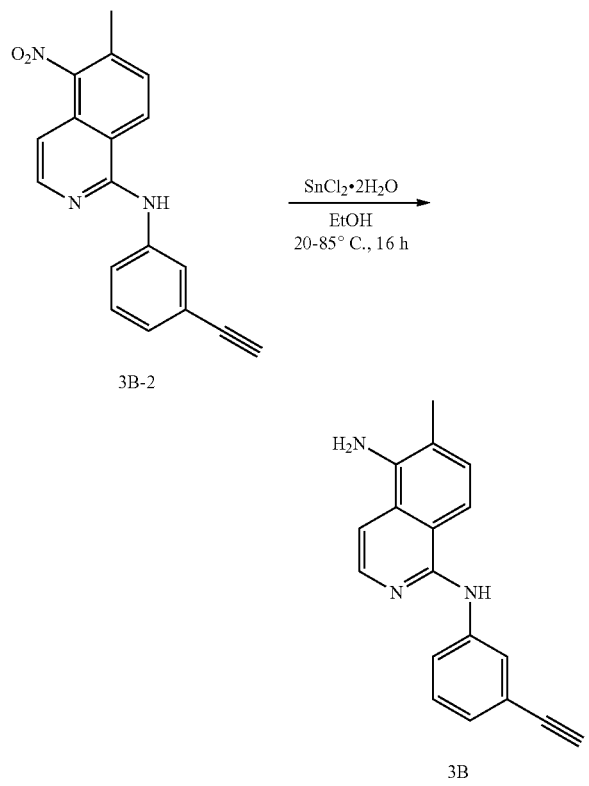

To a mixture of compound 3B-2 (2.60 g, 8.57 mmol, 1.0 eq) in ethanol (26 mL) was added SnCl$_2$.2H$_2$O (9.67 g, 42.9 mmol, 5.0 eq) at 20° C. under nitrogen. The resulting mixture was heated to 85° C. and stirred at 85° C. for 16 h. TLC (petroleum ether:ethyl acetate=2:1, $R_{f-SM}$=0.43, $R_{f-DP}$=0.30) showed the reaction was completed. The reaction mixture was cooled to 20° C. and poured into 5 N NaOH aqueous (50 mL) and stirred for 5 min, filtered and the aqueous phase was extracted with dichloromethane (50 mL, 20 mL). The combined organic phase was dried with anhydrous Na$_2$SO$_4$, filtered and concentrated in vacuum to give compound 3B (2.30 g, crude) as a brown solid, which was used for next step without further purification.

1H NMR: ET15201-4-P1A 400 MHz DMSO-$d_6$ δ 8.96 (s, 1H), 8.12 (s, 1H), 7.90-7.93 (m, 2H), 7.64 (d, J=8.0 Hz, 1H), 7.45 (d, J=6.0 Hz, 1H), 7.25-7.31 (m, 2H), 7.04 (d, J=6.0 Hz, 1H), 5.51 (s, 2H), 4.13 (s, 1H), 2.26 (s, 3H).

Preparation of Intermediate 4B

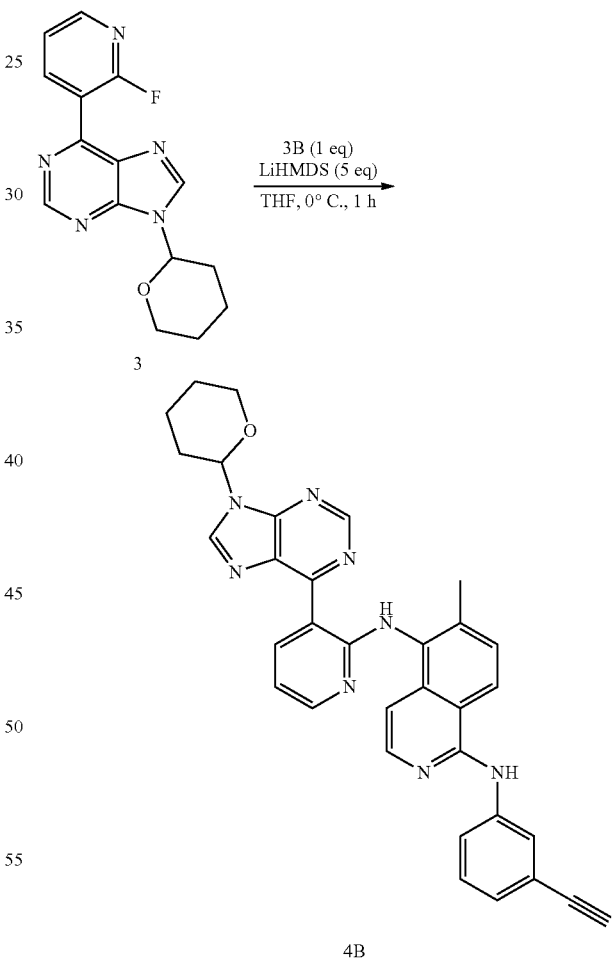

To a mixture of compound 3 (1.00 g, 3.34 mmol, 1.0 eq) and compound 3B (913 mg, 3.34 mmol, 1.0 eq) in tetrahydrofuran (10 mL) was added LiHMDS (1M, 16.7 mL, 5.0 eq) at 0° C. under nitrogen. The resulting mixture was stirred at 0° C. for 1 h. TLC (petroleum ether:ethyl acetate=2:1, $R_{f-SM}$=0.25, $R_{f-DP}$=0.40) showed the reaction was completed. The reaction mixture was quenched with drop-wise addition of ice-water (2 mL) at 0° C. resulting in a light orange solution containing a white solid in suspension. The mixture was concentrated to give a yellow solid which was suspended in ethyl acetate (50 mL), dried with Na$_2$SO$_4$, filtered through a plug of Celite to give a yellow solution and was concentrated in vacuum. The residue was washed with methyl tert-butyl ether (20 mL), filtered to afford the filter cake and the filter cake was dried in vacuum to afford compound 4B (1.10 g, 1.99 mmol, 59.6% yield) as light-yellow solid.

$^1$H NMR: ET15201-9-P1A 400 MHz DMSO-$_{d6}$
δ 11.69 (s, 1H), 9.66 (dd, J=6.0, 1.6 Hz, 1H), 9.28 (s, 1H), 9.12 (s, 1H), 8.97 (s, 1H), 8.42 (d, J=8.8 Hz, 1H), 8.13 (s, 1H), 8.06 (dd, J=2.8, 1.6 Hz, 1H), 7.93-7.96 (m, 2H), 7.60 (d, J=8.8 Hz, 2H), 7.33 (t, J=8.0 Hz, 1H), 7.16 (d, J=6.0 Hz, 1H), 7.08 (d, J=7.6 Hz, 1H), 6.91 (q, J=3.2 Hz, J=0.8 Hz, 1H), 5.89 (d, J=8.8 Hz, 1H), 4.02-4.14 (m, 1H), 3.74-3.79 (m, 1H), 2.36 (s, 4H), 1.99-2.08 (m, 2H), 1.10 (s, 1H).

Preparation of Compound of Formula I,
R=3-ethynylphenyl (Compound LUT012)

Compound 4B (1.10 g, 1.99 mmol, 1.0 eq) was suspended in HCl (0.5M, 35.8 mL, 9.0 eq) at 20° C. under nitrogen. The mixture was heated to 100° C. and stirred for 1 hour. LCMS (ET15201-11-P1A1) showed the reaction was completed. The hot solution was filtered, washing with boiling water (2×20 mL). The resulting solution was cooled in an ice bath and product was crystallized from solution as a yellow solid. The solid was filtered and added to saturated aq. Na$_2$CO$_3$ (100 mL). The mixture was stirred for 10 min and then was filtered, the filtered cake was washed with water (50 mL) and collected as crude product. The crude product was purified by prep-TLC (petroleum ether/ethyl acetate=1/1, R$_f$=0.4) to afford LUT012 (110 mg, 230 umol, 11.6% yield, 98.1% purity) as a yellow solid.

$^1$HNMR: ET15201-11-P1A2 400 MHz DMSO-$_{d6}$
δ 13.84 (br. s, 1H), 11.84 (s, 1H), 9.76 (d, J=7.2 Hz, 1H), 9.25 (s, 1H), 9.06 (s, 1H), 8.73 (s, 1H), 8.41 (d, J=8.4 Hz, 1H), 8.12 (s, 1H), 8.05 (d, J=4.8 Hz, 1H), 7.94 (d, J=6.4 Hz, 2H), 7.61 (d, J=8.4 Hz, 1H), 7.31 (q, J=7.6 Hz, 1H), 7.16 (d, J=5.6 Hz, 1H), 7.08 (d, J=7.6 Hz, 1H), 6.92 (q, J=4.8 Hz, J=3.2 Hz, 1H), 4.14 (s, 1H), 2.37 (s, 3H).

Example 2

Synthesis of Compound of Formula I,
R=1,1-dimethylethyl)-1-methyl-1H-pyrazol-5-yl
(LUT013)

Preparation of intermediate 3C-2

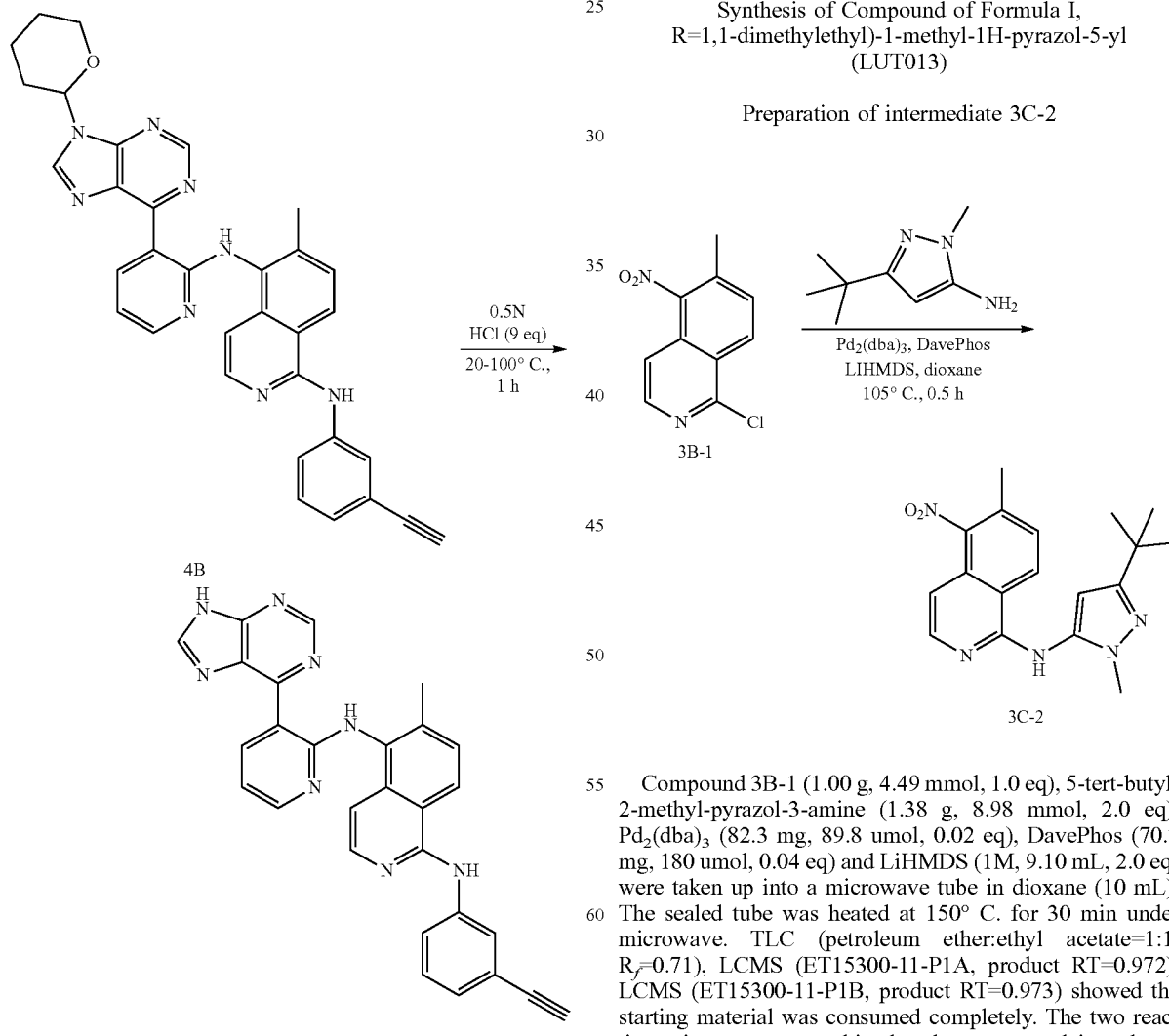

Compound 3B-1 (1.00 g, 4.49 mmol, 1.0 eq), 5-tert-butyl-2-methyl-pyrazol-3-amine (1.38 g, 8.98 mmol, 2.0 eq), Pd$_2$(dba)$_3$ (82.3 mg, 89.8 umol, 0.02 eq), DavePhos (70.7 mg, 180 umol, 0.04 eq) and LiHMDS (1M, 9.10 mL, 2.0 eq) were taken up into a microwave tube in dioxane (10 mL). The sealed tube was heated at 150° C. for 30 min under microwave. TLC (petroleum ether:ethyl acetate=1:1, R$_f$=0.71), LCMS (ET15300-11-P1A, product RT=0.972), LCMS (ET15300-11-P1B, product RT=0.973) showed the starting material was consumed completely. The two reaction mixture were combined and concentrated in reduced pressure at 40° C. The residue was purified by silica gel chromatography (100-200 mesh silica gel), eluted with petroleum ether:ethyl acetate (80:1~0:1) to afford compound 3C-2 (1.00 g, 2.95 mmol, 32.8% yield) as yellow solid.

$^1$H NMR: ET15300-11-P1A 400 MHz CDCl$_3$

δ 8.16 (d, J=6.0 Hz, 1H), 7.90 (d, J=8.4 Hz, 1H), 7.45 (d, J=8.8 Hz, 1H), 7.01 (d, J=6.0 Hz, 1H), 6.08 (s, 1H), 3.72 (s, 3H), 2.55 (s, 3H), 1.34 (s, 9H).

Preparation of Intermediate 3C

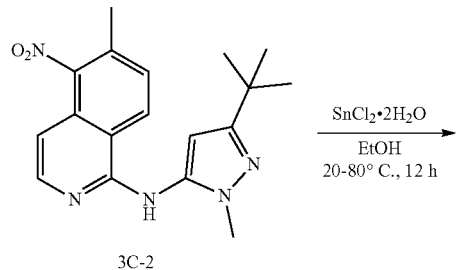

A mixture of compound 3C-2 (1.00 g, 2.95 mmol, 1.0 eq) in ethyl alcohol (20 mL) was added SnCl$_2$.2H$_2$O (3.32 g, 14.7 mmol, 5.0 eq) in one portion at 20° C. under nitrogen. And then the reaction mixture was heated to 80° C. for 12 hrs. TLC (petroleum ether:ethyl acetate=0:1, R$_f$=0.24) and LCMS (ET15300-12-P1A, product: RT=0.793) showed the reaction was completed. The mixture was cooled to 40° C. and concentrated in reduced pressure at 40° C. The residue was poured into dichloromethane (20 mL). The combined organic phase was washed with 5 N aqueous NaOH (10 mL) and stirred for 5 min, the mixture was filtered and concentrated in vacuum. The aqueous phase was extracted with dichloromethane (20 mL, 10 mL). The combined organic phase was washed with brine (15 mL), dried with anhydrous Na$_2$SO$_4$, filtered and concentrated in vacuum. The residue was purified by silica gel chromatography (100-200 mesh silica gel), eluted with petroleum ether:ethyl acetate (50:1-0:1) to afford crude compound 3C (700 mg, 2.26 mmol, 76.8% yield) as yellow solid.

$^1$H NMR: ET15300-12-P1A 400 MHz CDCl$_3$

δ 7.95 (d, J=6.0 Hz, 1H), 7.22 (d, J=8.4 Hz, 1H), 7.13 (d, J=8.8 Hz, 1H), 6.97 (d, J=6.0 Hz, 1H), 6.58 (s, 1H), 4.08 (s, 2H), 3.65 (s, 3H), 2.29 (s, 3H), 1.27 (s, 9H).

Preparation of Intermediate 4C

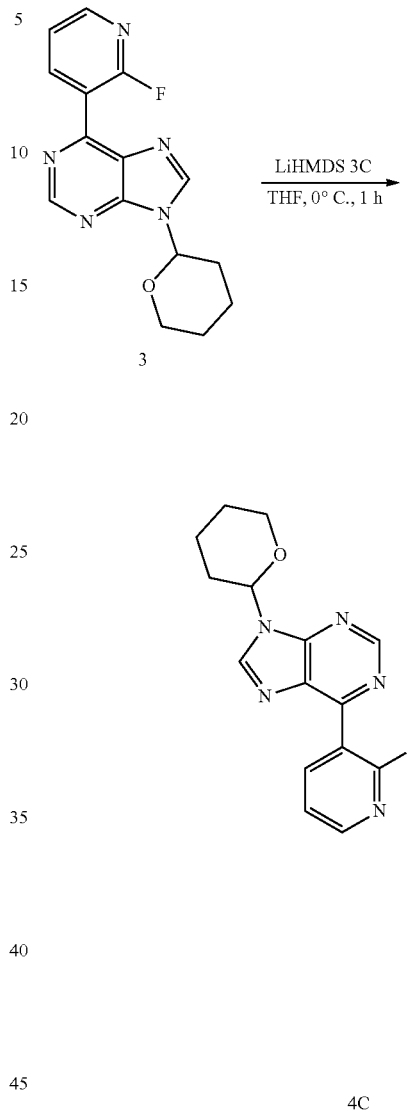

To a solution of compound 3C (310 mg, 1.00 mmol, 1.0 eq) and compound 3 (300 mg, 1.00 mmol, 1.0 eq) in tetrahydrofuran (4.0 mL) was added Li-HMDS (1M, 5.0 mL, 5.0 eq) drop-wise at 0° C. over a period of 60 mins under nitrogen. TLC (petroleum ether:ethyl acetate=0:1, R$_f$=0.34) and LCMS (ET15300-15-P1A, product RT=0.922) showed the reaction was completed. The mixture was concentrated in reduced pressure at 40° C. to afford crude compound 4C (1.00 g, crude) as yellow solid.

Note: Avoid contact with water.

$^1$H NMR: ET15300-15-P1A 400 MHz MeOD

δ 9.72 (dd, J=1.6 Hz, J=7.6 Hz, 1H), 9.04 (s, 1H), 8.71 (s, 1H), 8.20 (d, J=8.4 Hz, 1H), 7.98-8.00 (m, 1H), 7.70 (d, J=6.4 Hz, 1H), 7.59 (d, J=8.8 Hz, 1H), 7.19 (d, J=6.0 Hz, 1H), 6.90 (q, J=5.2 Hz, 1H), 6.07 (s, 1H), 5.92 (dd, J=10.8 Hz, J=13.2, 1H), 4.15-4.18 (m, 1H), 3.65 (s, 3H), 2.43 (s, 3H), 2.14-2.17 (m, 2H), 1.84-2.14 (m, 2H), 1.64-1.70 (m, 2H), 1.33 (s, 9H).

Preparation of Compound of Formula I, R=1,1-dimethylethyl)-1-methyl-1H-pyrazol-5-yl (LUT013)

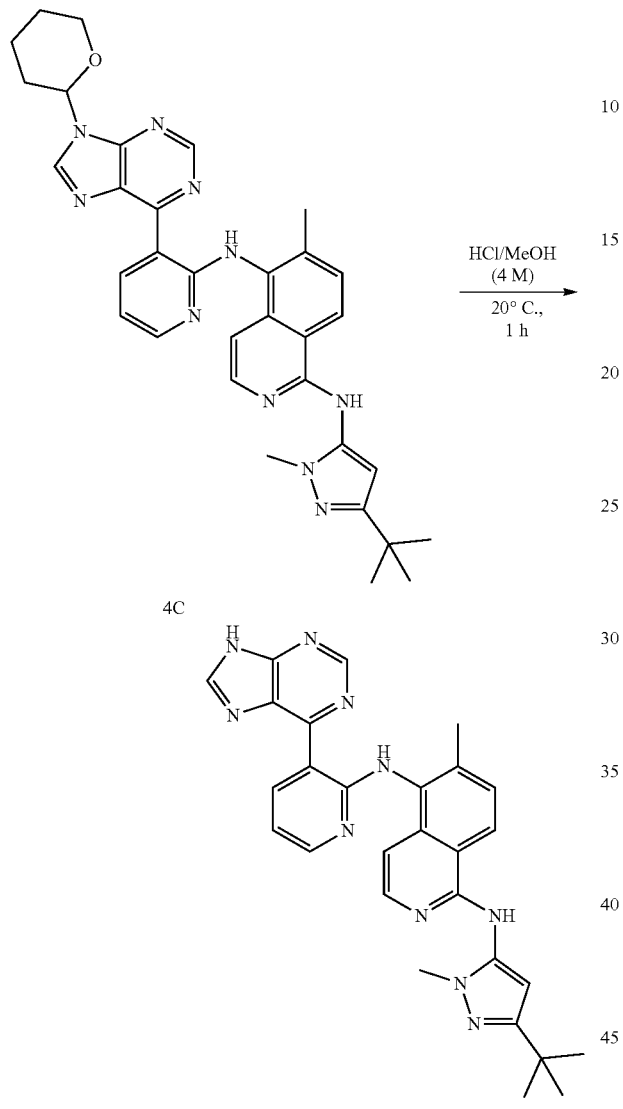

A mixture of compound 4C (250 mg, 425 umol, 1.0 eq) in HCl/MeOH (4 mL, 4M) was stirred for 1 hour at 20° C. TLC (dichloromethane:methanol=10:1, $R_f$=0.24) and LCMS (ET15300-18-P1A, product RT=2.384) showed the starting material was consumed completely. The mixture was concentrated in reduce pressure at 40° C. The pH value was adjusted to 9 with aqueous NaHCO$_3$ and the aqueous phase was poured into ethyl acetate (10 mL). The mixture was stirred for 5 min. The mixture was filtered and the filter cake was washed with 10 mL of H$_2$O, dried in vacuum. The filter liquor was extracted with ethyl acetate (10 mL, 6 mL). The combined organic phase was washed with brine (20 mL), dried with anhydrous Na$_2$SO$_4$, filtered and concentrated in vacuum. The residue was purified by prep-HPLC (column: YMC-Actus Triart C18 100*30 mm*5 um; mobile phase: [water (10 mM NH$_4$HCO$_3$)-ACN]; B %: 40%-60%, 12 min) to afford LUT013 (150 mg, 295 umol, 69.6% yield, 99.4% purity) as yellow solid.

$^1$H NMR: ET15300-18-P1A 400 MHz DMSO-d$_6$

δ 13.83 (br. s, 1H), 11.80 (s, 1H), 9.71 (s, 1H), 9.09 (s, 1H), 9.05 (s, 1H), 8.73 (s, 1H), 8.26 (d, J=8.8 Hz, 1H), 8.04 (d, J=2.8 Hz, 1H), 7.80 (d, J=2.0 Hz, 1H), 7.57 (d, J=8.4 Hz, 1H), 7.08 (d, J=6.0 Hz, 1H), 6.89-6.92 (m, 1H), 6.05 (s, 1H), 3.54 (s, 3H), 2.36 (s, 3H), 1.26 (s, 9H).

Example 3

Synthesis of Compound of Formula I, R=3-(trifluoromethoxy)phenyl (LUT014)—Laboratory Scale Process Preparation of Intermediate 3D-2

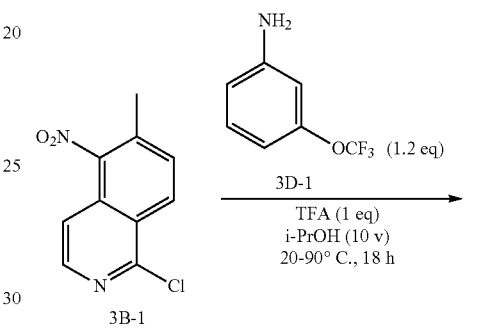

To a mixture of compound 3B-1 (2.00 g, 8.98 mmol, 1.0 eq) and compound 3D-1 (1.91 g, 10.8 mmol, 1.2 eq) in isopropanol (20 mL) was added TFA (1.02 g, 8.98 mmol, 1.0 eq) in one portion at 20° C. under nitrogen. The mixture was stirred at 90° C. for 18 hours. LC-MS (ET15060-21-P1A1) showed the reaction was completed. The resulting suspension was cooled and the product was filtered off, washing with a small volume of dichloromethane (10 mL) to give compound 3D-2 (3.00 g, 8.26 mmol, 91.9% yield) as yellow solid which was used for next step directly.

$^1$H NMR: ET15060-21-P1A1 400 MHz DMSO-d$_6$ 9.68 (s, 1H), 8.71 (d, J=8.8 Hz, 1H), 8.15 (d, J=6.0 Hz, 1H), 8.03 (s, 1H), 7.91 (dd, J=8.4, 1.2 Hz, 1H), 7.71 (d, J=8.4, Hz, 1H), 7.45 (t, J=8.4 Hz, 1H), 6.98 (d, J=8.0 Hz, 1H), 6.90 (d, J=6.0 Hz, 1H), 2.48 (s, 3H).

Preparation of Intermediate 3D

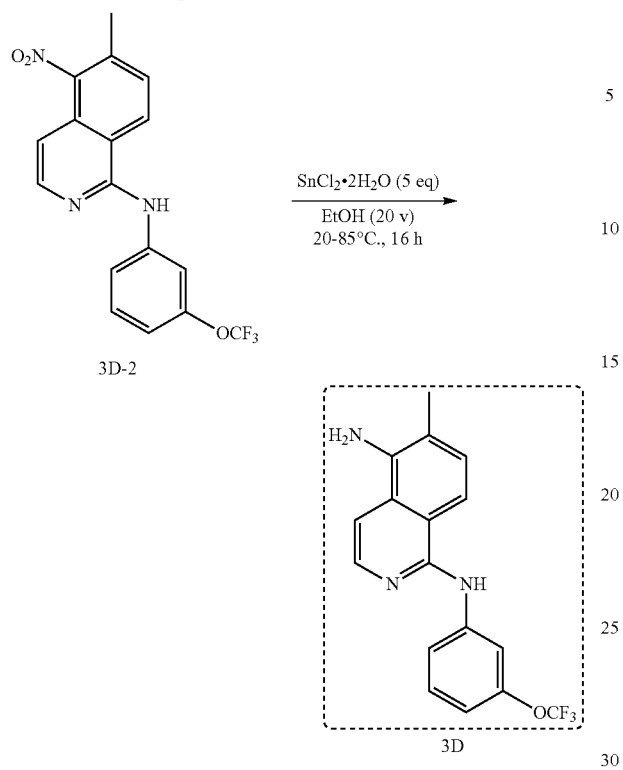

To a mixture of compound 3D-2 (3.00 g, 8.26 mmol, 1.0 eq) in ethanol (30 mL) was added SnCl$_2$.2H$_2$O (9.32 g, 41.3 mmol, 5.0 eq) in one portion at 20° C. under nitrogen. The mixture was stirred at 85° C. for 16 hours. LC-MS (ET15060-24-P1A) showed the reaction was completed. The dark solution was concentrated, diluted with DCM (30 mL), washed with aq. NaOH (1.30 mol/L, 40 mL). The mixture was stirred for 10 min and filtered. The filter was separated and the aqueous phase was extracted with DCM (20 mL). The combined organic phase was washed with brine (30 mL), dried with anhydrous Na$_2$SO$_4$, filtered and concentrated in vacuum to give compound 3D (2.20 g, 6.60 mmol, 79.9% yield) as a red solid which was used for next step directly without further purification.

$^1$H NMR: ET15060-24-P1A1 400 MHz DMSO-d$_6$ 9.14 (s, 1H), 8.13 (s, 1H), 7.92-7.99 (m, 2H), 7.66 (d, J=8.4 Hz, 1H), 7.50 (d, J=6.0, Hz, 1H), 7.39 (t, J=8.4, Hz, 1H), 7.29 (s, J=8.4, 1H), 6.88 (d, J=7.6, 1H), 5.53 (d, 2H), 2.28 (s, 3H).

Preparation of Intermediate 4D

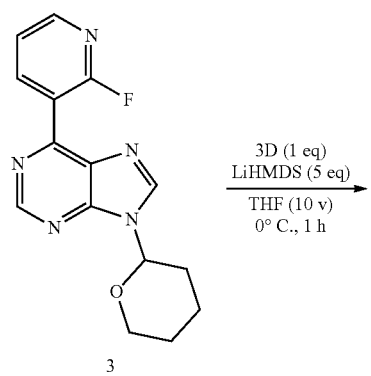

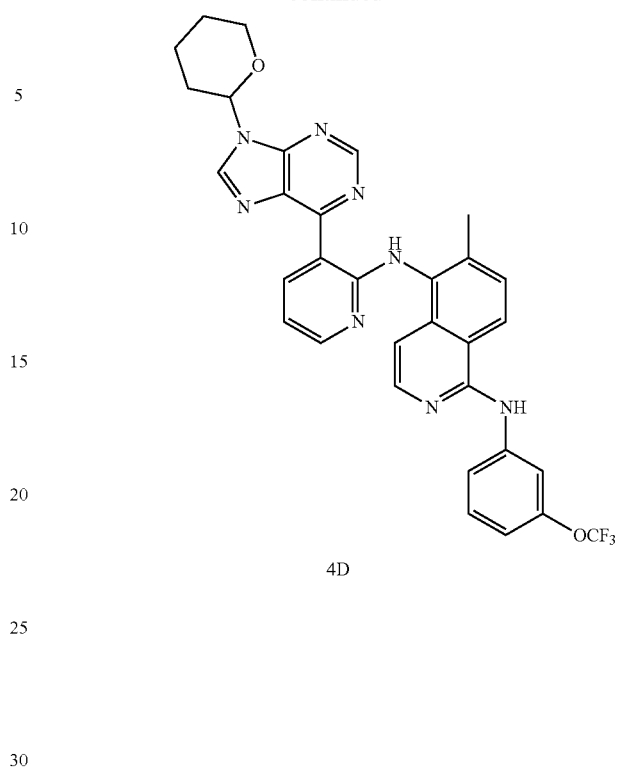

To a mixture of compound 3 (850 mg, 2.84 mmol, 1.0 eq) and compound 3D (947 mg, 2.84 mmol, 1.0 eq) in tetrahydrofuran (8.50 mL) was added drop wise LiHMDS (1M, 14.2 mL, 5.0 eq) at 0° C. under nitrogen. The mixture was stirred at 0° C. for 1 hour. TLC (petroleum ether/ethyl acetate=1/1, R$_f$=0.48) showed the reaction was completed. The deep red reaction mixture was quenched with drop wise addition of water (1 mL—ice bath cooling) resulting in a light orange solution containing a white solid in suspension. The mixture was concentrated to a give yellow solid which was suspended in ethyl acetate (80 mL), dried (MgSO$_4$) and filtered through a plug of Celite to give a yellow solution and concentrated in vacuum. The residue was suspended in MTBE (15 mL) and stirred for 12 hours. The mixture was filtered and the filter cake was dried in vacuum to give compound 4D (1.50 g, 2.45 mmol, 86.2% yield) as yellow solid.

$^1$H NMR: ET15060-38-p1a1 400 MHz DMSO-d$_6$ 11.77 (s, 1H), 9.75 (d, J=6.4 Hz, 1H), 9.64 (s, 1H), 9.19 (s, 1H), 9.06 (s, 1H), 8.54 (d, J=8.4 Hz, 1H), 8.20 (s, 1H), 8.13 (dd, J=4.4, 1.6 Hz, 1H), 8.03 (d, J=6.0 Hz, 2H), 7.69 (d, J=8.8 Hz, 1H), 7.49 (t, J=8.0 Hz, 1H), 7.26 (d, J=6.0 Hz, 1H), 6.99 (dd, J=8.0, 4.4 Hz, 2H), 5.97 (d, J=10.0 Hz, 1H), 4.15 (d, J=12.0 Hz, 1H), 3.81-3.88 (m, 1H), 2.40-2.47 (m, 4H), 2.06-2.16 (m, 3H), 1.83-1.86 (m, 1H).

Preparation of Compound of Formula I, R=3-(trifluoromethoxy)phenyl (LUT014)

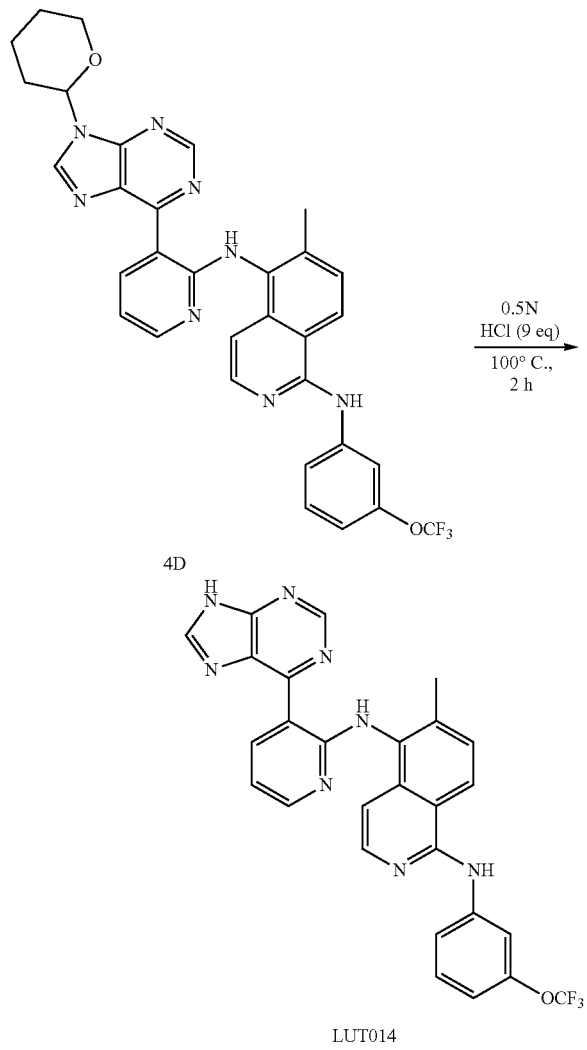

Compound 4D (1.50 g, 2.45 mmol, 1.0 eq) was suspended in aqueous HCl (0.5M, 44.1 mL, 9.0 eq) and heated to 100° C. and stirred for 2 hr. The bulk of the solid dissolved to give a yellow solution. LC-MS (ET15060-42-P1A2) showed the reaction was completed. The hot solution was filtered, washing with boiling water (2×5.0 mL). The resulting solution was cooled in an ice bath and product crystallized from solution as a yellow solid. pH value was adjusted to 9 with Na$_2$CO$_3$ (solid). The mixture was stirred for 10 min and filtered and the filter cake was washed with water (5.0 mL) and collected. The solid was added dichloromethane:methanol (10:1, 15 mL) and stirred for 5 min. The mixture was filtered and the filter cake was collected to give LUT014 (150 mg, 274 umol, 11.2% yield, 96.7% purity) as a yellow solid.

$^1$H NMR: ET15060-42-P1A2 400 MHz DMSO-d$_6$ 13.84 (s, 1H), 11.85 (s, 1H), 9.76 (s, 1H), 9.43 (s, 1H), 9.06 (s, 1H), 8.74 (s, 1H), 8.43 (d, J=8.8 Hz, 1H), 8.12 (s, 1H), 8.05 (dd, J=4.4, 1.6 Hz, 1H), 7.94-7.97 (m, 2H), 7.64 (d, J=8.8 Hz, 1H), 7.43 (t, J=8.4 Hz, 1H), 7.21 (d, J=6.0 Hz, 1H), 6.92 (dd, J=8.0, 4.8 Hz, 2H), 2.38 (s, 3H).

Example 4

Synthesis of Compound of Formula I, R=3-(trifluoromethoxy)phenyl (LUT014 or C17071479-F) by an Improved, Scaled-up Process Example 3 discloses a process for the synthesis of the LUT014 compound at laboratory scale.

An improved, scaled-up synthetic process for the preparation of LUT014 was carried out at multi-Kg scale, in order to validate the improved process at large scale production and provide material for clinical studies. The improved scaled-up process is disclosed in this example.

Figure 6:
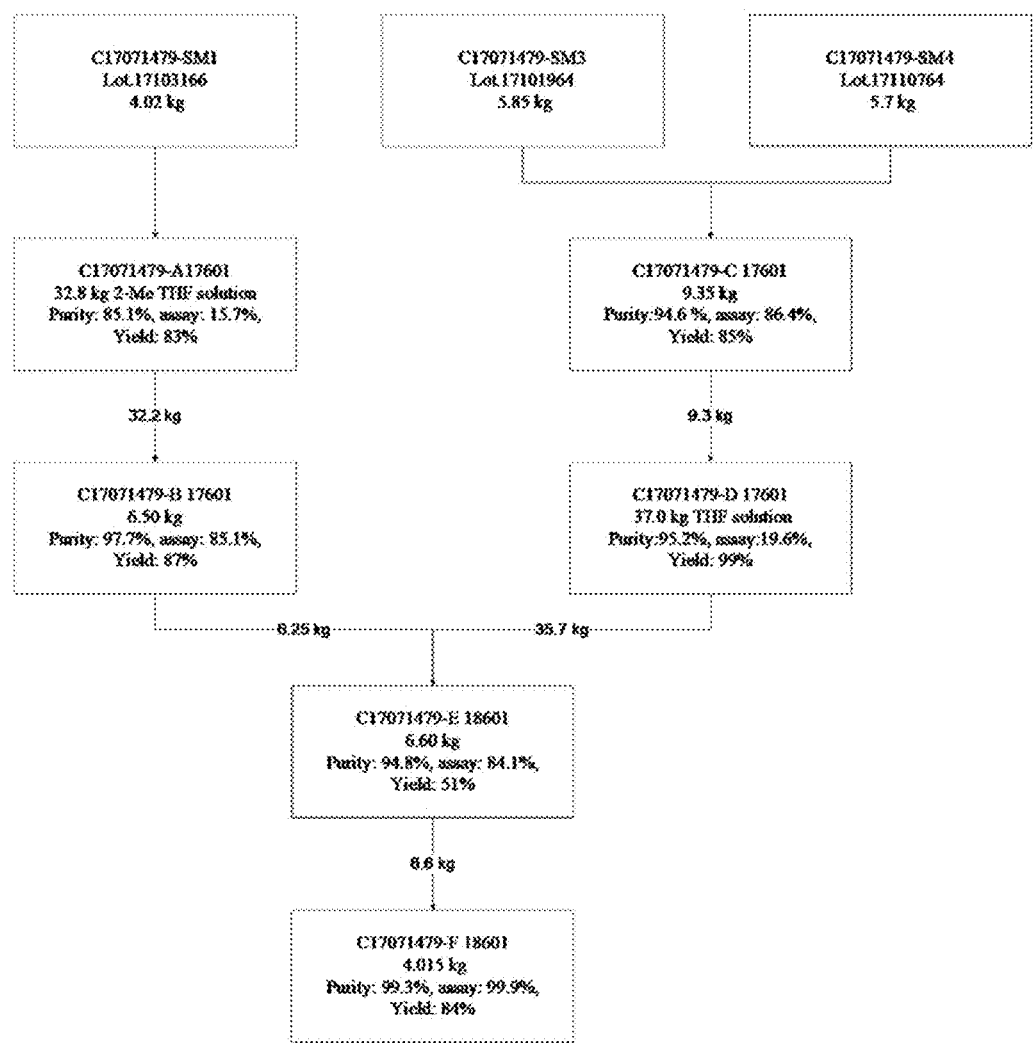
FIG. 6 depicts the flow diagram of the Improved Scaled-Up Synthetic Process for the Preparation of LUT014 (C17071479-F).

The improved scaled-up synthetic process produced 4,015 Kg LUT014, a very large scale-up, as compared to the above laboratory scale process of Example 3, which resulted in 150 mg. The flow diagram in FIG. 6 depicts the improved scaled-up process for the preparation of LUT014 (C17071479-F), its stages, amounts, yields and purities of the intermediates and of the LUT014 (C17071479-F) product.

This Example validates the improved scaled-up synthesis of the LUT014 compound at kilogram scale in a multi-stage process followed by purification by crystallization yielding a purified product of 99.3% purity.

Synthetic Stages of the Improved Scaled-Up Process for the Manufacture of Compound of Formula I, R=3-(trifluoromethoxy)phenyl (LUT014 or C17071479-F)

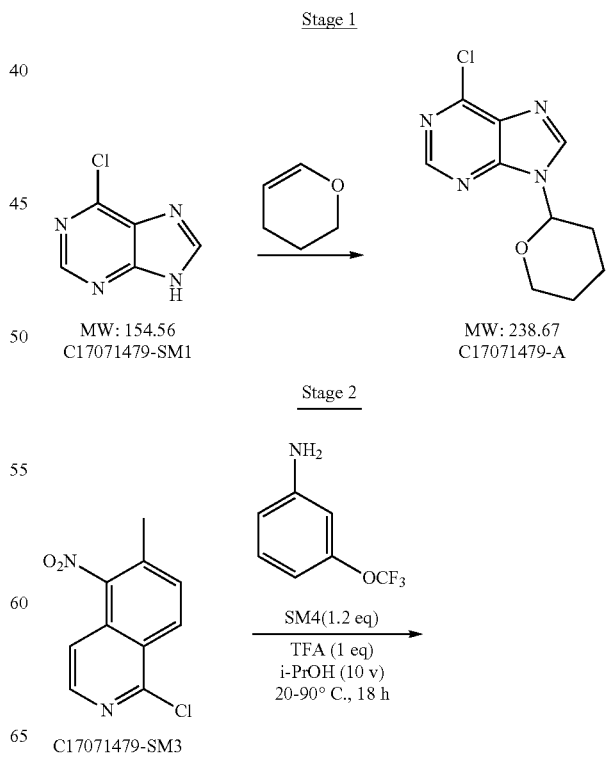

33
-continued
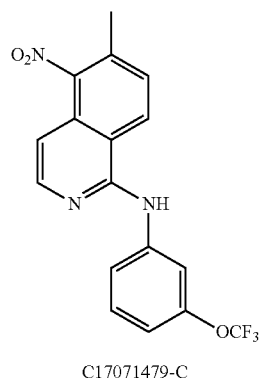
C17071479-C
Stage 3
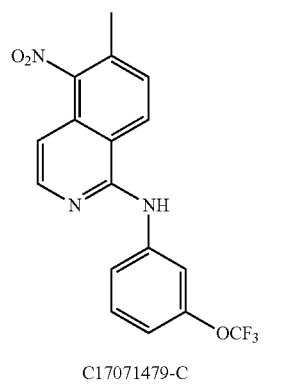
C17071479-C
SnCl₂•2H₂O (5 eq)
───────────────
EtOH(20 v)
20-85° C., 16 h
34
-continued
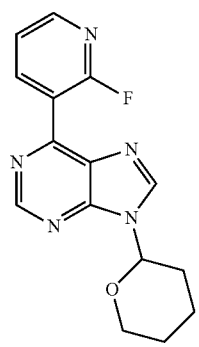
MW: 299.30
C17071479-B
Stage 5
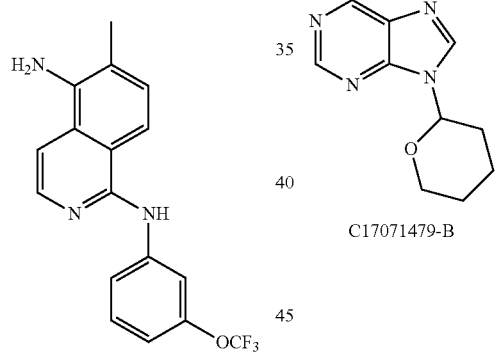
C17071479-B
+
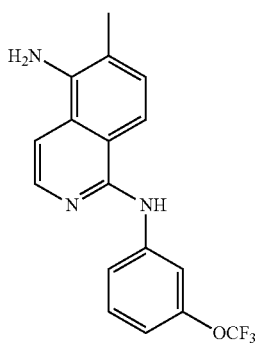
C17071479-D
C17071479-D
Stage 4
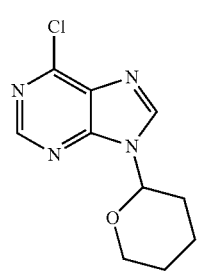
MW: 238.67
C17071479-A
C17071479-SM2
LiHMDS (5 eq)
──────────
THF (10 v)
0° C., 1 h

35
-continued
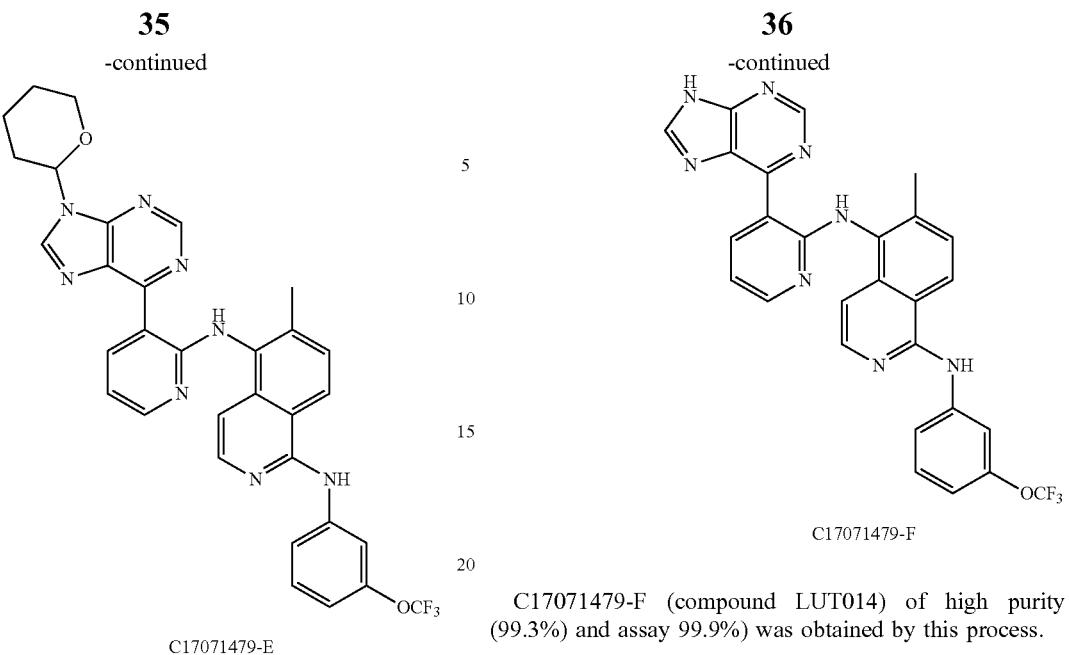
C17071479-E
Stage 6
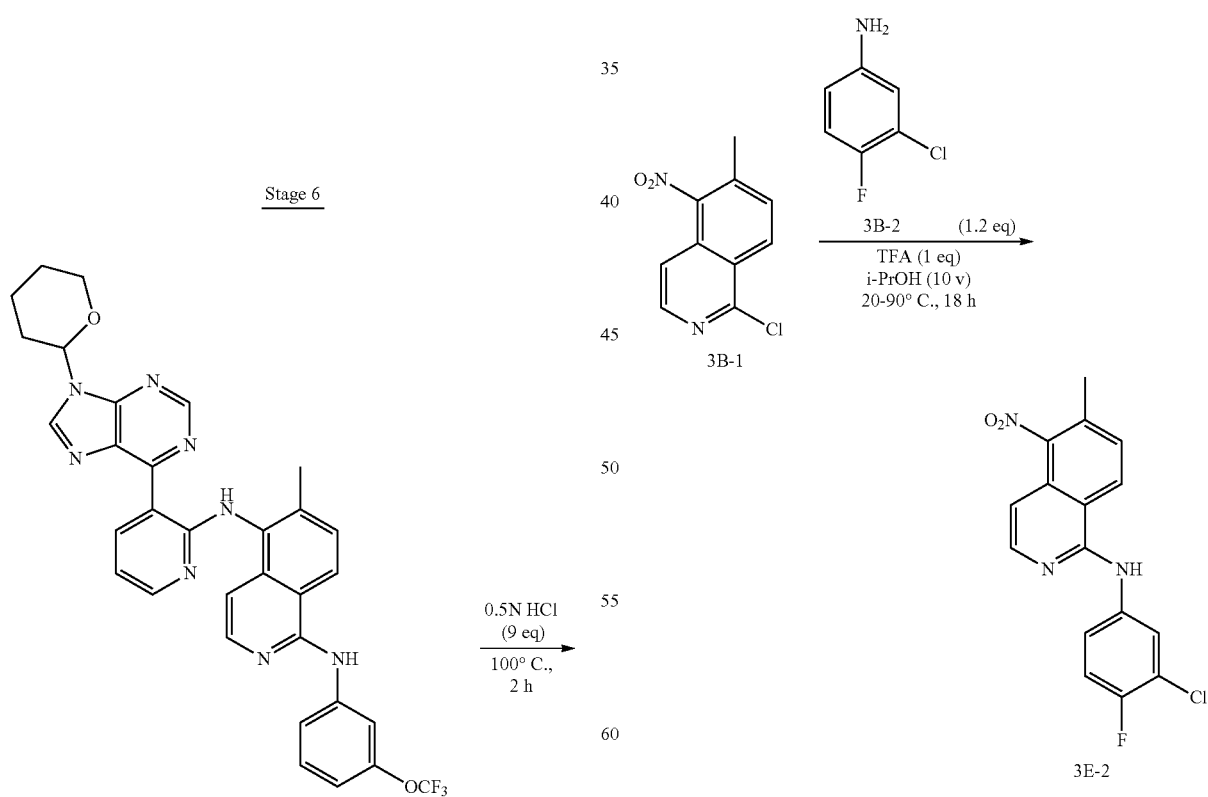
C17071479-E
36
-continued
C17071479-F
C17071479-F (compound LUT014) of high purity (99.3%) and assay 99.9%) was obtained by this process.
Example 5
Synthesis of Compound of Formula I, R=3-chloro-4-fluorophenyl (LUT015)
Preparation of Intermediate 3E-2
To a mixture of compound 3B-1 (2.00 g, 8.98 mmol, 1.0 eq) and compound 3B-2 (1.57 g, 10.8 mmol, 1.2 eq) in isopropanol (20 mL) was added TFA (1.02 g, 8.98 mmol, 1.0 eq) in one portion at 20° C. under nitrogen. The mixture was stirred at 90° C. for 18 hours. TLC (petroleum ether:ethyl acetate=3:1, R$_f$=0.43) showed the reaction was completed. The mixture was cooled and the mixture was filtered. The filter cake was washed with a small volume of dichloromethane (10 mL) to give compound 3E-2 (3.10 g, crude) as yellow solid which was used for next step directly.

$^1$H NMR: ET15060-4-P1A1 400 MHz DMSO-d$_6$
10.75 (br. s, 1H), 8.91 (d, J=8.8 Hz, 1H), 7.96 (dd, J=6.4, 3.2 Hz, 1H), 7.95 (d, J=6.4 Hz, 1H), 7.83 (d, J=8.8, Hz, 1H), 7.72-7.76 (m, 1H), 7.49-7.55 (m, 1H), 6.95 (d, J=6.4 Hz, 1H), 2.50 (s, 3H).

Preparation of Intermediate 3E

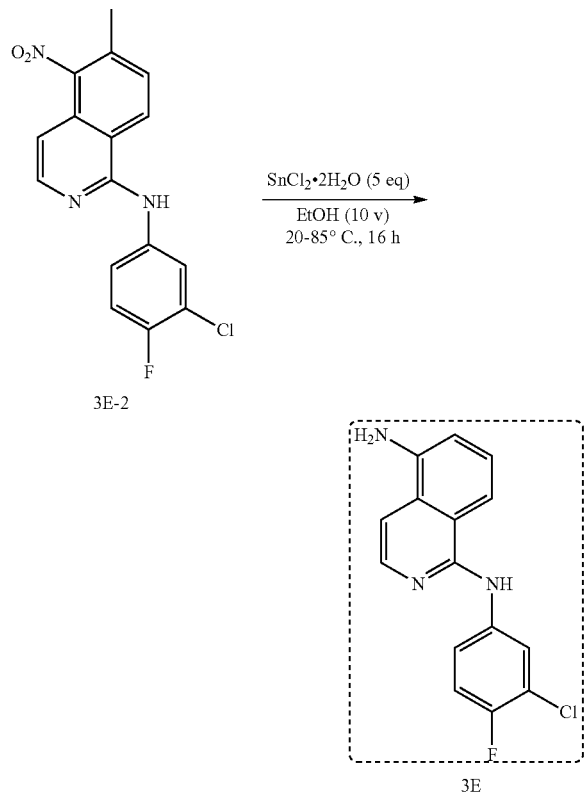

Preparation of Intermediate 4E

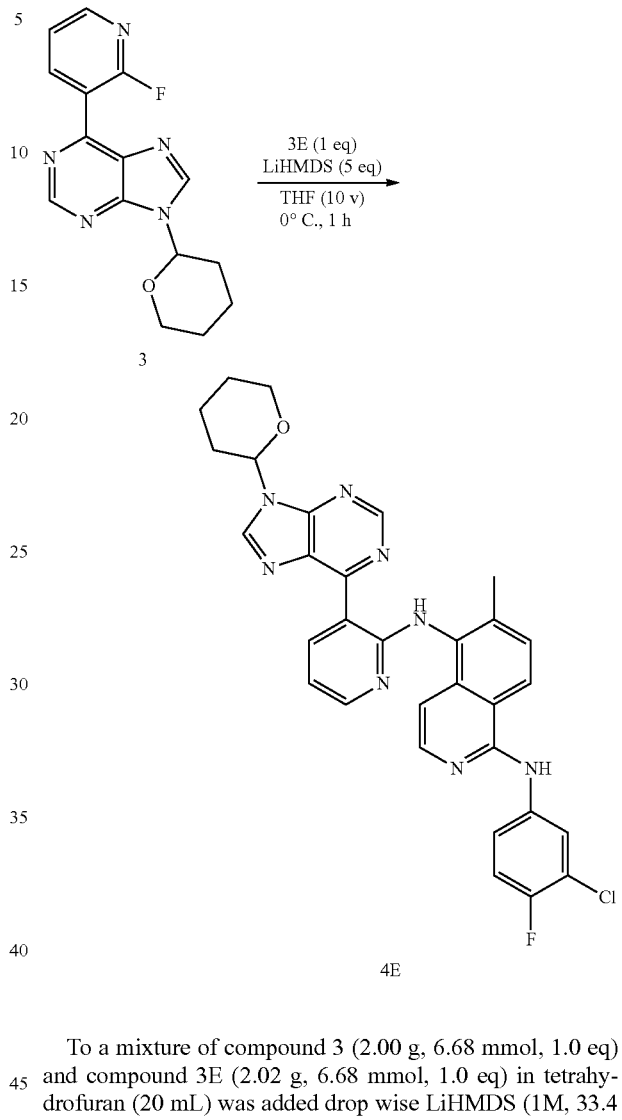

To a mixture of compound 3E-2 (3.10 g, 9.34 mmol, 1.0 eq) in ethanol (30 mL) was added SnCl$_2$.2H$_2$O (10.5 g, 46.7 mmol, 5.0 eq) in one portion at 20° C. under nitrogen. The mixture was stirred at 85° C. for 16 hours. LCMS (ET15060-34-P1A1) showed the reaction was completed. The dark solution was concentrated, diluted with dichloromethane (30 mL), washed with aq. NaOH (1.30 mol/L, 25.0 mL). The mixture was stirred for 10 min and filtered. The organic phase was separated and the aqueous phase was extracted with dichloromethane (20 mL). The combined organic phase was washed with brine (15 mL), dried with anhydrous Na$_2$SO$_4$, filtered and concentrated in vacuum to give compound 3E (2.50 g, 8.29 mmol, 88.7% yield) as a red solid which was used for next step directly without further purification.

$^1$H NMR: ET15060-34-P1A1 400 MHz DMSO-d$_6$
9.01 (s, 1H), 8.26 (dd, J=6.8, 2.4 Hz, 1H), 7.89 (d, J=6.0 Hz, 1H), 7.81-7.87 (m, 1H), 7.61 (d, J=8.4 Hz, 1H), 7.45 (d, J=6.0, Hz, 1H), 7.30 (t, J=8.8 Hz, 1H), 7.27 (d, J=8.4 Hz, 1H), 5.50 (s, 2H), 2.32 (s, 3H).

To a mixture of compound 3 (2.00 g, 6.68 mmol, 1.0 eq) and compound 3E (2.02 g, 6.68 mmol, 1.0 eq) in tetrahydrofuran (20 mL) was added drop wise LiHMDS (1M, 33.4 mL, 5.0 eq) at 0° C. under nitrogen. The mixture was stirred at 0° C. for 1 hour. TLC (petroleum ether:ethyl acetate, R$_f$=0.43) showed the reaction was completed. The deep red reaction mixture was quenched with drop wise addition of water (2 mL—ice bath cooling) resulting in a light orange solution containing a white solid in suspension. The mixture was concentrated to a give yellow solid which was suspended in ethyl acetate (200 mL), dried (MgSO$_4$) and filtered through a plug of Celite to give a yellow solution and concentrated in vacuum. The residue was suspended in MTBE (30.0 mL) and stirred for 12 h. The mixture was filtered and the filter cake was dried in vacuum to give compound 4E (2.00 g, 3.44 mmol, 51.5% yield) as a yellow solid.

$^1$H NMR: ET15060-39-P1A1 400 MHz DMSO-d$_6$
11.69 (s, 1H), 9.68 (d, J=1.6 Hz, 1H), 9.66 (s, 1H), 9.12 (s, 1H), 9.11 (s, 1H), 8.44 (d, J=8.8 Hz, 1H), 8.30 (d, J=6.8 Hz, 1H), 8.07 (d, J=2.8 Hz, 1H), 7.93-7.95 (m, 2H), 7.61-7.63 (m, 1H), 7.49 (t, J=8.0 Hz, 1H), 7.37 (t, J=1.2 Hz, 1H), 7.16 (d, J=6.0 Hz, 1H), 6.93 (d, J=4.8 Hz, 1H), 5.91 (d, J=9.2 Hz,

1H), 4.04-4.06 (m, 1H), 3.77 (t, J=12.0 Hz, 1H), 2.34-2.41 (m, 6H), 2.02-2.10 (m, 3H), 1.76-1.79 (m, 1H).

Preparation of Compound of Formula I, R=3-chloro-4-fluorophenyl (LUT015)

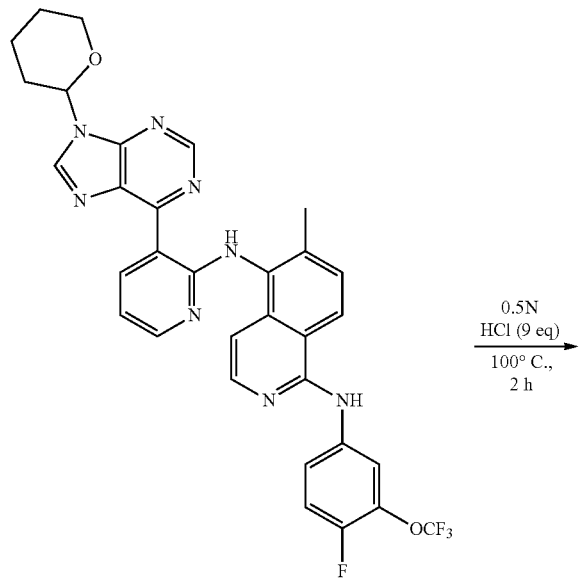

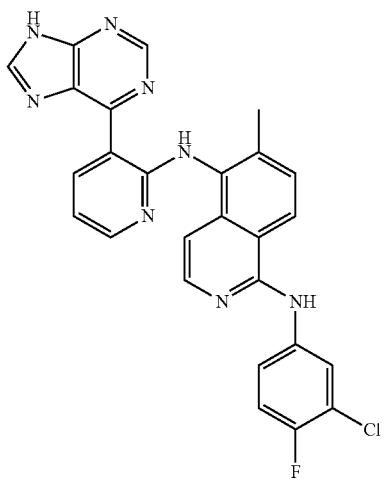

LUT015

Compound 4E (2.00 g, 3.44 mmol, 1.0 eq) was suspended in aqueous HCl (0.5M, 62.0 mL, 9.0 eq) and heated to 100° C. and stirred for 2 hrs. The bulk of the solid dissolved to give a yellow solution. LCMS (ET15060-43-P1A2) showed the reaction was completed. The hot solution was filtered, washing with boiling water (2×10 mL). pH value was adjusted to 9 with $Na_2CO_3$ (solid). The mixture was filtered and the filter cake was purified by prep-TLC (petroleum ether:ethyl acetate=0:1, $R_f$=0.46) to give LUT015 (170 mg, 332 umol, 9.64% yield, 97.0% purity) as a yellow solid.

$^1$H NMR: ET15060-43-P1A1 400 MHz DMSO-$d_6$ 13.84 (s, 1H), 11.84 (s, 1H), 9.75 (s, 1H), 9.34 (s, 1H), 9.06 (s, 1H), 8.74 (s, 1H), 8.39 (d, J=8.4 Hz, 1H), 8.28 (dd, J=6.8, 2.8 Hz, 1H), 8.05 (dd, J=4.4, 1.6 Hz, 1H), 7.94 (d, J=6.0 Hz, 1H), 7.85-7.88 (m, 1H), 7.63 (d, J=8.8 Hz, 1H), 7.38 (t, J=9.2 Hz, 1H), 7.18 (d, J=6.0 Hz, 1H), 6.92 (dd, J=8.0, 4.8 Hz, 1H), 2.38 (s, 3H).

Example 6

Synthesis of Compound of Formula I, R=2-fluoro-4-iodophenyl (LUT016)

Preparation of Intermediate 3F-2

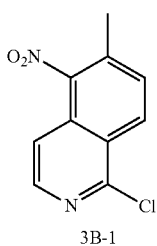

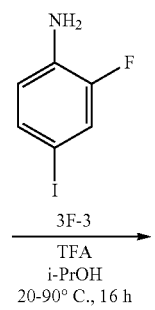

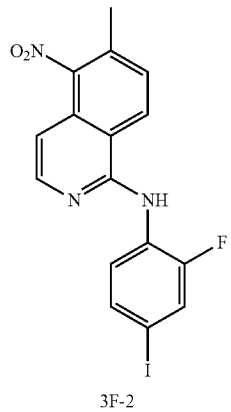

To a mixture of compound 3B-1 (2.00 g, 8.98 mmol, 1.0 eq) in isopropanol (20 mL) was added compound 3F-3 (2.55 g, 10.8 mmol, 1.2 eq) and trifluoroacetic acid (1.02 g, 8.98 mmol, 665 uL, 1.0 eq) at 20° C. under nitrogen. The resulting mixture was heated to 90° C. and stirred at 90° C. for 16 h. TLC (petroleum ether:ethyl acetate=3:1, $R_{f\text{-}SM}$=0.43, $R_{f\text{-}DP}$=0.24) showed the reaction was completed. The reaction mixture was filtered and filter cake was washed with dichloromethane (10 mL), the filter cake was collected and dried in vacuum to afford compound 3F-2 (2.80 g, 6.62 mmol, 73.7% yield) as a light-yellow solid, which was used for next step without further purification.

$^1$H NMR: ET15201-2-P1A 400 MHz MeOD δ 8.71 (d, J=8.8 Hz, 1H), 7.91-7.95 (m, 2H), 7.84 (d, J=8.4 Hz, 1H), 7.74 (d, J=7.2 Hz, 1H), 7.41 (t, J=8.0 Hz, 1H), 7.18 (d, J=7.2 Hz, 1H), 2.62 (s, 3H).

Preparation of Intermediate 3F

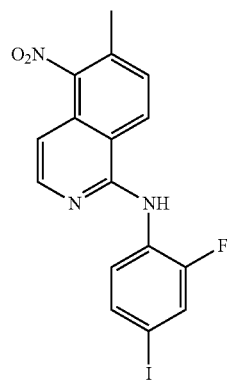

3F-2

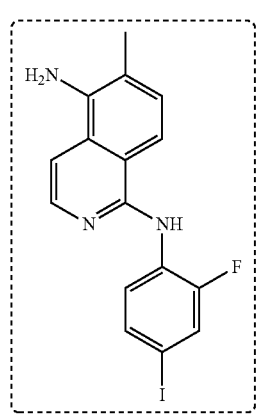

3F

Preparation of Intermediate 3F

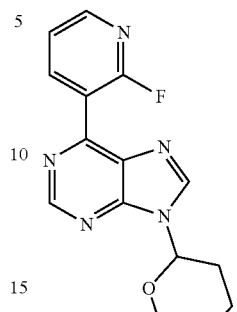

3

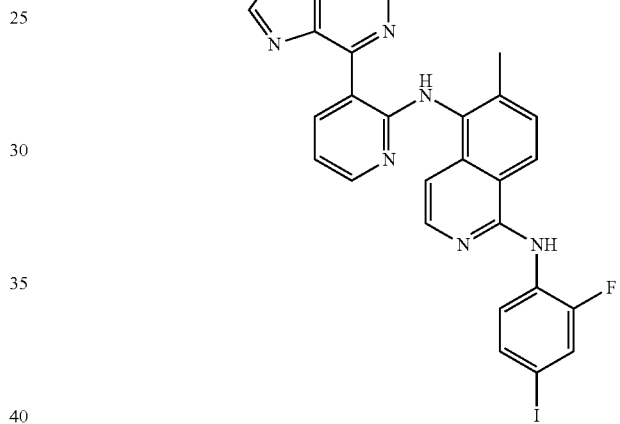

4F

To a mixture of compound 3F-2 (2.80 g, 6.62 mmol, 1.0 eq) in ethanol (28 mL) was added SnCl$_2$·2H$_2$O (7.47 g, 33.1 mmol, 5.0 eq) at 20° C. under nitrogen. The resulting mixture was heated to 85° C. and stirred at 85° C. for 16 h. TLC (petroleum ether:ethyl acetate=2:1, R$_{f\text{-}SM}$=0.43, R$_{f\text{-}DP}$=0.30) showed the reaction was completed. The reaction mixture was cooled to 20° C. and poured to 5 N NaOH aqueous (20 mL) and stirred for 3 min, filtered and the filtrate was extracted with dichloromethane (20 mL, 15 mL). The combined organic phase was dried with anhydrous Na$_2$SO$_4$, filtered and concentrated in vacuum to afford compound 3F (2.20 g, crude) as red solid, which was used for next step without further purification.

$^1$H NMR: ET15201-6-P1A 400 MHz DMSO-$_{d6}$

δ 7.74 (d, J=6.4 Hz, 1H), 7.61 (dd, J=8.0, 2.4 Hz, 1H), 7.44-7.52 (m, 3H), 7.37 (d, J=6.8 Hz, 1H), 7.21 (d, J=6.8 Hz, 1H), 5.47 (s, 2H), 2.25 (s, 3H).

To a mixture of compound 3 (1.00 g, 3.34 mmol, 1.0 eq) and compound 3F (1.31 g, 3.34 mmol, 1.0 eq) in tetrahydrofuran (10 mL) was added LiHMDS (1M, 16.7 mL, 5.0 eq) at 0° C. under nitrogen. The resulting mixture was stirred at 0° C. for 1 h. TLC (petroleum ether:ethyl acetate=2:1, R$_{f\text{-}SM}$=0.25, R$_{f\text{-}DP}$=0.40) showed the reaction was completed. The reaction mixture was quenched with dropwise addition of ice-water (2 mL) at 0° C. while resulting in a light orange solution containing a white solid in suspension. The mixture was concentrated to give a yellow solid which was suspended in ethyl acetate (50 mL), dried with Na$_2$SO$_4$, filtered through a plug of Celite to give a yellow solution and was concentrated in vacuum. The residue was washed with methyl tert-butyl ether (20 mL), filtered to afford the filter cake and filter cake was dried in vacuum to give compound 4F (1.10 g, 1.64 mmol, 49.0% yield) as a light-yellow solid.

$^1$H NMR: ET15201-10-P1A1 400 MHz DMSO-$_{d6}$

δ 11.68 (s, 1H), 9.63-9.67 (m, 1H), 9.08-9.12 (m, 2H), 8.98 (s, 1H), 8.30 (d, J=8.8 Hz, 1H), 8.05-8.06 (m, 1H), 7.79 (d, J=6.0 Hz, 1H), 7.66 (dd, J=8.2, 2.0 Hz, 1H), 7.54-7.60 (m, 2H), 7.44-7.46 (m, 2H), 7.11 (d, J=6.0 Hz, 1H), 6.91 (q, J=4.4 Hz, 1H), 5.89 (d, J=11.2 Hz, 1H), 4.07 (d, J=12.8 Hz,

1H), 3.74-3.80 (m, 1H), 2.36 (s, 3H), 2.05 (t, J=13.6 Hz, 2H), 1.63-1.68 (m, 3H), 1.11 (s, 2H).

Preparation of Compound of Formula I, R=2-fluoro-4-iodophenyl (LUT016)

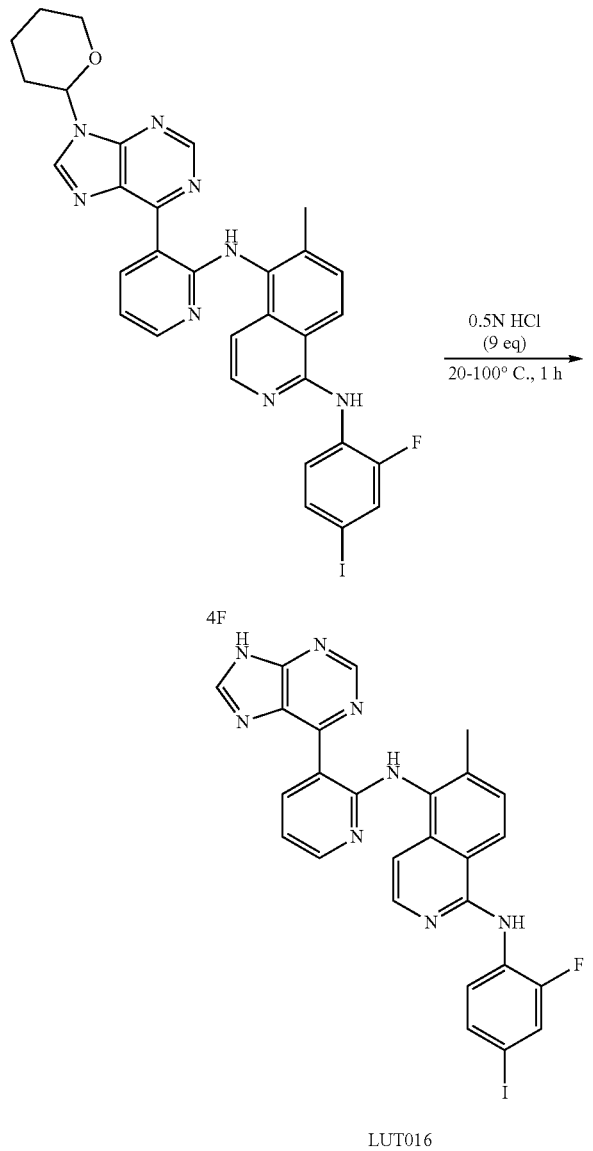

Compound 4F (1.10 g, 1.64 mmol, 1.0 eq) was suspended in HCl (0.5M, 29 mL, 9.0 eq) at 20° C. under nitrogen. The mixture was heated to 100° C. and stirred at 100° C. for 1 h. LCMS (ET15201-12-P1A1) showed the reaction was completed. The hot solution was filtered, washing with boiling water (2×20 mL). The resulting solution was cooled in an ice bath and product was crystallized from solution as a yellow solid. The solid was filtered and added to saturated aq. NaCO$_3$ (100 mL). The mixture was stirred for 10 min and filtered, the filtered cake was washed with water (50 mL) and collected as crude product. The crude product was purified by prep-HPLC (column: Waters Xbridge 150*25 5u; mobile phase: [water (10 mM NH4HCO$_3$)-ACN]; B %: 50%-80%, 11 min) to afford LUT016 (125 mg, 212 umol, 12.9% yield, 99.6% purity) as a yellow solid $^1$HNMR: ET15201-12-P1A1 400 MHz DMSO-$_{d6}$ δ 13.81 (s, 1H), 11.79 (s, 1H), 9.71 (s, 1H), 9.04 (s, 2H), 8.72 (s, 1H), 8.24 (d, J=8.4 Hz, 1H), 8.04 (q, J=2.0 Hz, 1H), 7.78 (d, J=6.0 Hz, 1H), 7.65 (d, J=9.6 Hz, 1H), 7.57 (q, J=8.4 Hz, 2H), 7.44 (t, J=8.4 Hz, 1H), 7.11 (d, J=6.0 Hz, 1H), 6.90 (d, J=4.8 Hz, J=2.8 Hz, 1H), 2.36 (s, 3H).

Example 7

Synthesis of Compound of Formula I, R=4-chloro-3-(trifluoromethyl)phenyl (LUT017)

Preparation of Intermediate 3G-2

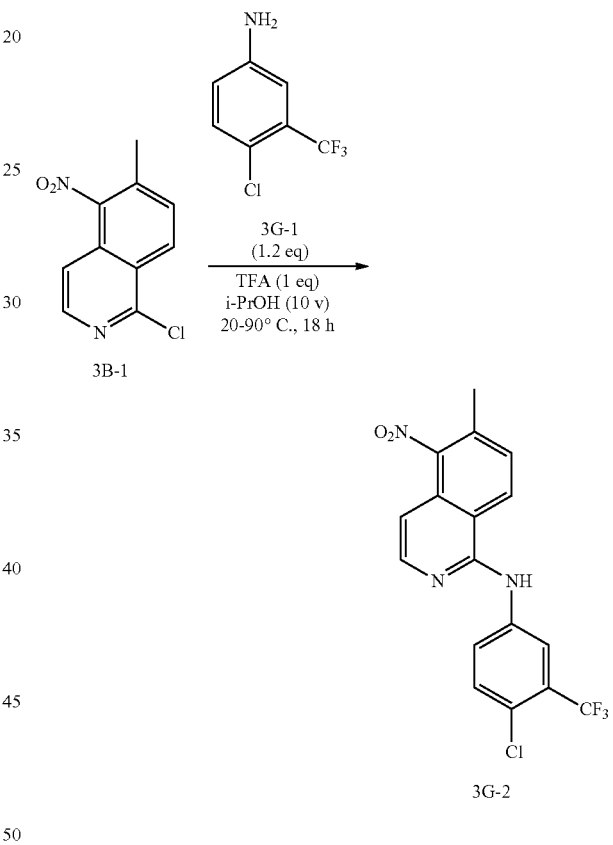

To a mixture of compound 3B-1 (2.00 g, 8.98 mmol, 1.0 eq) and compound 3G-1 (2.11 g, 10.8 mmol, 1.2 eq) in isopropanol (20 mL) was added TFA (1.02 g, 8.98 mmol, 1.0 eq) in one portion at 20° C. under nitrogen. The mixture was stirred at 90° C. for 18 hours. LCMS (ET15060-19-P1A1) showed the reaction was completed. The mixture was cooled to 20° C. and the mixture was filtered. The filter cake was washed with dichloromethane (10 mL) and collected as product (3.20 g, 8.38 mmol, 93.3% yield) as a white solid which was used for next step directly without further purification.

$^1$H NMR: ET15060-3-P1A1 400 MHz DMSO-d$_6$ 10.21 (s, 1H), 8.81 (d, J=8.8 Hz, 1H), 8.42 (dd, J=2.4 Hz, 1H), 8.28 (d, J=2.0 Hz, 1H), 8.26 (d, J=2.0 Hz, 1H), 8.12 (d, J=6.0 Hz, 1H), 7.79 (d, J=8.8 Hz, 1H), 7.73 (d, J=8.8 Hz, 1H), 6.98 (d, J=6.0 Hz, 1H), 2.50 (s, 3H).

Preparation of Intermediate 3G

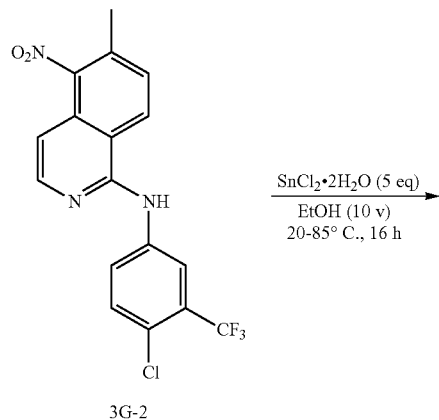

Preparation of Intermediate 4G

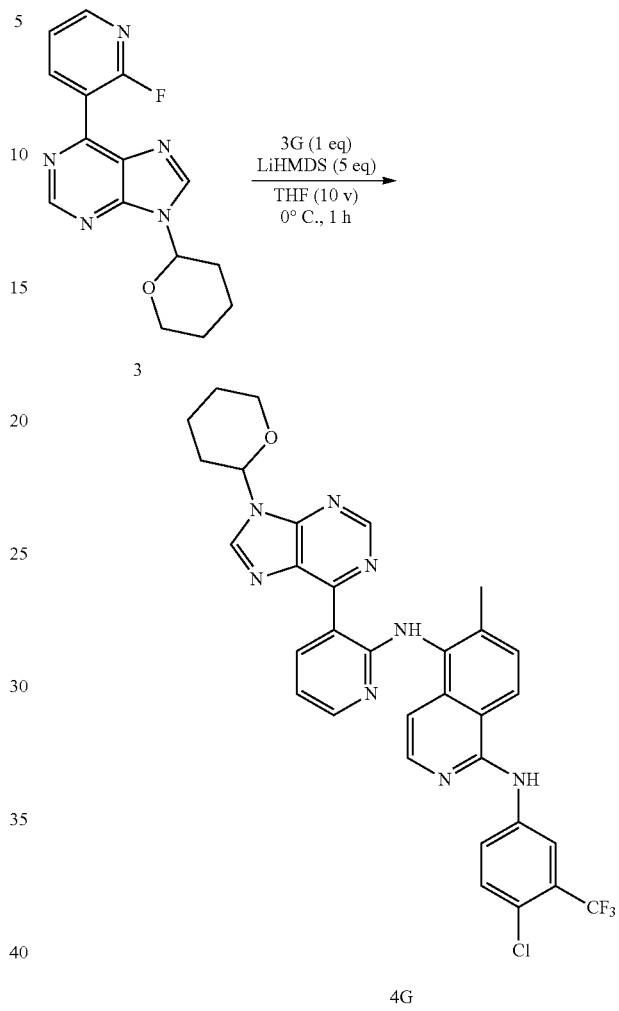

To a mixture of compound 3G-2 (3.20 g, 8.38 mmol, 1.0 eq) in ethanol (30 mL) was added SnCl$_2$·2H$_2$O (9.46 g, 41.9 mmol, 5.0 eq) in one portion at 20° C. under nitrogen. The mixture was stirred at 85° C. for 16 hours. LCMS (ET15060-22-P1A) showed the reaction was completed. The dark solution was concentrated, diluted with dichloromethane (50 mL), washed with aq. NaOH (1.30 mol/L, 50 mL). The mixture was stirred for 10 min and filtered. The filter was separated and the aqueous phase was extracted with dichloromethane (20 mL). The combined organic phase was washed with brine (30 mL), dried with anhydrous Na$_2$SO$_4$, filtered and concentrated in vacuum to give compound 3G (2.50 g, 7.11 mmol, 84.8% yield) as a yellow solid.

$^1$H NMR: ET15060-22-p1a1 400 MHz DMSO-d$_6$ 9.34 (s, 1H), 8.58 (d, J=8.8, 1H), 8.37 (d, J=8.8 Hz, 1H), 7.99 (d, J=6.0 Hz, 1H), 7.65-7.70 (m, 1H), 7.57 (d, J=6.0 Hz, 1H), 7.35 (d, J=8.4, 1H), 5.60 (s, 2H), 2.30 (s, 3H).

To a mixture of compound 3 (2.00 g, 6.68 mmol, 1.0 eq) and compound 3G (2.35 g, 6.68 mmol, 1.0 eq) in tetrahydrofuran (20 mL) was added drop wise LiHMDS (1M, 33.4 mL, 5 eq) at 0° C. under nitrogen. The mixture was stirred at 0° C. for 1 hour. TLC (petroleum ether:ethyl acetate=1:1, R$_f$=0.45) showed the reaction was completed. The deep red reaction mixture was quenched with drop wise addition of ice-water (3 mL) resulting in a light orange solution containing a white solid in suspension. The mixture was concentrated to a give yellow solid which was suspended in ethyl acetate (150 mL), dried (MgSO$_4$) and filtered through a plug of Celite to give a yellow solution and concentrated in vacuum. The residue was suspended in MTBE (150 mL) and stirred for 12 hrs. The mixture was filtered and the filter cake was dried in vacuum to give compound 4G (1.50 g, 1.47 mmol, 22.1% yield, 62.0% purity) as a red solid. (LCMS:ET15060-32-P1A1)

$^1$H NMR: ET15060-32-P1A1 400 MHz DMSO-d$_6$ 11.69 (s, 1H), 9.66 (d, J=2.0 Hz, 1H), 9.64 (s, 1H), 9.10 (s, 1H), 8.96 (s, 1H), 8.50 (d, J=2.4 Hz, 1H), 8.33-8.41 (m, 2H), 8.05 (d, J=2.8 Hz, 1H), 7.96 (d, J=6.0 Hz, 1H), 7.62-7.64 (m, 2H), 7.20-7.22 (m, 1H), 6.94 (d, J=4.8 Hz, 1H), 5.88 (d,

J=10.8 Hz, 1H), 4.03-4.06 (m, 1H), 3.73-3.79 (m, 1H), 2.37 (s, 3H), 1.99-2.07 (m, 2H), 1.62-1.80 (m, 3H).

Preparation of Compound of Formula I,
R=4-chloro-3-(trifluoromethyl)phenyl (LUT017)

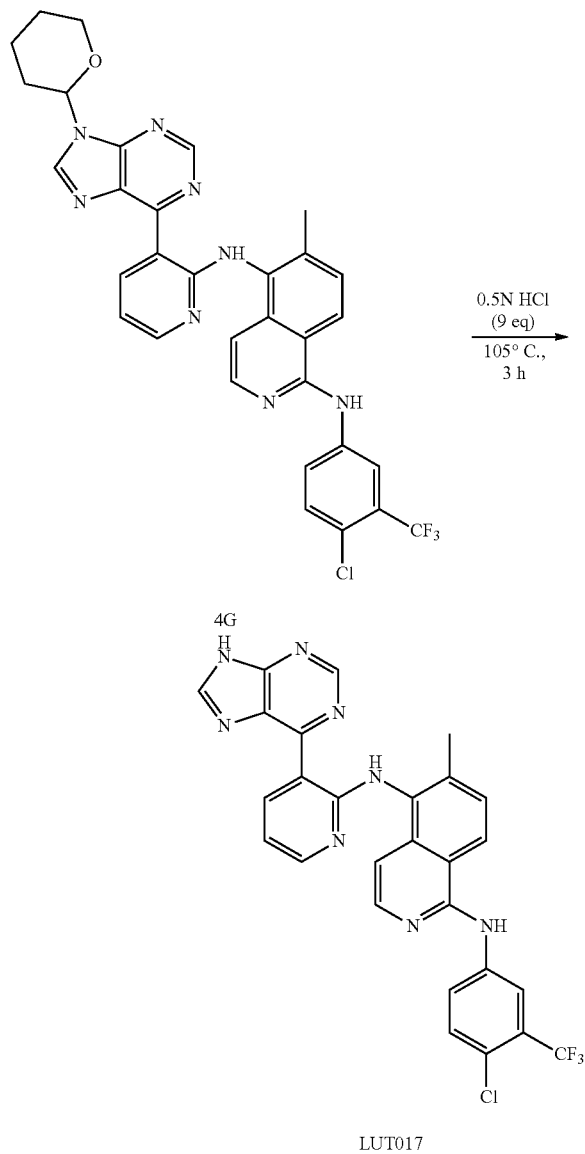

LUT017

Compound 4G (1.50 g, 2.38 mmol, 1.0 eq) was suspended in aqueous HCl (0.5M, 28.5 mL, 6.0 eq) and heated to 100° C. and stirred for 2 hrs. The bulk of the solid dissolved to give a yellow solution. LCMS (ET15060-36-P1A2) showed the reaction was completed. The hot solution was filtered, washing with boiling water (2×10 mL). pH value was adjusted to 9 with $Na_2CO_3$ (solid). The mixture was filtered and the filter cake was purified by prep-TLC (petroleum ether:ethyl acetate=0:1, $R_f$=0.65) to give 0.3 g solid. The solid was purified by prep-HPLC (column: YMC-Actus Triart C18 100*30 mm*5 um; liquid phase: [A-10 mM $NH_4HCO_3$ in $H_2O$; B-ACN]B %: 50%-95%, 12 min]) to give LUT017 (150 mg, 269 umol, 11.3% yield, 98.0% purity) as a yellow solid.

$^1$H NMR: ET15060-36-P1A1 400 MHz DMSO-$d_6$ 13.84 (br. s, 1H), 11.83 (br. s, 1H), 9.73 (s, 1H), 9.60 (s, 1H), 9.06 (s, 1H), 8.74 (s, 1H), 8.52 (d, J=2.4 Hz, 1H), 8.42 (d, J=8.8 Hz, 1H), 8.36 (d, J=2.4 Hz, 1H), 8.05 (dd, J=4.8, 1.2 Hz, 1H), 7.98 (d, J=6.0 Hz, 1H), 7.66 (dd, J=8.8, 2.8 Hz, 1H), 7.23 (d, J=6.0 Hz, 1H), 6.92 (dd, J=7.6, 4.8 Hz, 2H), 2.39 (s, 3H).

Example 8

Synthesis of Compound of Formula I,
R=3,5-dihydroxyphenyl (LUT019)

Preparation of Intermediate 3H-2

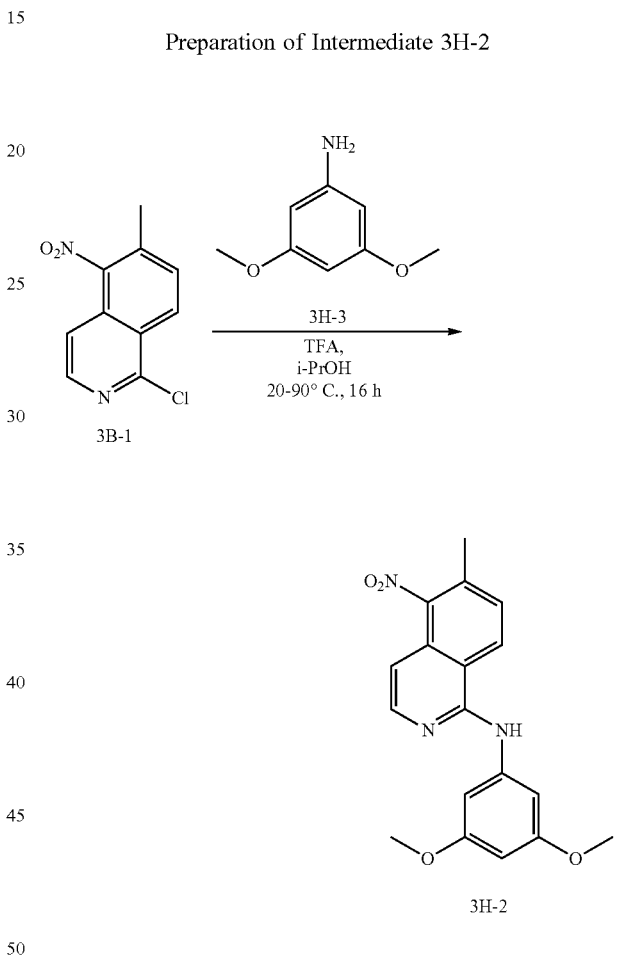

To a mixture of compound 3B-1 (3.00 g, 13.5 mmol, 1.0 eq) in isopropanol (30 mL) was added compound 3H-3 (2.48 g, 16.2 mmol, 1.2 eq) and trifluoroacetic acid (1.54 g, 13.5 mmol, 996 mL, 1.0 eq) at 20° C. under nitrogen. The resulting mixture was heated to 90° C. and stirred at 90° C. for 16 h. TLC (petroleum ether:ethyl acetate=3:1, $R_{f-SM}$=0.43, $R_{f-DP}$=0.24) showed the reaction was completed. The reaction mixture was filtered and filter cake was washed with dichloromethane (10 mL), the filter cake was collected and dried in vacuum to afford compound 3H-2 (4.50 g, 13.3 mmol, 98.4% yield) as a yellow solid, which was used for next step without further purification.

$^1$H NMR: ET15201-5-P1A 400 MHz MeOD

δ 8.75 (d, J=8.4 Hz, 1H), 7.91 (d, J=8.8 Hz, 1H), 7.62 (d, J=7.2 Hz, 1H), 7.06 (d, J=7.2 Hz, 1H), 6.74 (s, 2H), 6.67 (s, 1H), 3.86 (s, 6H), 2.6 (s, 3H).

Preparation of Intermediate 3H

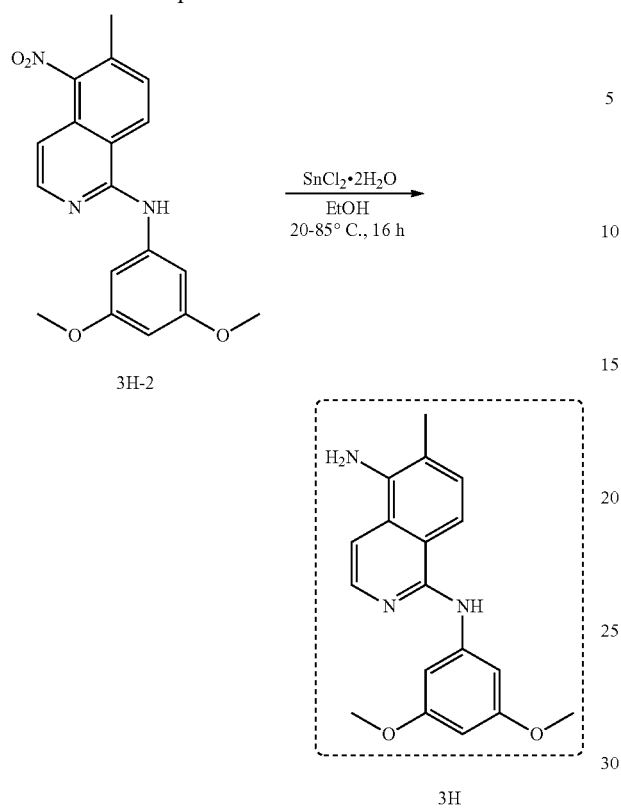

To a mixture of compound 3H-2 (4.50 g, 13.3 mmol, 1.0 eq) in ethanol (45 mL) was added SnCl$_2$·2H$_2$O (15.0 g, 66.3 mmol, 5.0 eq) at 20° C. under nitrogen. The resulting mixture was heated to 85° C. and stirred at 85° C. for 16 h. TLC (petroleum ether:ethyl acetate=3:1, R$_{f\text{-}SM}$=0.43, R$_{f\text{-}DP}$=0.30) showed the reaction was completed. The reaction mixture was cooled to 20° C. and poured to 5 N NaOH aqueous (20 mL) and stirred for 5 min, filtered and the filtrate was extracted with dichloromethane (20 mL, 15 mL). The combined organic phase was dried with anhydrous Na$_2$SO$_4$, filtered and concentrated in vacuum to afford compound 3H (3.80 g, crude) as a red solid, which was used for next step without further purification.

$^1$H NMR: ET15201-7-P1A 400 MHz DMSO-d$_6$
δ 8.77 (s, 1H), 8.15 (s, 1H), 7.90 (d, J=6.0 Hz, 1H), 7.63 (d, J=8.4 Hz, 1H), 7.41 (d, J=6.4 Hz, 1H), 7.23-7.27 (m, 3H), 6.12 (t, J=2.0 Hz, 1H), 5.48 (s, 2H), 3.74 (s, 6H), 2.26 (s, 3H).

Preparation of Intermediate 4H

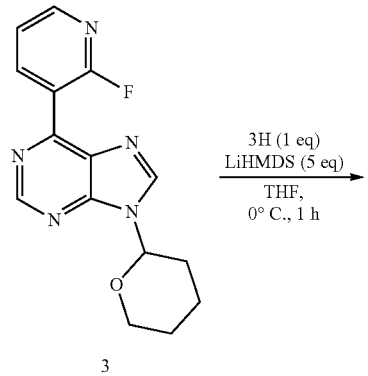

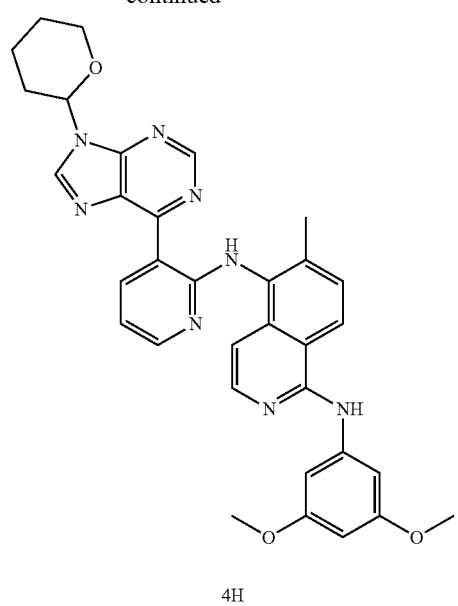

To a mixture of compound 3 (2.00 g, 6.68 mmol, 1.0 eq) and compound 3H (2.07 g, 6.68 mmol, 1.0 eq) in tetrahydrofuran (10 mL) was added LiHMDS (1M, 33 mL, 5.0 eq) at 0° C. under nitrogen. The resulting mixture was stirred at 0° C. for 1 h. TLC (petroleum ether:ethyl acetate=2:1, R$_{f\text{-}SM}$=0.43, R$_{f\text{-}DP}$=0.30) showed the reaction was completed. The reaction mixture was quenched with dropwise addition of ice-water (2.0 mL) at 0° C. while resulting in a light orange solution containing a white solid in suspension. The mixture was concentrated to give a yellow solid which was suspended in ethyl acetate (50 mL), dried with Na$_2$SO$_4$, filtered through a plug of Celite to give a yellow solution and was concentrated in vacuum. The residue was washed with methyl tert-butyl ether (20 mL), filtered to afford the filter cake and filter cake was dried in vacuum to afford compound 4H (2.30 g, crude) as a brown solid.

$^1$H NMR: ET15201-13-P1A 400 MHz DMSO-d$_6$
δ 11.69 (s, 1H), 9.66 (dd, J=6.0, 2.0 Hz, 1H), 9.11 (d, J=8.0 Hz, 1H), 8.98 (s, 1H), 8.41 (d, J=8.4 Hz, 1H), 8.04-8.07 (m, 1H), 7.94 (d, J=6.0 Hz, 1H), 7.59 (d, J=8.8 Hz, 1H), 7.27 (d, J=2.0 Hz, 2H), 7.13 (d, J=5.6 Hz, 1H), 6.89-6.93 (m, 1H), 6.15 (d, J=2.0 Hz, 1H), 5.89 (dd, J=9.2, 2.0 Hz, 1H), 4.07 (d, J=13.2 Hz, 1H), 3.77 (s, 6H), 2.36 (s, 3H), 1.99-2.08 (m, 2H), 1.63-1.81 (m, 3H), 1.10 (s, 1H).

Preparation of Compound of Formula I, R=3,5-dihydroxyphenyl (LUT019)

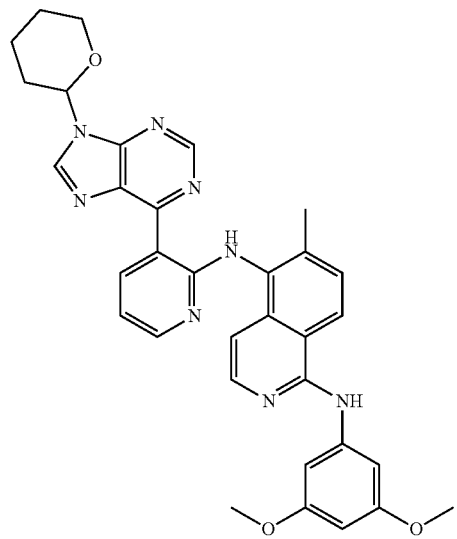

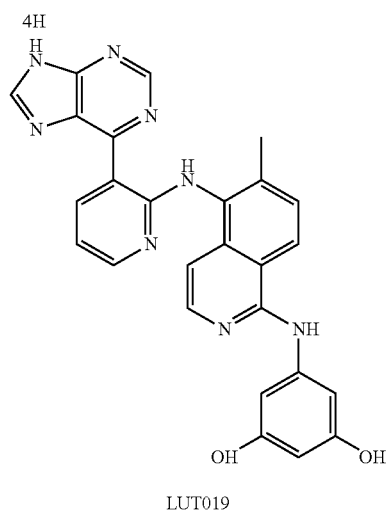
LUT019

To a solution of compound 4H (1.20 g, 2.04 mmol, 1.0 eq) in dichloromethane (10 mL) was added BBr$_3$ (5.11 g, 20.4 mmol, 2.0 mL, 10.0 eq) at 0° C. under nitrogen. The resulting mixture was warmed to 25° C. and stirred for 16 h. LCMS (ET15201-18-P1A2) showed the reaction was completed. The reaction mixture was concentrated in vacuum and poured in saturated NH$_4$Cl aqueous (10 mL), dried with anhydrous Na$_2$SO$_4$, filtered and concentrated in vacuum. The residue was purified by prep-HPLC (column: Waters Xbridge 150*25 5u; mobile phase: [water (0.05% ammonia hydroxide v/v)-MeOH]; B %: 15%-50%, 11 min) to afford product LUT019 (20.0 mg, 40.8 umol, 2.00% yield, 97.1% purity) as a yellow solid.

$^1$HNMR: ET15201-18-P1A2 400 MHz MeOD
δ 9.60 (br. s, 1H), 9.02 (s, 1H), 8.53 (s, 1H), 8.23 (d, J=8.8 Hz, 1H), 7.98 (dd, J=3.2, 1.6 Hz, 1H), 7.74 (d, J=6.0 Hz, 1H), 7.59 (d, J=8.4 Hz, 2H), 7.23 (d, J=7.2 Hz, 1H), 6.90-6.93 (m, 1H), 6.61 (d, J=2.4 Hz, 2H), 6.07 (q, J=2.0 Hz, 1H), 2.43 (s, 3H).

Example 9

Preparation of Compound of Formula I, R=phenyl-3-sulfonamide (LUT020)

Preparation of Intermediate 31-2

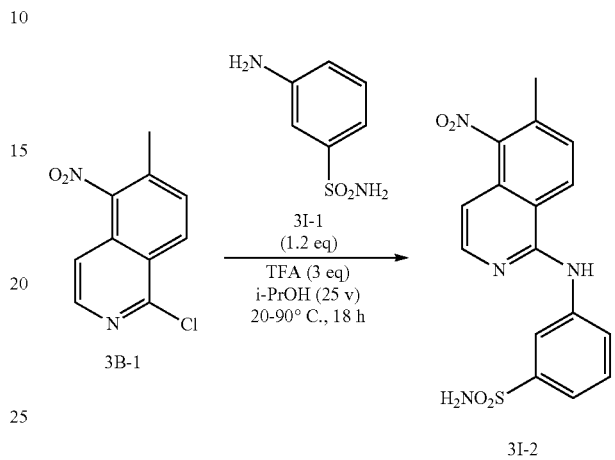

To a mixture of compound 3B-1 (2.00 g, 8.98 mmol, 1.0 eq) and 31-1 (1.86 g, 10.8 mmol, 1.2 eq) in isopropanol (50 mL) was added TFA (3.07 g, 26.9 mmol, 3.0 eq) in one portion at 20° C. under nitrogen. The mixture was stirred at 90° C. for 18 hours. LCMS (ET15060-20-P1A1) showed the reaction was completed. The mixture was cooled to 20° C. and the mixture was filtered. The filter cake was washed with dichloromethane (10 mL) and collected to give product compound 31-2 (3.20 g, 8.93 mmol, 99.4% yield) as a white solid which was used for next step directly without further purification.

$^1$H NMR: ET15060-5-P1A1 400 MHz DMSO-d$_6$
10.19 (s, 1H), 8.82 (d, J=8.8 Hz, 1H), 8.31 (s, 1H), 8.06 (d, J=6.4 Hz, 1H), 7.79 (d, J=8.8, Hz, 1H), 7.54-7.59 (m, 1H), 7.40 (s, 1H), 6.95 (d, J=6.4 Hz, 1H), 2.50 (s, 3H).

Preparation of Intermediate 31

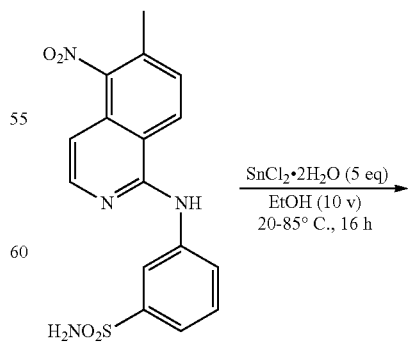

-continued

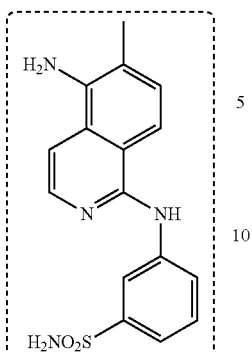

31

To a mixture of compound 31-2 (3.20 g, 8.93 mmol, 1.0 eq) in ethanol (32 mL) was added SnCl$_2$.2H$_2$O (10.1 g, 44.7 mmol, 5.0 eq) in one portion at 20° C. under nitrogen. The mixture was stirred at 85° C. for 16 hours. LCMS (ET15060-23-P1A) showed the reaction was completed. The dark solution was concentrated, diluted with dichloromethane (50 mL), washed with aq. NaOH (1.30 mol/L, 20 mL). The mixture was stirred for 10 min and filtered. The filter was separated and the aqueous phase was concentrated in vacuum. The solid was dissolved in dichloromethane:methanol (8:1, 200 mL). The mixture was filtered and the filtrate was concentrated in vacuum to give compound 31 (2.50 g, 7.61 mmol, 85.3% yield) as a red solid.

$^1$H NMR: ET15060-23-P1A1 400 MHz DMSO-d$_6$
8.98 (s, 1H), 8.20 (s, 1H), 7.94 (s, J=6.8 Hz, 1H), 7.84 (d, J=6.0 Hz, 1H), 7.66 (dd, J=8.8 Hz, 1H), 7.38 (d, J=6.0, Hz, 1H), 7.26-7.28 (m, 2H), 7.21 (d, J=8.4 Hz, 1H), 5.43 (s, 2H), 2.23 (s, 3H).

Preparation of Intermediate 4I

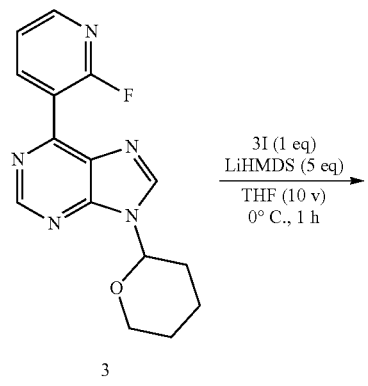

3

-continued

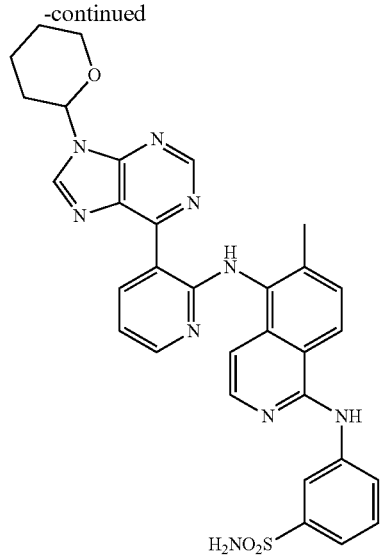

4I

To a mixture of compound 3 (2.00 g, 6.68 mmol, 1.0 eq) and compound 31 (2.19 g, 6.68 mmol, 1.0 eq) in tetrahydrofuran (20 mL) was added drop wise LiHMDS (1M, 33.4 mL, 5.0 eq) at 0° C. under nitrogen. The mixture was stirred at 0° C. for 1 hour. TLC (petroleum ether:ethyl acetate=0:1, R$_f$=0.20) showed the reaction was completed. The deep red reaction mixture was quenched with drop wise addition of water (3 mL—ice bath cooling) resulting in a light orange solution containing a white solid in suspension. The mixture was concentrated to a give yellow solid which was suspended in ethyl acetate (100 mL), dried (MgSO$_4$) and filtered through a plug of Celite to give a yellow solution and concentrated in vacuum. The residue was suspended in MTBE (30 mL) and stirred for 12 h. The mixture was filtered and the filter cake was dried in vacuum to give compound 4I (2.20 g, crude) as a yellow solid.

$^1$H NMR: ET15060-40-P1A1 400 MHz DMSO-d$_6$ (crude)

Preparation of Compound of Formula I, R=phenyl-3-sulfonamide (LUT020)

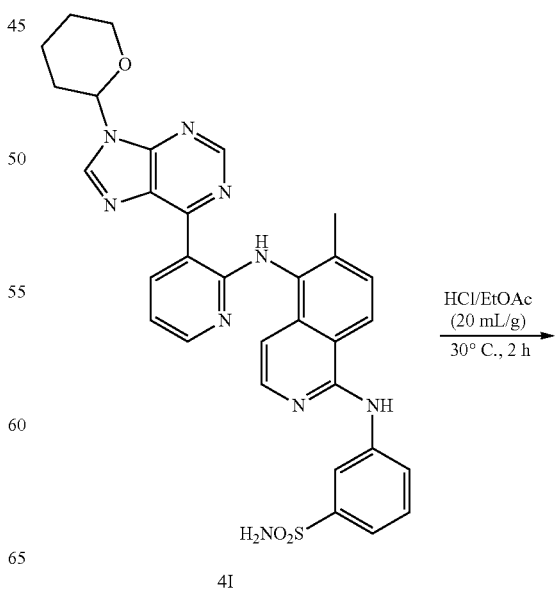

4I

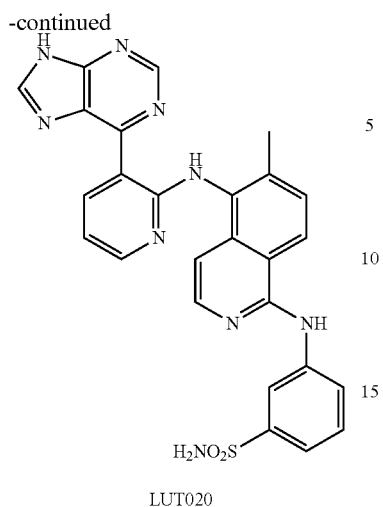

LUT020

Compound 4I (2.00 g, 3.29 mmol, 1.0 eq) was suspended in HCl/EtOAc (4M, 41.1 mL, 50 eq) and stirred at 30° C. for 2 hrs. LCMS (ET15060-45-P1A1) showed the reaction was completed. The solution was filtered, washed with ethyl acetate (2×10 mL). The solid was added water (15 mL). pH value was adjusted to 9 with $Na_2CO_3$ (solid). The mixture was filtered and the filter cake was purified by prep-TLC (petroleum ether:ethyl acetate=0:1, $R_f$=0.10) to give 0.19 g solid. The solid was purified by prep-HPLC (column: YMC-Actus Triart C18 100*30 mm*5 um; liquid phase: [A-10 mM $NH_4HCO_3$ in $H_2O$; B-ACN]B %: 25%-55%, 12 min] to give LUT020 (85.0 mg, 159 umol, 4.83% yield, 98.0% purity) as a yellow solid.

$^1$H NMR: ET15060-45-P1A2 400 MHz DMSO-$d_6$ 13.83 (s, 1H), 11.82 (s, 1H), 9.73 (s, 1H), 9.49 (s, 1H), 9.07 (s, 1H), 8.74 (s, 1H), 8.45-8.47 (m, 2H), 8.16 (d, J=8.8 Hz, 1H), 8.05 (dd, J=4.8, 1.6 Hz, 1H), 7.95 (d, J=6.0 Hz, 1H), 7.63 (d, J=8.8 Hz, 1H), 7.51 (t, J=8.0 Hz, 1H), 7.43 (d, J=8.0 Hz, 1H), 7.33 (s, 2H), 7.19 (d, J=6.0 Hz, 1H), 6.91 (dd, J=8.0, 4.8 Hz, 1H), 2.38 (s, 3H).

Example 10

BRaf Inhibitory Activity of the Compounds of Present Disclosure

In this assay, the BRaf inhibitory activity of the compound of formula I, where

R is 3-(trifluoromethoxy)phenyl (LUT014) and Vemurafenib, a known inhibitor of BRAF containing V600E mutation was tested on wild-type BRaf and BRAF containing V600E mutation. A known inhibitor of BRaf and CRaf, GW5074, was included in the assay as a control. LUT014 and Vemurafenib were tested in 10-dose IC50 mode with a 3-fold serial dilution starting at 10 μM. Control Compound, GW5074, was tested in 10-dose IC50 mode with 3-fold serial dilution starting at 20 μM. Reactions were carried out at 10 μM ATP.

The IC50 values obtained in this assay are shown in the table below.

TABLE 3

| Compound ID | Compound IC50* (M): BRAF | BRAF (V600E) |
| --- | --- | --- |
| Lut014 | 1.17E-08 | 1.33E-08 |
| Vemurafenib | 2.87E-09 | 4.00E-08 |
| GW5074 | 1.99E-08 | 5.87E-09 |

Example 11

Phosphorylation of ERK in Primary Human Keratinocytes

General Procedure

Without wishing to be bound by theory, the inventor believes keratinocytes is likely the site of the cutaneous side-effects, and the inhibition of EGFR and/or its downstream effectors (MAPK, MEK, PI3K, and the like) in keratinocytes is likely the mechanism underlying this side effect. In this experiment, the effect of the compounds of present disclosure on ERK phosphorylation in human keratinocytes was studied. Phosphorylation of ERK indicates its activation.

Human normal keratinocyte cells HEKa were purchased from Gibco Rhenium and seeded in 10 cm dishes (300,000 cells/dish) and incubated overnight at 37° C., 5% $CO_2$. Next morning, the medium was replaced to a starvation medium for 2 hours and then the cells were treated for 2 additional hours with the test compounds. Post incubation, the cells were lyzed with RIPA and the protein extracts were analyzed by western blot for Phospho-ERK and total ERK. Untreated cells and 0.1% DMSO treated cells were used as negative control. HKGS growth factors was used as a positive control.

Western blot: 7.5 μg of total extract was loaded on 10% acrylamide gel. Following transfer, the membranes were blocked with TBST/5% skimmed milk and then incubated with Mouse anti Phospho-ERK (1:1000 in TBST 5% BSA, ON at 4° C.) and goat anti Mouse HRP (1:10,000 in TBST 5% BSA, 1-hour RT). The membranes were exposed using SuperSignal West Pico Chemiluminescent Substrate.

The HRP was then inactivated by incubating the membranes for 1 hour with 0.5% sodium azide Following washes and ECL exposure in order to ensure absence of signal, the membranes were re-blocked for 15 min with TBST/5% skimmed milk and then incubated with Rabbit anti total ERK2 (1:500 in TBST 5% BSA, ON at 4° C.), goat anti Rabbit HRP (1:5,000 in TBST 5% BSA, 1-hour RT) and finally exposed using the SuperSignal West Pico Chemiluminescent Substrate. The films were scanned and the signal were quantified using ImageJ software. The results were calculated as Phospho-ERK/total ERK.

Example 12

ERK Phosphorylation Induced by the Compounds of Present Disclosure—LUT014, LUT015, LUT017

Figure 1B:
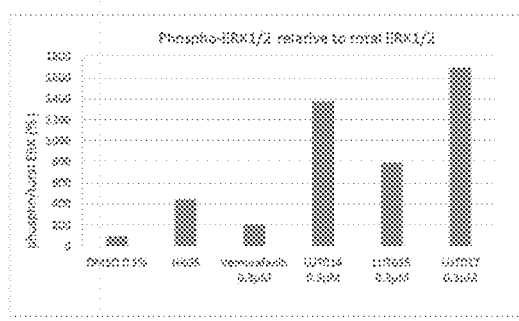
Figure 1C:
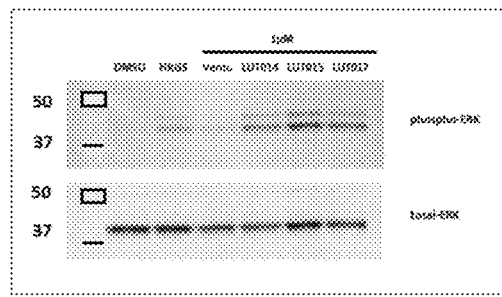
Figure 1D:
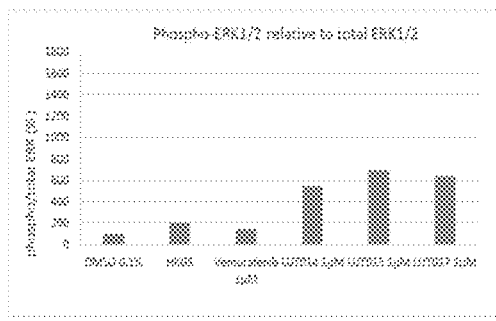

HEKa cells were treated with LUT014, LUT015, LUT017, and Vemurafenib at 0.3 μM and 1 μM as described in Example 11 and the Western blot analysis of HEKa cell lysates was carried out. HKGS growth factors was used as a positive control. FIG. 1A shows Phospho-ERK (upper panel) and total ERK (lower panel) upon treatment with 0.3

µM of the test compounds. FIG. 1B shows the densitometric analysis of blots in FIG. 1A based on the calculation of Phospho-ERK/total ERK ratio. FIG. 1C shows Phospho-ERK (upper panel) and total ERK (lower panel) upon treatment with 1 µM of the test compounds. FIG. 1D shows the densitometric analysis of blots in FIG. 1C based on the calculation of Phospho-ERK/total ERK ratio.

Example 13

ERK Phosphorylation Induced by the Compounds LUT012, LUT016, and C-1

HEKa cells were treated with LUT012, LUT016, and the known compounds—Vemurafenib and C-1 (old batch and new batch) at 0.304 and 104 as described in Example 11 and the Western blot analysis of HEKa cell lysates was carried out. HKGS growth factors was used as a positive control. Compound C-1 has the following structure:

C-1

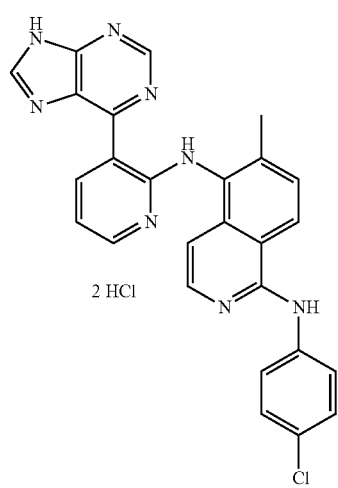

2 HCl

FIG. 2A shows Phospho-ERK (upper panel) and total ERK (lower panel) upon treatment with 0.3 µM of the test compounds. FIG. 2B shows the densitometric analysis of blots in FIG. 2A based on the calculation of Phospho-ERK/total ERK ratio. FIG. 2C shows Phospho-ERK (upper panel) and total ERK (lower panel) upon treatment with 1 µM of the test compounds. FIG. 2D shows the densitometric analysis of blots in FIG. 2C based on the calculation of Phospho-ERK/total ERK ratio.

Example 14

ERK Phosphorylation Induced by the Compounds LUT012, LUT013, LUT014, LUT015, LUT016, LUT017, LUT020 and C-1

Figure 3A:
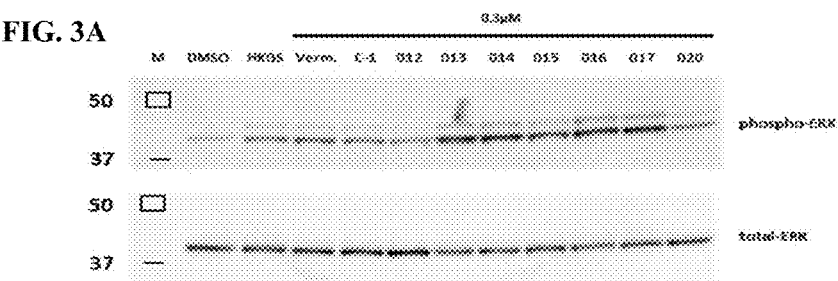
FIGS. 3A-3D depict ERK Phosphorylation induced in HEKa by the compounds—LUT012, LUT013, LUT014, LUT015, LUT016, LUT017, LUT020 and C-1.
Figure 3B:
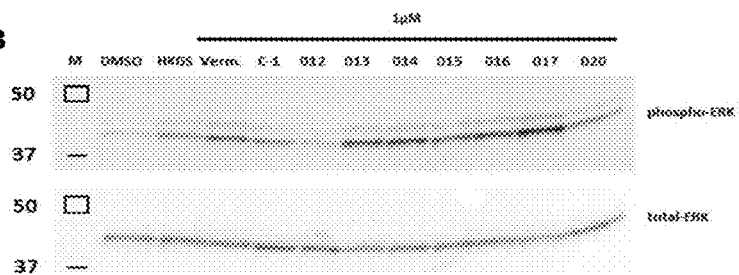
Figure 3C:
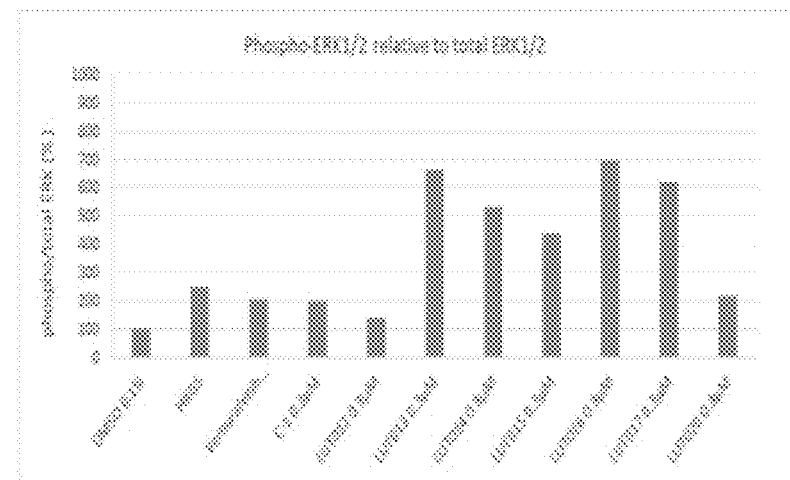
Figure 3D:
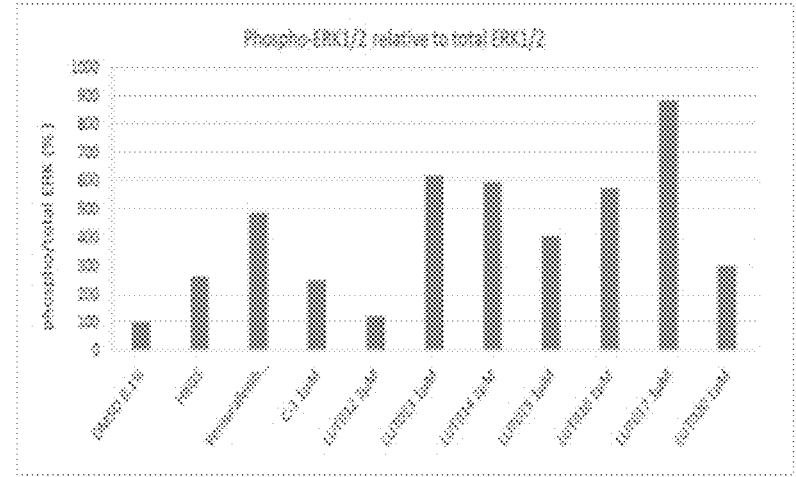

HEKa cells were treated with Vemurafenib, C-1, LUT012, LUT013, LUT014, LUT015, LUT016, LUT017 and LUT020 at 0.3 µM and 1 µM as described in Example 11 and the Western blot analysis of HEKa cell lysates was carried out. HKGS growth factors was used as a positive control. FIG. 3A shows Phospho-ERK (upper panel) and total ERK (lower panel) upon treatment with 0.3 µM of the test compounds. FIG. 3B shows Phospho-ERK (upper panel) and total ERK (lower panel) upon treatment with 1 µM of the test compounds. FIG. 3C shows the densitometric analysis of blots in FIGS. 3A and 3B based on the calculation of Phospho-ERK/total ERK ratio.

Example 15

ERK Phosphorylation Induced by the Novel Compounds LUT014, LUT017 vs. C-1

Figure 4A:
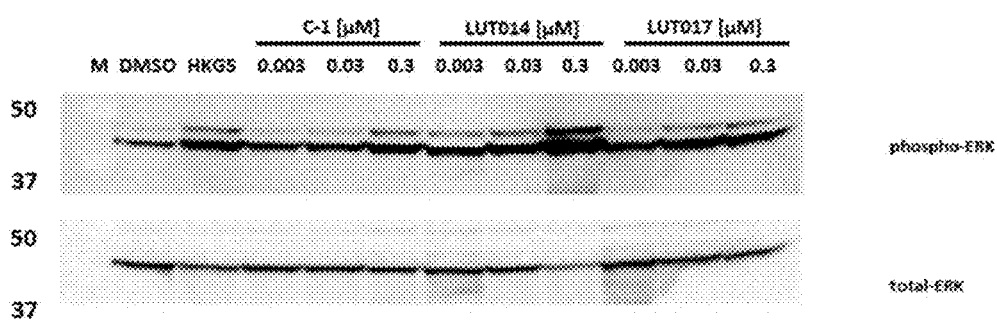
FIGS. 4A and 4B depict ERK Phosphorylation induced in HEKa by the compounds—LUT014, LUT017, and C-1.
Figure 4B:
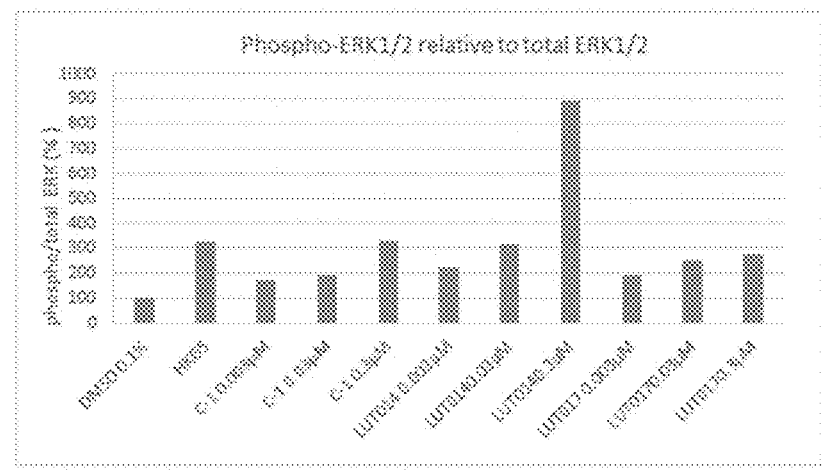
Figure 5A:
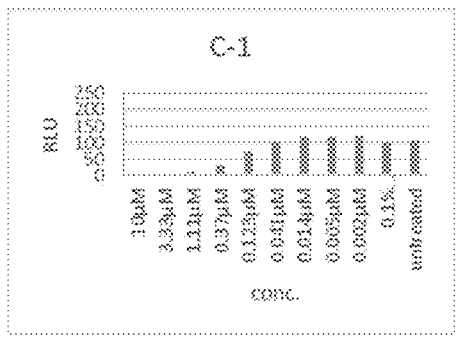
FIGS. 5A-5J depict the effects of the compounds—C-1 (FIG. 5A), LUT-012 (FIG. 5B), LUT-014 (FIG. 5C), Vemurafenib (FIG. 5D), LUT-013 (FIG. 5E), LUT-015 (FIG. 5F), LUT-016 (FIG. 5G), LUT-019 (FIG. 5H), LUT-017 (FIG. 5I), and LUT-020 (FIG. 5J)—on proliferation of MIA PaCa cells.
Figure 5D:
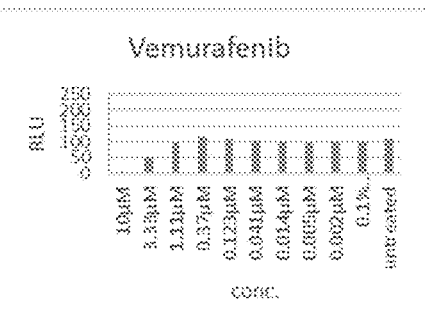
Figure 5B:
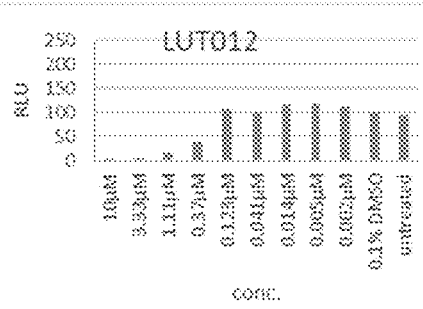
Figure 5E:
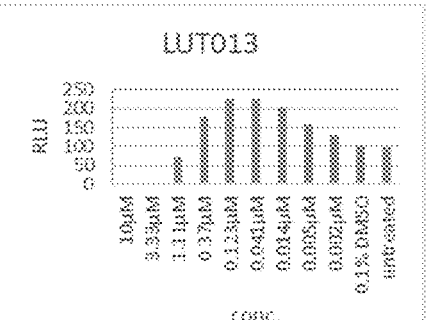
Figure 5C:
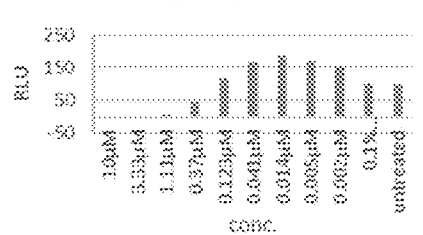
Figure 5F:
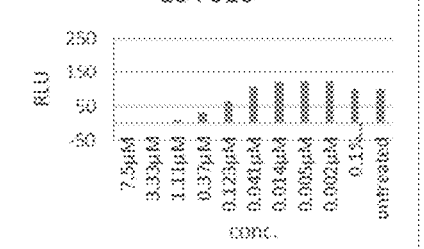
Figure 5G:
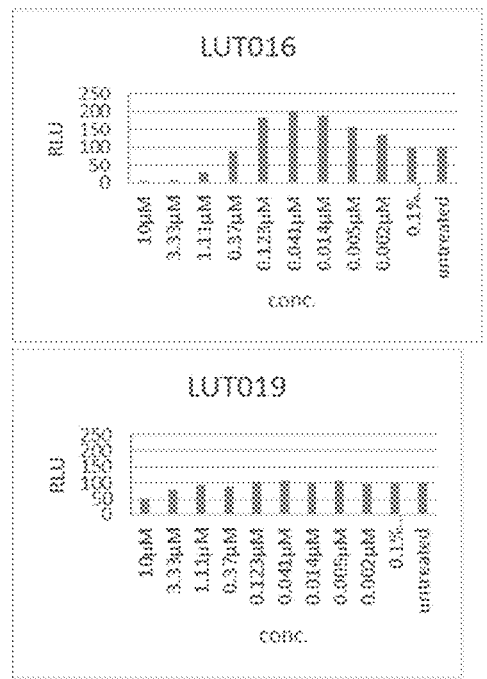
Figure 5H:
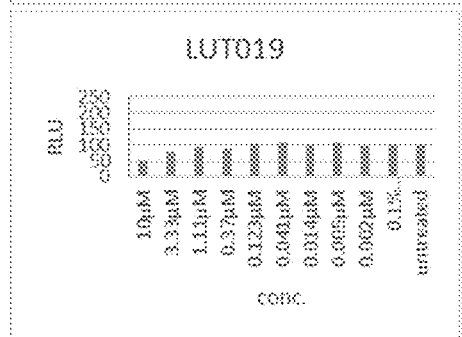
Figure 5I:
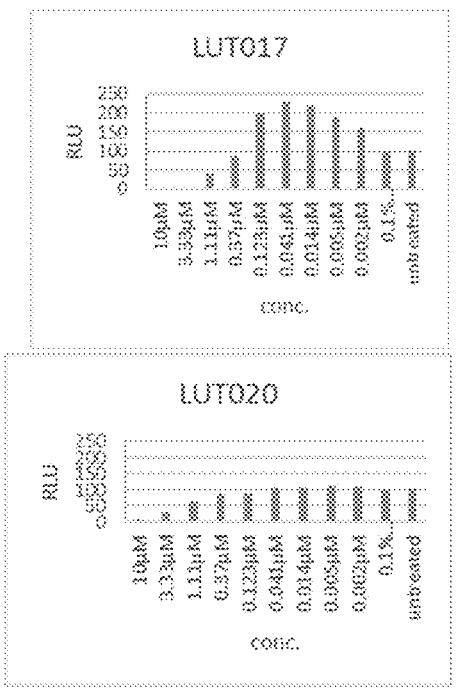
Figure 5J:
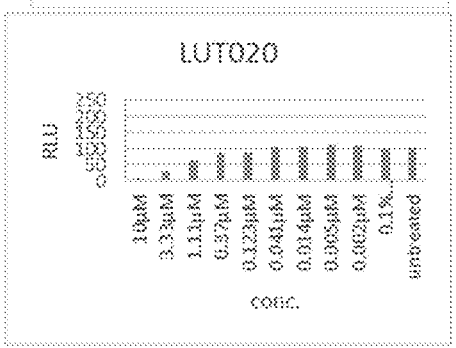

HEKa cells were treated with C-1, LUT014, and LUT017 at a concentration of 0.003 µM, 0.03 µM, and 0.3 µM as described in Example 11 and the Western blot analysis of HEKa cell lysates was carried out. HKGS growth factors was used as a positive control. FIG. 4A shows Phospho-ERK (upper panel) and total ERK (lower panel) upon treatment with 0.003 µM, 0.03 µM, and 0.3 µM of the test compounds. FIG. 4B shows the densitometric analysis of blots in FIG. 4A based on the calculation of Phospho-ERK/total ERK ratio.

Example 16

Effect of the Compounds'LUT012, LUT013, LUT014, LUT015, LUT016, LUT017, LUT-019, LUT020, C-1, and Vemurafenib—on Proliferation of MIA PaCa Cells In this example, effect of the compounds on proliferation of MIA PaCa2 K-ras cells was studied. It was expected that the compounds that induce ERK phosphorylation would also induce proliferation of Mia PaCa cells.

The cells were seeded in starvation medium at 5000 cells/well in a 96 wells plate for 24 hours at 37° C., 5% $CO_2$. The tested compounds were added at different concentrations ranging from 0.002 µM to 10 µM. The controls were untreated cells and vehicle of 0.1% DMSO. The cells were incubated at 37° C., 5% $CO_2$, for 72 hours and then the proliferation was tested using the ATPlite proliferation kit (Perkin-Elmer). Each result represents an average of 6 wells. The results are presented as the percent of over-proliferation compared to the DMSO control. See FIG. 5.

The concentration of the compounds that provided the highest proliferation was compared to DMSO. DMSO was calculated as 100%. After 72 hours, % proliferation compared to the DMSO control induced by C-1 was 30%, LUT013 was 173%, LUT014 was 116%, LUT015 was 29%, LUT016 was 110%, LUT017 was 174%, LUT012 was 20%, LUT019 was 7%, and LUT020 was 12%. Vemurafenib showed 12% proliferation compared to DMSO.

Example 17

Kinase Selectivity Assay Study of Compound I, R=3-(trifluoromethoxy)phenyl (LUT014)

Compound Preparation and Assay Controls

All compounds were prepared to 50× final assay concentration in 100% DMSO. This working stock of the compound was added to the assay well as the first component in the reaction, followed by the remaining components. In the standard KinaseProfiler™ service, there is no pre-incubation step between the compound and the kinase prior to initiation of the reaction. The positive control wells contain all components of the reaction, except the compound of interest; however, DMSO (at a final concentration of 2%) is included in these wells to control for solvent effects. The blank wells contain all components of the reaction, with a reference inhibitor replacing the compound of interest. This abolishes kinase activity and establishes the base-line (0% kinase activity remaining). The results are shown in Table 4.

TABLE 4

Kinase selectivity assay study of compound of formula I,
R = 3-(trifluoromethoxy)phenyl (LUT014)

| | Lut014 @ 0.01 µM | Lut014 @ 1 µM |
|---|---|---|
| Ab1(h) | 92 | 25 |
| ALK(h) | 150 | 83 |
| AMPKα1(h) | 106 | 114 |
| ASK1(h) | 109 | 99 |
| Aurora-A(h) | 95 | 97 |
| CaMKI(h) | 101 | 97 |
| CDK1/cyclinB(h) | 113 | 102 |
| CDK2/cyclinA(h) | 106 | 95 |
| CDK6/cyclinD3(h) | 100 | 103 |
| CDK7/cyclinH/MAT1(h) | 105 | 109 |
| CDK9/cyclin T1(h) | 110 | 98 |
| CHK1(h) | 100 | 114 |
| CK1γ1(h) | 94 | 101 |
| CK2α2(h) | 98 | 92 |
| c-RAF(h) | 105 | 30 |
| DRAK1(h) | 99 | 117 |
| eEF-2K(h) | 95 | 106 |
| EGFR(h) | 98 | 100 |
| EphA5(h) | 99 | 56 |
| EphB4(h) | 93 | 38 |
| Fyn(h) | 103 | 95 |
| GSK3β(h) | 105 | 98 |
| IGF-1R(h) | 88 | 86 |
| IKKα(h) | 105 | 105 |
| IRAK4(h) | 94 | 109 |
| JAK2(h) | 126 | 118 |
| KDR(h) | 96 | 79 |
| LOK(h) | 98 | 83 |
| Lyn(h) | 101 | 46 |
| MAPKAP-K2(h) | 110 | 103 |
| MEK1(h) | 98 | 105 |
| MKK7β(h) | 100 | 103 |
| MLK1(h) | 109 | 112 |
| Mnk2(h) | 112 | 107 |
| MSK2(h) | 92 | 96 |
| MST1(h) | 98 | 112 |
| mTOR(h) | 100 | 96 |
| NEK2(h) | 98 | 125 |
| p70S6K(h) | 108 | 97 |
| PAK2(h) | 95 | 111 |
| PDGFRβ(h) | 98 | 103 |
| Pim-1(h) | 96 | 89 |
| PKA(h) | 114 | 106 |
| PKBα(h) | 102 | 105 |
| PKCα(h) | 102 | 107 |
| PKCθ(h) | 106 | 109 |
| PKG1α(h) | 99 | 111 |
| Plk3(h) | 85 | 87 |
| PRAK(h) | 101 | 103 |
| ROCK-I(h) | 107 | 107 |
| Rse(h) | 106 | 113 |
| Rsk1(h) | 106 | 112 |
| SAPK2a(h) | 97 | 54 |
| SRPK1(h) | 105 | 100 |
| TAK1(h) | 91 | 97 |
| P13 Kinase (p110β/p85α)(h) | 101 | 95 |
| P13 Kinase (p120γ)(h) | 96 | 83 |
| P13 Kinase (p110δ/p85α)(h) | 96 | 94 |
| P13 Kinase (p110α/p85α)(h) | 92 | 84 |

Example 18

Screening of the Compounds for Photo-Toxicity

Certain BRaf inhibitors are known to exhibit phototoxicity. Therefore, the compounds of the present disclosure were screened for phototoxicity using the 3T3 natural red uptake assay.

In brief, BALB/c-3T3 mouse fibroblasts (originally obtained from ATCC) were seeded in 96-well plates at 12,000 cells per well, and grown for 24 hr. Test compounds and the positive control (chlorpromazine) were solubilized and serially diluted in DMSO. The negative control (histidine) was solubilized and diluted in HBSS. A dilution for all test articles was then made into HBSS at the final testing concentrations. At the start of the assay, the growth medium was removed from the plates and replaced with test agent dilution. Six replicates were used for each concentration. Cells were incubated in the dark with test article for 1 h, exposed to UVA light (2.5 J/cm2 over 18 min) and incubated 24 hrs. in the dark. A parallel non-irradiated plate was treated similarly, except it was stored in the dark, rather than illuminated.

For Neutral Red staining, medium was removed and fresh medium containing 25 µg/mL of Neutral Red (Sigma) was added. After three hours incubation, the cells were washed with PBS, and the cellular dye was solubilized with 1% acetic acid in 50% ethanol. Cellular Neutral Red was measured by its absorbance at 540 nm.

Data analysis: An IC50 (concentration that causes 50% reduction in viability) was calculated for each condition by linear interpolation.

A Photo-Irritation Factor (PIF) was calculated: PIF=IC50 (–Irr)/IC50(+Irr) PIF>5 indicates phototoxicity; 2<PIF<5 indicates probable phototoxicity; PIF<2 indicates no phototoxicity In addition, the Mean Photo Effect (MPE) was calculated by comparison of the complete concentration-response curves. MPE is a weighted average of the difference in response of equivalent doses normalized by the shift in IC50.

MPE>0.15 indicates phototoxicity; 0.1<MPE<0.15 indicates probable phototoxicity; MPE<0.1 indicates no phototoxicity.

TABLE 5

Assessment of the Photo-toxicity

| | Cell Viability IC50 | | | | |
|---|---|---|---|---|---|
| Text Article | Minus UVA (µg/ml) | Plus UVA (µg/ml) | Mean PIF | Mean MPE | Comment |
| Histidine | >1000 | >1000 | 1 | 0.036 | Non Phototoxic |
| Chlorpromazine | 31.0 | 0.98 | 31.6 | 0.477 | Phototoxic |
| C-15 | 25.7 | 1.31 | 19.6 | 0.241 | Phototoxic |
| C-19 | >62.5 | 0.18 | >312.5 | 0.571 | Phototoxic |
| C-1 | 14 | 18.12 | 0.8 | –0.011 | Non Phototoxic |

C-15 and C-19 were showed phototoxicity.
C-1 and LUT-104 did not show phototoxicity.

Example 19

In Vitro Effect of LUT014 on Phospho-ERK Following Administration of EGFR Inhibitors HEKa cells were treated with LUT014 and EGFR inhibitors, erlotinib and cetuximab, as described in Example 11. HKGS was used as a positive control. The effect of LUT014 and EGFR inhibitors on phospho-ERK was measured by Western blot as described in Example 11.

Figure 7A:
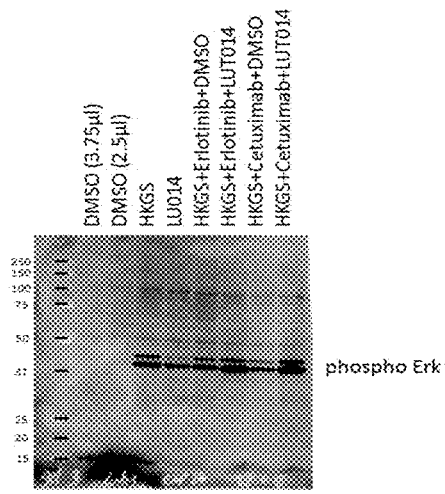
FIGS. 7A-7C depict the effect of LU014 on phospho-ERK following administration of EGFR (in vitro results).
Figure 7B:
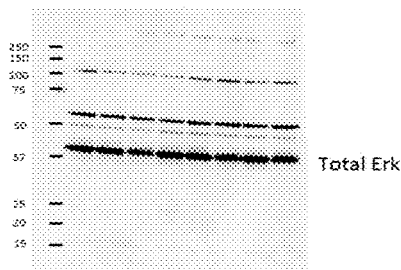
Figure 7C:
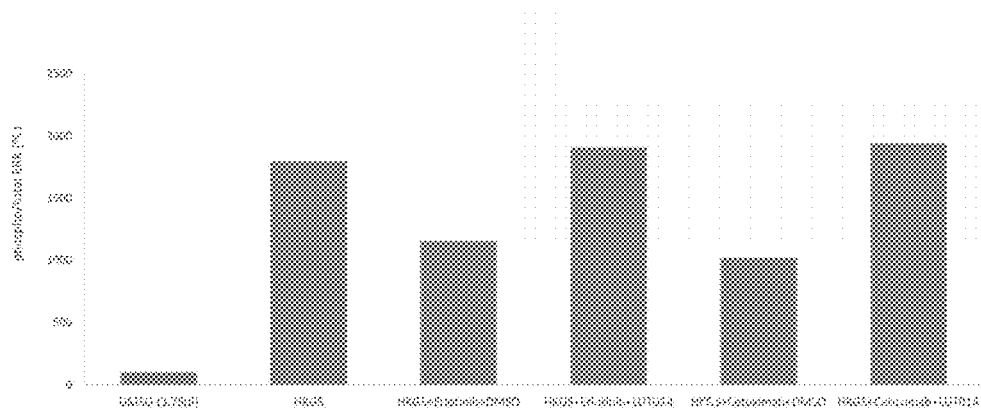

FIGS. 7A-7C and Table 6 shows the results of the effect of LUT014 on Phospho-ERK following administration of EGFR inhibitors

TABLE 6

The effect of LUT014 and EGFRI on phospho-ERK

| Gel #3 | phospho ERK | Total ERK | phospho/total ratio | % of control |
|---|---|---|---|---|
| DMSO (3.75 µl) | 539.971 | 7316.397 | 0.07 | 100.0 |
| HKGS | 9391.983 | 7094.569 | 1.32 | 1793.7 |
| HKGS + Erlotinib + DMSO | 7790.296 | 9117.004 | 0.85 | 1157.8 |
| HKGS + Erlotinib + LUT014 | 10848.175 | 7696.983 | 1.41 | 1909.7 |
| HKGS + Cetuximab + DMSO | 6291.861 | 8346.569 | 0.75 | 1021.4 |
| HKGS + Cetuximab + LUT014 | 11594.983 | 8095.397 | 1.43 | 1940.7 |

LUT014 increased phospho-ERK by 200-800% compared to the DMSO treated cells. Erlotinib decreased phospho ERK compared to HKGS treated cells. LUT014 increased phospho-ERK when added to cells treated with Erlotinib. LUT014 increased phospho-ERK when added to cells treated with cetuximab.

Example 20

Permeation Studies Using a Topical Composition Comprising LUT014

An ex vivo permeation and penetration experiment for a topical composition comprising LUT-014 was conducted using MedFlux-HT™ continuous flow through diffusion cells. A skin sample was placed between donor and receptor compartments of the diffusion cell. The diffusion of the topical composition was measured using a citrate/phosphate buffer (pH 4.0) with 0.01% Brij as a receptor solution. LUT014 permeated into the skin sample was extracted using 90/10 acetonitrile/water as an extraction solvent.

The maximum accumulated level of LUT014 observed in the receptor solution after 24 hours was less than 2 ng/mL.

Example 21

Toxicity studies for the present compounds using LUT014 as an exemplary compound were conducted. The results are summarized below.

Oral administration of LUT014, for 7 days in the Wistar rat at dose levels of 250, 500 and 1000 mg/kg/day did not result in mortality.

Dermal administration of LUT014 was well tolerated in minipigs at levels of 5 mg/kg/day for up to 6 days.

The results of in vitro Ames test showed that LUT014 is not mutagenic in the *Salmonella typhimurium* reverse mutation assay and in the *Escherichia coli* reverse mutation assay.

Since LUT014 induced an IVIS≤3, no classification is required for eye irritation or serious eye damage, as was observed by BCOP study.

LUT014 is classified as non-phototoxic (3T3 NRU)

TABLE 7

Toxicity Studies

| Study | Results |
|---|---|
| DRF oral in Wistar Rats | Oral administration of Lut014, for 7 days in the Wistar rat at dose levels of 250, 500 and 1000 mg/kg/day did not result in mortality |
| MTD Dermal Minipigs | Dermal administration of LUT014 was well tolerated in minipigs at levels of 5 mg/kg/day for up to 6 days. |
| Sensitization GP | The test article is not a dermal sensitizer |
| In vitro Ames test | Lut014 is not mutagenic in the *Salmonella typhimurium* reverse mutation assay and in the *Escherichia coli* reverse mutation assay. |
| 20145601-BCOP | Lut014 induced an IVIS ≤3, no classification is required for eye irritation or serious eye damage |
| 3T3 NRU | Lut014 is classified as non-phototoxic |

Example 22

A Phase 1/2 multi-center two-phase study was devised.

Primary Objective:
To evaluate the safety, and pharmacokinetics of LUT014 in colorectal cancer patients who are receiving EGFR inhibitors.

Secondary Objectives:
Estimate the efficacy of LUT014 in the treatment of grade 1 and 2 acneiform lesions occurring in colorectal cancer patients receiving EGFR inhibitors.

Patient Population:
Colorectal cancer patients receiving EGFR inhibitors who have developed acneiform lesions.

Methodology:
This is a multi-center, open-label, dose escalation study that will determine the maximum tolerated dose (MTD), establish the pharmacokinetics of LUT014, and estimate the efficacy of LUT014 in treating patients receiving EGFR inhibitor therapy and who have developed acneiform lesions.

Enrollment will initially occur in cohorts of three subjects in a conventional 3+3 escalating dose design. Patients receiving EGFR inhibitors and who have developed grade 1 or 2 acneiform lesions will be treated with LUT014 for 4 weeks. The LUT014 gel will be applied each morning after bathing or showering. Application will be to the face and, the upper portion of the anterior and posterior chest. A thin layer of the gel will be applied.

In the initial cohort of LUT014 if no dose limiting toxicity (DLT) occurs in the initial 3 patients, or in 1 of 6 patients if this cohort goes to 6 patients during the 4 weeks of therapy, the second cohort will begin. For this second dosing regimen, patients will again have LUT014 applied to their face, plus their upper anterior and posterior chest on a daily basis after bathing for 4 weeks. If no DLTs are observed in the initial 3 patients treated in this cohort, or in 1 of 6 patients if this second cohort goes to 6 patients, a third cohort of 3 patients, or 6 patients if this third cohort goes to 6 patients, will be treated. These patients will also have LUT014 applied over their face, anterior and posterior chest on a daily basis after bathing for 4 weeks For each dosing cohort, if no subject experiences a DLT, based on National Cancer Institute (NCI) Common Terminology Criteria for Adverse Events (CTCAE) v4.03, which constitutes a Grade 3 or higher toxicity, the subsequent group of three subjects will receive the next higher LUT014 dosing regimen. However, if one of the three initial subjects experiences a DLT, the cohort of subjects in that dosing regimen will be expanded to six subjects. If at least two of the six subjects experience a DLT, this will be considered a non-tolerated dose.

The MTD is defined as the highest dosing concentration of LUT014 at which fewer than two (of a cohort of up to six) subjects experience a DLT.

Determination of a DLT will require that the Grade 3 or greater toxicity occur and be determined to be possibly, probably or definitely related to the study drug by an independent safety review committee.

Following completion of the dose escalation phase of the study, up to 60 patients will be enrolled and randomized to have either LUT014 at the MTD or a smaller dose chosen by the sponsor or will be treated with an identical appearing vehicle. The LUT014 or vehicle will be applied to their skin over all areas with evidence of acneiform lesions. Patients will be treated for 4 weeks.

What is claimed is:

1. A compound of formula (I):

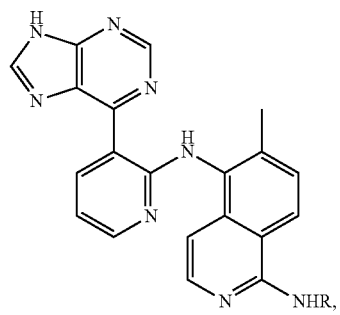

wherein R is selected from the group consisting of 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, or a pharmaceutically acceptable salt or a solvate thereof.

2. The compound of formula I of claim 1, wherein R is 3-(trifluoromethoxy)phenyl.

3. The compound of formula I of claim 1, wherein the compound inhibits the activity of BRaf.

4. The compound of formula I of claim 1, wherein the compound has a photo-irritation factor (PIF) of less than 5.

5. The compound of formula I of claim 1, wherein the compound has a mean photo effect (MPE) of less than 0.15.

6. A pharmaceutical composition, comprising:
a compound of formula (I):

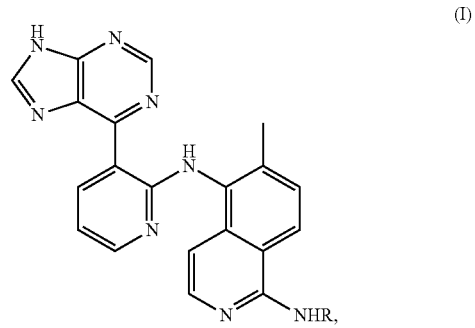

wherein R is selected from the group consisting of 3-chloro-4-fluorophenyl, 2-fluoro-4-iodophenyl, 4-chloro-3-(trifluoromethyl)phenyl, 3-(1,1-dimethylethyl)-1-methyl-1H-pyrazol-5-yl, 3-(trifluoromethoxy)phenyl, or a pharmaceutically acceptable salt or a solvate thereof; and
a pharmaceutically acceptable carrier or excipient,
wherein a sufficient amount of the composition increases activity of Mitogen-Activated Protein Kinase by at least 2 times compared to activity of Mitogen-Activated Protein Kinase of a composition comprising a compound of formula (I) wherein R is p-chlorophenyl.

7. The pharmaceutical composition of claim 6, wherein R is 3-(trifluoromethoxy)phenyl.

8. The pharmaceutical composition of claim 6, wherein the composition is formulated for systemic administration.

9. The pharmaceutical composition of claim 6, wherein the composition is formulated for topical administration.

10. The pharmaceutical composition of claim 6, wherein the composition is administered orally in the form of a tablet, a capsule, a liquid, a suspension or a powder.

11. The pharmaceutical composition of claim 6, wherein the composition is in the form of a gel, a hydrogel, an ointment, a cream, a foam, a spray, a lotion, a liquid or a dermal patch.

12. The pharmaceutical composition of claim 6, wherein the compound is present at a concentration of 1% w/w to 5% w/w of the total weight of the composition.

13. The pharmaceutical composition of claim 6, wherein the compound is present at a concentration of 5% w/w to 10% w/w of the total weight of the composition.

14. A method of treating and/or ameliorating a cutaneous adverse reaction to EGFR inhibitors, PI3K inhibitors, MEK inhibitors or combinations thereof in a subject in need thereof, comprising administering the pharmaceutical composition of claim 6 comprising the therapeutically effective amount of the compound of formula (I),
wherein a sufficient amount of the pharmaceutical composition increases activity of Mitogen-Activated Protein Kinase by at least 2 times compared to activity of Mitogen-Activated Protein Kinase of a composition comprising a compound of formula (I) wherein R is p-chlorophenyl;
and wherein the cutaneous adverse reaction is selected from acneiform rash, papulopustular rash, abnormal scalp hair growth, abnormal facial hair growth, abnormal hair growth, abnormal eyelash growth, paronychia with or without pyogenic granulomas and telangiectasia and combinations thereof.

15. The method of claim 14 wherein R is 3-(trifluoromethoxy)phenyl.

16. The method of claim 14, wherein the cutaneous adverse reaction is acneiform rash.

17. The method of claim 14, wherein the subject is treated with an EGFR inhibitor, a PI3K inhibitor, a MEK inhibitor or a combination thereof, prior to administration of the pharmaceutical composition.

18. The method of claim 14, wherein the EGFR inhibitor is selected from: Iressa® (gefitinib), Tarceva® (erlotinib), Tykerb® (lapatinib), Erbitux® (cetuximab), Vectibix® (panitumumab), Caprelsa® (vandetanib), Portrazza® (necitumumab), Tagrisso® (osimertinib) and combinations thereof.

19. The method of claim 14, wherein the PI3K inhibitor is selected from GDC-0980 (Apitolisib), GDC-0941 (Pictilisib), BAY 80-6946 (Copanlisib), BKM120 (Buparlisib), NVP-BEZ235 (Dactolisib), IPI 145 (Duvelisib), Idelalisib (GS-1101 or CAL-101), wortmannin and LY294002 and combinations thereof.

20. The method of claim 14, wherein the MEK inhibitor is selected from Trametinib (GSK1120212), Cobimetinib (XL518), Binimetinib (MEK162), Selumetinib, PD-325901, CI-1040, PD035901, UO126, TAK-733 and combinations thereof.

21. The method of claim 14, wherein the pharmaceutical composition is administered topically.

22. The method of claim 14, wherein the composition administered topically is in the form of a gel, a hydrogel, an ointment, a cream, a spray, a dermal patch, a foam, a lotion or a liquid.

23. The method of claim 14, wherein the pharmaceutical composition is administered systemically and the systemic administration is selected from enteral administration and parenteral administration.

24. The method of 14, wherein the method reduces the severity or prevents the escalation of the cutaneous adverse reaction.

\* \* \* \* \*